US009950125B2

(12) United States Patent
Wotton et al.

(10) Patent No.: US 9,950,125 B2
(45) Date of Patent: Apr. 24, 2018

(54) NEEDLE ASSISTED JET INJECTION ADMINISTRATION OF TESTOSTERONE COMPOSITIONS

(71) Applicants: Paul K. Wotton, Newtown, PA (US); Kaushik J. Dave, Edison, NJ (US); John W. Hayes, Chaska, MN (US); Peter L. Sadowski, Woodbury, MN (US); Hermanus L. Jooste, Wayne, PA (US); Jonathan Jaffe, Annandale, NJ (US)

(72) Inventors: Paul K. Wotton, Newtown, PA (US); Kaushik J. Dave, Edison, NJ (US); John W. Hayes, Chaska, MN (US); Peter L. Sadowski, Woodbury, MN (US); Hermanus L. Jooste, Wayne, PA (US); Jonathan Jaffe, Annandale, NJ (US)

(73) Assignee: ANTARES PHARMA, INC., Ewing, NJ (US)

( * ) Notice: Subject to any disclaimer, the term of this patent is extended or adjusted under 35 U.S.C. 154(b) by 1248 days.

(21) Appl. No.: 13/857,859

(22) Filed: Apr. 5, 2013

(65) Prior Publication Data
US 2013/0303985 A1 Nov. 14, 2013

Related U.S. Application Data

(60) Provisional application No. 61/621,298, filed on Apr. 6, 2012, provisional application No. 61/783,444, filed on Mar. 14, 2013, provisional application No. 61/776,283, filed on Mar. 11, 2013, provisional application No. 61/763,395, filed on Feb. 11, 2013.

(51) Int. Cl.
| | |
|---|---|
| *A61M 5/42* | (2006.01) |
| *A61M 37/00* | (2006.01) |
| *A61K 31/56* | (2006.01) |
| *A61M 5/00* | (2006.01) |
| *A61M 5/315* | (2006.01) |
| *A61M 5/32* | (2006.01) |
| *A61M 5/20* | (2006.01) |
| *A61M 5/30* | (2006.01) |
| *A61K 31/568* | (2006.01) |
| *A61K 9/00* | (2006.01) |
| *A61M 5/44* | (2006.01) |

(52) U.S. Cl.
CPC ........... *A61M 5/425* (2013.01); *A61K 9/0019* (2013.01); *A61K 31/56* (2013.01); *A61K 31/568* (2013.01); *A61M 5/002* (2013.01); *A61M 5/2033* (2013.01); *A61M 5/30* (2013.01); *A61M 5/3153* (2013.01); *A61M 5/3202* (2013.01); *A61M 5/326* (2013.01); *A61M 5/44* (2013.01); *A61M 37/00* (2013.01); *A61M 2005/206* (2013.01); *A61M 2005/2013* (2013.01); *A61M 2005/2073* (2013.01); *A61M 2205/364* (2013.01); *A61M 2205/3613* (2013.01); *A61M 2205/3673* (2013.01)

(58) Field of Classification Search
None
See application file for complete search history.

(56) References Cited

U.S. PATENT DOCUMENTS

| | | | |
|---|---|---|---|
| 547,370 | A | 10/1895 | Chalefou |
| 1,465,793 | A | 8/1923 | Schilling |
| 1,512,294 | A | 10/1924 | Marcy |
| 1,687,323 | A | 10/1928 | Cook |
| 2,354,649 | A | 8/1944 | Bruckner |
| 2,607,344 | A | 8/1952 | Brown |
| 2,645,223 | A | 7/1953 | Lawshe |
| 2,648,334 | A | 8/1953 | Brown |
| 2,687,730 | A | 8/1954 | Hein |
| 2,688,967 | A | 9/1954 | Huber |
| 2,699,166 | A | 1/1955 | Bickinson |
| 2,717,601 | A | 9/1955 | Brown |
| 2,728,341 | A | 12/1955 | Roehr |
| 2,737,946 | A | 3/1956 | Hein, Jr. |
| 2,813,528 | A | 11/1957 | Blackman |
| 2,866,458 | A | 12/1958 | Mesa et al. |
| 2,888,924 | A | 6/1959 | Dunmire |
| 2,893,390 | A | 7/1959 | Lockhart |
| 3,130,724 | A | 4/1964 | Higgins |
| 3,166,069 | A | 1/1965 | Enstrom |
| 3,375,825 | A | 4/1968 | Keller |
| 3,382,865 | A | 5/1968 | Worrall |
| 3,526,225 | A | 9/1970 | Hayamamachi |

(Continued)

FOREIGN PATENT DOCUMENTS

| | | |
|---|---|---|
| AR | 00081651 | 10/2012 |
| AR | 082053 | 11/2012 |

(Continued)

OTHER PUBLICATIONS

Zumpe and Michael, Hormones and Behavior, 19; 1985: 265-277.*
Desjardins et al., Endocrinology, 1973; 93: 450-460.*
Damassa et al., Hormones and Behavior, 1977; 8: 275-286.*
Conway et al., International Journal of Andrology, 1988; 11: 247-264.*
Armagan et al., Journal of Andrology, 2006; 27: 517-526.*
Winslow et al., Psychopharmacology (Berl). 1988; 95: 356-63.*
Swerdloff and Jaffe, Endocrine Society's 96th Annual Meeting and Expo, Jun. 21-24, 2014—Chicago; presentation No. SUN-0056.*
Kratochvil et al., Steroids. 1970; 15: 505-511.*
The paper prepared at the 37th JECFA (1990), published in FNP 52; May 1992 pages total.*

(Continued)

*Primary Examiner* — Christina Borgeest
(74) *Attorney, Agent, or Firm* — Morgan, Lewis & Bockius LLP

(57) ABSTRACT

The present invention provides compositions and methods for treating a subject in need of treatment with testosterone, including introducing testosterone into the subject subcutaneously, intradermally, or intramuscularly, from a needle assisted jet injection device.

18 Claims, 15 Drawing Sheets

(56) References Cited

U.S. PATENT DOCUMENTS

| | | |
|---|---|---|
| 3,557,784 A | 1/1971 | Shields |
| 3,563,098 A | 2/1971 | Gley |
| 3,605,744 A | 9/1971 | Dwyer |
| 3,688,765 A | 9/1972 | Gasaway |
| 3,702,609 A | 11/1972 | Steiner |
| 3,712,301 A | 1/1973 | Sarnoff |
| 3,742,948 A | 7/1973 | Post et al. |
| 3,770,026 A | 11/1973 | Isenberg |
| 3,790,048 A | 2/1974 | Luciano et al. |
| 3,797,489 A | 3/1974 | Sarnoff |
| 3,797,491 A | 3/1974 | Hurschman |
| 3,811,441 A | 5/1974 | Sarnoff |
| 3,831,814 A | 8/1974 | Butler |
| 3,848,593 A | 11/1974 | Baldwin |
| 3,882,863 A | 5/1975 | Sarnoff et al. |
| 3,892,237 A | 7/1975 | Steiner |
| 3,895,633 A | 7/1975 | Bartner et al. |
| 3,946,732 A | 3/1976 | Hurscham |
| 4,031,893 A | 6/1977 | Kaplan et al. |
| 4,067,333 A | 1/1978 | Reinhardt et al. |
| 4,127,118 A | 11/1978 | Latorre |
| 4,171,698 A | 10/1979 | Genese |
| 4,181,721 A | 1/1980 | Speck et al. |
| 4,222,392 A | 9/1980 | Brennan |
| 4,227,528 A | 10/1980 | Wardlaw |
| 4,258,713 A | 3/1981 | Wardlaw |
| 4,282,986 A | 8/1981 | af Ekenstam et al. |
| 4,316,463 A | 2/1982 | Schmitz et al. |
| 4,316,643 A | 2/1982 | Burk et al. |
| 4,328,802 A | 5/1982 | Curley et al. |
| 4,333,456 A | 6/1982 | Webb |
| 4,333,458 A | 6/1982 | Margulies et al. |
| 4,338,980 A | 7/1982 | Schwebel et al. |
| 4,373,526 A | 2/1983 | Kling |
| 4,378,015 A | 3/1983 | Wardlaw |
| 4,411,661 A | 10/1983 | Kersten |
| 4,484,910 A | 11/1984 | Sarnoff et al. |
| 4,529,403 A | 7/1985 | Kamstra |
| 4,553,962 A | 11/1985 | Brunet |
| 4,558,690 A | 12/1985 | Joyce |
| 4,573,971 A | 3/1986 | Kamstra |
| 4,592,745 A | 6/1986 | Rex et al. |
| 4,624,660 A | 11/1986 | Mijers et al. |
| 4,634,027 A | 1/1987 | Kanarvogel |
| 4,661,098 A | 4/1987 | Bekkering et al. |
| 4,662,878 A | 5/1987 | Lindmayer |
| 4,664,653 A | 5/1987 | Sagstetter et al. |
| 4,664,655 A | 5/1987 | Orentreich et al. |
| 4,678,461 A | 7/1987 | Mesa |
| 4,719,825 A | 1/1988 | LaHaye et al. |
| 4,722,728 A | 2/1988 | Dixon |
| 4,774,772 A | 10/1988 | Vetter et al. |
| 4,790,824 A | 12/1988 | Morrow et al. |
| 4,818,517 A | 4/1989 | Kwee et al. |
| 4,820,286 A | 4/1989 | van der Wal |
| 4,822,340 A | 4/1989 | Kamstra |
| 4,830,217 A | 5/1989 | Dufresne et al. |
| 4,874,381 A | 10/1989 | Vetter |
| 4,883,472 A | 11/1989 | Michel |
| 4,913,699 A | 4/1990 | Parsons |
| 4,915,701 A | 4/1990 | Halkyard |
| 4,929,238 A | 5/1990 | Baum |
| 4,936,833 A | 6/1990 | Sams |
| 4,940,460 A | 7/1990 | Casey et al. |
| 4,966,581 A | 10/1990 | Landau |
| 4,968,302 A | 11/1990 | Schluter et al. |
| 4,973,318 A | 11/1990 | Holm et al. |
| 4,976,701 A | 12/1990 | Ejlersen et al. |
| 4,982,769 A | 1/1991 | Fournier et al. |
| 4,986,816 A | 1/1991 | Steiner et al. |
| 5,042,977 A | 8/1991 | Bechtold et al. |
| 5,062,830 A | 11/1991 | Dunlap |
| 5,064,413 A | 11/1991 | McKinnon et al. |
| 5,069,670 A | 12/1991 | Vetter et al. |
| 5,078,680 A | 1/1992 | Sarnoff |
| 5,080,648 A | 1/1992 | D'Antonio |
| 5,080,649 A | 1/1992 | Vetter |
| 5,085,641 A | 2/1992 | Sarnoff et al. |
| 5,085,642 A | 2/1992 | Sarnoff et al. |
| 5,092,842 A | 3/1992 | Bechtold et al. |
| 5,102,388 A | 4/1992 | Richmond |
| 5,102,393 A | 4/1992 | Sarnoff et al. |
| 5,104,380 A | 4/1992 | Holman et al. |
| 5,114,406 A | 5/1992 | Gabriel et al. |
| 5,137,516 A | 8/1992 | Rand et al. |
| 5,137,528 A | 8/1992 | Crose |
| 5,139,490 A | 8/1992 | Vetter et al. |
| 5,163,907 A | 11/1992 | Szuszkiewicz |
| 5,176,643 A | 1/1993 | Kramer et al. |
| 5,180,370 A | 1/1993 | Gillespie |
| 5,185,985 A | 2/1993 | Vetter et al. |
| 5,195,983 A | 3/1993 | Boese |
| 5,221,348 A | 6/1993 | Masano |
| 5,226,895 A | 7/1993 | Harris |
| 5,232,459 A | 8/1993 | Hjertman |
| 5,256,142 A | 10/1993 | Colavecchio |
| 5,263,934 A | 11/1993 | Haak |
| 5,271,744 A | 12/1993 | Kramer et al. |
| 5,279,543 A | 1/1994 | Glikfeld et al. |
| 5,279,576 A | 1/1994 | Loo et al. |
| 5,279,585 A | 1/1994 | Balkwill |
| 5,279,586 A | 1/1994 | Balkwill |
| 5,281,198 A | 1/1994 | Haber et al. |
| 5,290,228 A | 3/1994 | Uemura et al. |
| 5,295,965 A | 3/1994 | Wilmot |
| 5,300,030 A | 4/1994 | Crossman et al. |
| 5,304,128 A | 4/1994 | Haber et al. |
| 5,304,152 A | 4/1994 | Sams |
| 5,308,341 A | 5/1994 | Chanoch |
| 5,318,522 A | 6/1994 | D'Antonio |
| 5,320,603 A | 6/1994 | Vetter et al. |
| 5,330,431 A | 7/1994 | Herskowitz |
| 5,332,399 A | 7/1994 | Grabenkort et al. |
| 5,334,144 A | 8/1994 | Alchas et al. |
| 5,342,308 A | 8/1994 | Boschetti |
| 5,350,367 A | 9/1994 | Stiehl et al. |
| 5,354,286 A | 10/1994 | Mesa et al. |
| 5,358,489 A | 10/1994 | Wyrick |
| RE34,845 E | 1/1995 | Vetter et al. |
| 5,391,151 A | 2/1995 | Wilmot |
| 5,405,362 A | 4/1995 | Kramer et al. |
| 5,415,648 A | 5/1995 | Malay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,505,694 A | 4/1996 | Hubbard et al. |
| 5,514,097 A | 5/1996 | Knauer |
| 5,514,107 A | 5/1996 | Haber et al. |
| 5,540,664 A | 7/1996 | Wyrick |
| 5,542,760 A | 8/1996 | Chanoch et al. |
| 5,544,234 A | 8/1996 | Terajima et al. |
| 5,549,561 A | 8/1996 | Hjertman |
| 5,554,134 A | 9/1996 | Bonnichsen |
| 5,562,625 A | 10/1996 | Stefancin, Jr. |
| 5,567,160 A | 10/1996 | Massino |
| 5,569,190 A | 10/1996 | D'Antonio |
| 5,569,192 A | 10/1996 | van der Wal |
| 5,569,236 A | 10/1996 | Kriesel |
| 5,573,042 A | 11/1996 | De Haen |
| 5,593,388 A | 1/1997 | Phillips |
| 5,599,302 A | 2/1997 | Lilley et al. |
| 5,599,309 A | 2/1997 | Marshall et al. |
| 5,605,542 A | 2/1997 | Tanaka et al. |
| 5,637,094 A | 6/1997 | Stewart, Jr. et al. |
| 5,637,100 A | 6/1997 | Sudo |
| 5,649,912 A | 7/1997 | Peterson |
| 5,658,259 A | 8/1997 | Pearson et al. |
| 5,665,071 A | 9/1997 | Wyrick |
| 5,688,251 A | 11/1997 | Chanoch |
| 5,695,472 A | 12/1997 | Wyrick |
| 5,704,911 A | 1/1998 | Parsons |
| 5,725,508 A | 3/1998 | Chanoch et al. |
| 5,730,723 A | 3/1998 | Castellano et al. |
| 5,743,889 A | 4/1998 | Sams |

(56) References Cited

U.S. PATENT DOCUMENTS

| | | |
|---|---|---|
| 5,769,138 A | 6/1998 | Sadowski et al. |
| 5,785,691 A | 7/1998 | Vetter et al. |
| 5,788,670 A | 8/1998 | Reinhard et al. |
| 5,801,057 A | 9/1998 | Smart et al. |
| 5,807,309 A | 9/1998 | Lundquist et al. |
| 5,820,602 A | 10/1998 | Kovelman et al. |
| 5,820,622 A | 10/1998 | Gross et al. |
| 5,827,232 A | 10/1998 | Chanoch et al. |
| 5,836,911 A | 11/1998 | Marzynski et al. |
| 5,843,036 A | 12/1998 | Olive et al. |
| 5,846,233 A | 12/1998 | Lilley et al. |
| 5,851,197 A | 12/1998 | Marano et al. |
| 5,851,198 A | 12/1998 | Castellano et al. |
| 5,860,456 A | 1/1999 | Bydlon et al. |
| 5,865,795 A | 2/1999 | Schiff et al. |
| 5,865,799 A | 2/1999 | Tanaka et al. |
| 5,868,711 A | 2/1999 | Kramer et al. |
| 5,873,857 A | 2/1999 | Kriesel |
| 5,875,976 A | 3/1999 | Nelson et al. |
| 5,879,327 A | 3/1999 | DeFarges et al. |
| 5,891,085 A | 4/1999 | Lilley et al. |
| 5,891,086 A | 4/1999 | Weston |
| 5,893,842 A | 4/1999 | Imbert |
| 5,919,159 A | 7/1999 | Lilley et al. |
| 5,921,966 A | 7/1999 | Bendek et al. |
| 5,925,017 A | 7/1999 | Kriesel et al. |
| 5,928,205 A | 7/1999 | Marshall |
| 5,935,949 A | 8/1999 | White |
| 5,951,528 A | 9/1999 | Parkin |
| 5,957,897 A | 9/1999 | Jeffrey |
| 5,960,797 A | 10/1999 | Kramer et al. |
| 5,989,227 A | 11/1999 | Vetter et al. |
| 6,004,297 A | 12/1999 | Steenfeldt-Jensen et al. |
| 6,045,534 A | 4/2000 | Jacobson et al. |
| 6,056,716 A | 5/2000 | D'Antonio et al. |
| 6,077,247 A | 6/2000 | Marshall et al. |
| 6,083,201 A | 7/2000 | Skinkle |
| 6,090,070 A | 7/2000 | Hager et al. |
| 6,099,504 A | 8/2000 | Gross et al. |
| 6,123,684 A | 9/2000 | Deboer et al. |
| 6,132,395 A | 10/2000 | Landau et al. |
| 6,159,181 A | 12/2000 | Crossman et al. |
| 6,171,276 B1 | 1/2001 | Lippe et al. |
| 6,203,529 B1 | 3/2001 | Gabriel et al. |
| 6,210,369 B1 | 4/2001 | Wilmot et al. |
| 6,221,046 B1 | 4/2001 | Burroughs et al. |
| 6,221,053 B1 | 4/2001 | Walters et al. |
| 6,223,408 B1 | 5/2001 | Vetter et al. |
| 6,231,540 B1 | 5/2001 | Smedegaard |
| 6,241,709 B1 | 6/2001 | Bechtold et al. |
| 6,245,347 B1 | 6/2001 | Zhang et al. |
| 6,258,078 B1 | 7/2001 | Thilly |
| 6,264,629 B1 | 7/2001 | Landau |
| 6,270,479 B1 | 8/2001 | Bergens et al. |
| 6,309,371 B1 | 10/2001 | Deboer et al. |
| 6,319,224 B1 | 11/2001 | Stout et al. |
| 6,371,939 B2 | 4/2002 | Bergens et al. |
| 6,383,168 B1 | 5/2002 | Landau et al. |
| 6,391,003 B1 | 5/2002 | Lesch, Jr. |
| 6,406,456 B1 | 6/2002 | Slate et al. |
| 6,428,528 B2 | 8/2002 | Sadowski et al. |
| 6,471,669 B2 | 10/2002 | Landau |
| 6,494,865 B1 | 12/2002 | Alchas |
| 6,517,517 B1 | 2/2003 | Farrugia et al. |
| 6,530,904 B1 | 3/2003 | Edwards et al. |
| 6,544,234 B1 | 4/2003 | Gabriel |
| 6,562,006 B1 | 5/2003 | Hjertman et al. |
| 6,565,553 B2 | 5/2003 | Sadowski et al. |
| 6,568,259 B2 | 5/2003 | Saheki et al. |
| 6,569,123 B2 | 5/2003 | Alchas et al. |
| 6,569,143 B2 | 5/2003 | Alchas et al. |
| 6,584,910 B1 | 7/2003 | Plass |
| 6,589,210 B1 | 7/2003 | Rolfe |
| 6,607,508 B2 | 8/2003 | Knauer |
| 6,620,137 B2 | 9/2003 | Kirchhofer et al. |
| 6,641,561 B1 | 11/2003 | Hill et al. |
| 6,645,170 B2 | 11/2003 | Landau |
| 6,656,150 B2 | 12/2003 | Hill et al. |
| 6,673,035 B1 | 1/2004 | Rice et al. |
| 6,682,504 B2 | 1/2004 | Nelson et al. |
| 6,689,092 B2 | 2/2004 | Zierenberg et al. |
| 6,706,000 B2 | 3/2004 | Perez et al. |
| 6,746,429 B2 | 6/2004 | Sadowski et al. |
| 6,767,336 B1 | 7/2004 | Kaplan |
| 6,805,686 B1 | 10/2004 | Fathallah et al. |
| 6,830,560 B1 | 12/2004 | Gross et al. |
| 6,899,698 B2 | 5/2005 | Sams |
| 6,932,793 B1 | 8/2005 | Marshall et al. |
| 6,932,794 B2 | 8/2005 | Giambattista et al. |
| 6,936,032 B1 | 8/2005 | Bush, Jr. et al. |
| 6,969,370 B2 | 11/2005 | Langley et al. |
| 6,969,372 B1 | 11/2005 | Halseth |
| 6,979,316 B1 | 12/2005 | Rubin et al. |
| 6,986,758 B2 | 1/2006 | Schiffmann |
| 6,997,901 B2 | 2/2006 | Popovsky |
| 7,018,364 B2 | 3/2006 | Giambattista et al. |
| 7,066,907 B2 | 6/2006 | Crossman et al. |
| 7,112,187 B2 | 9/2006 | Karlsson |
| 7,118,552 B2 | 10/2006 | Shaw et al. |
| 7,118,553 B2 | 10/2006 | Scherer |
| 7,138,389 B2 | 11/2006 | Amory et al. |
| 7,169,132 B2 | 1/2007 | Bendek et al. |
| 7,195,616 B2 | 3/2007 | Diller et al. |
| 7,218,962 B2 | 5/2007 | Freyman |
| 7,220,247 B2 | 5/2007 | Shaw et al. |
| 7,247,149 B2 | 7/2007 | Beyerlein |
| 7,291,132 B2 | 11/2007 | DeRuntz et al. |
| 7,292,885 B2 | 11/2007 | Scott et al. |
| 7,297,136 B2 | 11/2007 | Wyrick |
| 7,341,575 B2 | 3/2008 | Rice et al. |
| 7,361,160 B2 | 4/2008 | Hommann et al. |
| 7,390,314 B2 | 6/2008 | Stutz, Jr. et al. |
| 7,390,319 B2 | 6/2008 | Friedman |
| 7,407,492 B2 | 8/2008 | Gurtner |
| 7,416,540 B2 | 8/2008 | Edwards et al. |
| 7,442,185 B2 | 10/2008 | Amark et al. |
| 7,449,012 B2 | 11/2008 | Young et al. |
| 7,488,308 B2 | 2/2009 | Lesch, Jr. |
| 7,488,313 B2 | 2/2009 | Segal et al. |
| 7,488,314 B2 | 2/2009 | Segal et al. |
| 7,500,964 B2 | 3/2009 | Shaw et al. |
| 7,517,342 B2 | 4/2009 | Scott et al. |
| 7,519,418 B2 | 4/2009 | Scott et al. |
| 7,544,188 B2 | 6/2009 | Edwards et al. |
| 7,547,293 B2 | 6/2009 | Williamson et al. |
| 7,569,035 B1 | 8/2009 | Wilmot et al. |
| 7,611,491 B2 | 11/2009 | Pickhard |
| 7,621,887 B2 | 11/2009 | Griffiths et al. |
| 7,621,891 B2 | 11/2009 | Wyrick |
| 7,635,348 B2 | 12/2009 | Raven et al. |
| 7,635,350 B2 | 12/2009 | Scherer |
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Sema et al. |
| 7,658,724 B2 | 2/2010 | Rubin et al. |
| 7,670,314 B2 | 3/2010 | Wall et al. |
| 7,704,237 B2 | 4/2010 | Fisher et al. |
| 7,717,877 B2 | 5/2010 | Lavi et al. |
| 7,718,640 B2 | 5/2010 | Hubler et al. |
| 7,722,595 B2 | 5/2010 | Pettis et al. |
| 7,731,686 B2 | 6/2010 | Edwards et al. |
| 7,731,690 B2 | 6/2010 | Edwards et al. |
| 7,736,333 B2 | 6/2010 | Gillespie, III |
| 7,744,582 B2 | 6/2010 | Sadowski et al. |
| 7,749,194 B2 | 7/2010 | Edwards et al. |
| 7,749,195 B2 | 7/2010 | Hommann |
| 7,762,996 B2 | 7/2010 | Palasis |
| 7,776,015 B2 | 8/2010 | Sadowski et al. |
| 7,794,432 B2 | 9/2010 | Young et al. |
| 7,811,254 B2 | 10/2010 | Wilmot et al. |
| 7,862,543 B2 | 1/2011 | Potter et al. |
| 7,896,841 B2 | 3/2011 | Wall et al. |
| 7,901,377 B1 | 3/2011 | Harrison et al. |

(56) References Cited

U.S. PATENT DOCUMENTS

| | | |
|---|---|---|
| 7,905,352 B2 | 3/2011 | Wyrick |
| 7,905,866 B2 | 3/2011 | Haider et al. |
| 7,918,823 B2 | 4/2011 | Edwards et al. |
| 7,927,303 B2 | 4/2011 | Wyrick |
| 7,931,618 B2 | 4/2011 | Wyrick |
| 7,947,017 B2 | 5/2011 | Edwards et al. |
| RE42,463 E | 6/2011 | Landau |
| 7,955,304 B2 | 6/2011 | Guillermo |
| 7,967,772 B2 | 6/2011 | McKenzie et al. |
| 7,988,675 B2 | 8/2011 | Gillespie, III et al. |
| 8,016,774 B2 | 9/2011 | Freeman et al. |
| 8,016,788 B2 | 9/2011 | Edwards et al. |
| 8,021,335 B2 | 9/2011 | Lesch, Jr. |
| 8,048,035 B2 | 11/2011 | Mesa et al. |
| 8,048,037 B2 | 11/2011 | Kohlbrenner et al. |
| 8,057,427 B2 | 11/2011 | Griffiths et al. |
| 8,066,659 B2 | 11/2011 | Joshi et al. |
| 8,083,711 B2 | 12/2011 | Enggaard |
| 8,100,865 B2 | 1/2012 | Spofforth |
| 8,105,272 B2 | 1/2012 | Williamson et al. |
| 8,105,281 B2 | 1/2012 | Edwards et al. |
| 8,110,209 B2 | 2/2012 | Prestrelski et al. |
| 8,123,719 B2 | 2/2012 | Edwards et al. |
| 8,123,724 B2 | 2/2012 | Gillespie, III |
| 8,162,873 B2 | 4/2012 | Muto et al. |
| 8,162,886 B2 | 4/2012 | Sadowski et al. |
| 8,167,840 B2 | 5/2012 | Matusch |
| 8,167,866 B2 | 5/2012 | Klein |
| 8,177,758 B2 | 5/2012 | Brooks, Jr. et al. |
| 8,187,224 B2 | 5/2012 | Wyrick |
| 8,216,180 B2 | 7/2012 | Tschirren et al. |
| 8,216,192 B2 | 7/2012 | Burroughs et al. |
| 8,226,618 B2 | 7/2012 | Geertsen |
| 8,226,631 B2 | 7/2012 | Boyd et al. |
| 8,233,135 B2 | 7/2012 | Jansen et al. |
| 8,235,952 B2 | 8/2012 | Wikner |
| 8,246,577 B2 | 8/2012 | Schrul et al. |
| 8,251,947 B2 | 8/2012 | Kramer et al. |
| 8,257,318 B2 | 9/2012 | Thogersen et al. |
| 8,257,319 B2 | 9/2012 | Plumptre |
| 8,267,899 B2 | 9/2012 | Moller |
| 8,267,900 B2 | 9/2012 | Harms et al. |
| 8,273,798 B2 | 9/2012 | Bausch et al. |
| 8,275,454 B2 | 9/2012 | Adachi et al. |
| 8,276,583 B2 | 10/2012 | Farieta et al. |
| 8,277,412 B2 | 10/2012 | Kronestedt |
| 8,277,413 B2 | 10/2012 | Kirchhofer |
| 8,298,175 B2 | 10/2012 | Hirschel et al. |
| 8,298,194 B2 | 10/2012 | Moller |
| 8,300,852 B2 | 10/2012 | Terada |
| RE43,834 E | 11/2012 | Steenfeldt-Jensen et al. |
| 8,308,232 B2 | 11/2012 | Zamperla et al. |
| 8,308,695 B2 | 11/2012 | Laiosa |
| 8,313,466 B2 | 11/2012 | Edwards et al. |
| 8,317,757 B2 | 11/2012 | Plumptre |
| 8,323,237 B2 | 12/2012 | Radmer et al. |
| 8,333,739 B2 | 12/2012 | Moller |
| 8,337,472 B2 | 12/2012 | Edginton et al. |
| 8,343,103 B2 | 1/2013 | Moser |
| 8,343,109 B2 | 1/2013 | Marshall et al. |
| 8,348,905 B2 | 1/2013 | Radmer et al. |
| 8,353,878 B2 | 1/2013 | Moller et al. |
| 8,357,120 B2 | 1/2013 | Moller et al. |
| 8,357,125 B2 | 1/2013 | Grunhut et al. |
| 8,361,036 B2 | 1/2013 | Moller et al. |
| 8,366,680 B2 | 2/2013 | Raab |
| 8,372,031 B2 | 2/2013 | Elmen et al. |
| 8,372,042 B2 | 2/2013 | Wieselblad |
| 8,376,993 B2 | 2/2013 | Cox et al. |
| 8,398,593 B2 | 3/2013 | Eich et al. |
| 8,409,149 B2 | 4/2013 | Hommann et al. |
| 8,435,215 B2 | 5/2013 | Arby et al. |
| 2001/0039394 A1 | 11/2001 | Weston |
| 2001/0049496 A1 | 12/2001 | Kirchhofer et al. |
| 2002/0007149 A1 | 1/2002 | Nelson et al. |
| 2002/0045866 A1 | 4/2002 | Sadowski et al. |
| 2002/0173752 A1 | 11/2002 | Polzin |
| 2002/0183690 A1 | 12/2002 | Arnisolle |
| 2002/0188251 A1 | 12/2002 | Staylor et al. |
| 2003/0040697 A1 | 2/2003 | Pass et al. |
| 2003/0083621 A1 | 5/2003 | Shaw et al. |
| 2003/0105430 A1 | 6/2003 | Lavi et al. |
| 2003/0130619 A1 | 7/2003 | Safabash et al. |
| 2003/0158523 A1 | 8/2003 | Hjertman et al. |
| 2003/0171717 A1 | 9/2003 | Farrugia et al. |
| 2003/0229330 A1 | 12/2003 | Hickle |
| 2003/0236502 A1 | 12/2003 | De La Serna et al. |
| 2004/0039336 A1 | 2/2004 | Amark et al. |
| 2004/0039337 A1 | 2/2004 | Letzing |
| 2004/0097783 A1 | 5/2004 | Peters et al. |
| 2004/0097883 A1 | 5/2004 | Roe |
| 2004/0143213 A1 | 7/2004 | Hunter et al. |
| 2004/0191225 A1 | 9/2004 | Dinsmore et al. |
| 2004/0220524 A1 | 11/2004 | Sadowski et al. |
| 2004/0267207 A1 | 12/2004 | Veasey et al. |
| 2004/0267355 A1 | 12/2004 | Scott et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0080377 A1 | 4/2005 | Sadowski et al. |
| 2005/0101919 A1 | 5/2005 | Brunnberg |
| 2005/0165360 A1 | 7/2005 | Stamp |
| 2005/0165363 A1 | 7/2005 | Judson et al. |
| 2005/0209569 A1 | 9/2005 | Ishikawa et al. |
| 2005/0215955 A1 | 9/2005 | Slawson |
| 2005/0240145 A1 | 10/2005 | Scott et al. |
| 2005/0256499 A1 | 11/2005 | Pettis et al. |
| 2005/0261634 A1 | 11/2005 | Karlsson |
| 2005/0273054 A1 | 12/2005 | Asch |
| 2006/0025747 A1 | 2/2006 | Sullivan et al. |
| 2006/0106362 A1 | 5/2006 | Pass et al. |
| 2006/0129122 A1 | 6/2006 | Wyrick |
| 2006/0224124 A1 | 10/2006 | Scherer |
| 2006/0258988 A1 | 11/2006 | Keitel et al. |
| 2006/0258990 A1 | 11/2006 | Weber |
| 2007/0017533 A1 | 1/2007 | Wyrick |
| 2007/0025890 A1 | 2/2007 | Joshi et al. |
| 2007/0027430 A1 | 2/2007 | Hommann |
| 2007/0077286 A1 | 4/2007 | Shihara et al. |
| 2007/0088288 A1 | 4/2007 | Barron et al. |
| 2007/0093775 A1 | 4/2007 | Daly |
| 2007/0100288 A1 | 5/2007 | Bozeman et al. |
| 2007/0123818 A1 | 5/2007 | Griffiths et al. |
| 2007/0123829 A1 | 5/2007 | Atterbury et al. |
| 2007/0129686 A1 | 6/2007 | Daily et al. |
| 2007/0129687 A1 | 6/2007 | Marshall et al. |
| 2007/0185432 A1 | 8/2007 | Etheredge et al. |
| 2007/0191784 A1 | 8/2007 | Jacobs et al. |
| 2007/0219498 A1 | 9/2007 | Malone et al. |
| 2008/0008762 A1* | 1/2008 | Robinson ............. A61K 9/0048 424/489 |
| 2008/0059133 A1 | 3/2008 | Edwards et al. |
| 2008/0154199 A1 | 6/2008 | Wyrick |
| 2008/0154200 A1 | 6/2008 | Lesch |
| 2008/0185069 A1 | 8/2008 | Clark |
| 2008/0262427 A1 | 10/2008 | Hommann |
| 2008/0262436 A1 | 10/2008 | Olson |
| 2008/0262445 A1 | 10/2008 | Hsu et al. |
| 2008/0275013 A1 | 11/2008 | Gyurik |
| 2009/0124981 A1 | 5/2009 | Evans |
| 2009/0124997 A1 | 5/2009 | Pettis et al. |
| 2009/0204062 A1 | 8/2009 | Muto et al. |
| 2009/0254027 A1 | 10/2009 | Moller |
| 2009/0254035 A1 | 10/2009 | Kohlbrenner et al. |
| 2009/0292240 A1 | 11/2009 | Kramer et al. |
| 2009/0299278 A1 | 12/2009 | Lesch, Jr. et al. |
| 2009/0304812 A1 | 12/2009 | Stainforth et al. |
| 2009/0312705 A1 | 12/2009 | Grunhut |
| 2009/0318361 A1 | 12/2009 | Noera et al. |
| 2010/0016326 A1 | 1/2010 | Will |
| 2010/0036318 A1 | 2/2010 | Raday et al. |
| 2010/0049125 A1 | 2/2010 | James et al. |
| 2010/0069845 A1 | 3/2010 | Marshall et al. |
| 2010/0076378 A1 | 3/2010 | Runfola |

(56) References Cited

U.S. PATENT DOCUMENTS

| | | |
|---|---|---|
| 2010/0076400 A1 | 3/2010 | Wall |
| 2010/0087847 A1 | 4/2010 | Hong |
| 2010/0094214 A1 | 4/2010 | Abry et al. |
| 2010/0094324 A1 | 4/2010 | Huang et al. |
| 2010/0100039 A1 | 4/2010 | Wyrick |
| 2010/0114058 A1 | 5/2010 | Weitzel et al. |
| 2010/0121272 A1 | 5/2010 | Marshall et al. |
| 2010/0137798 A1 | 6/2010 | Streit et al. |
| 2010/0152699 A1 | 6/2010 | Ferrari et al. |
| 2010/0152702 A1 | 6/2010 | Vigil et al. |
| 2010/0160894 A1 | 6/2010 | Julian et al. |
| 2010/0168677 A1 | 7/2010 | Gabriel et al. |
| 2010/0174268 A1 | 7/2010 | Wilmot et al. |
| 2010/0191217 A1 | 7/2010 | Hommann et al. |
| 2010/0204678 A1 | 8/2010 | Imran |
| 2010/0217105 A1 | 8/2010 | Yodfat et al. |
| 2010/0228193 A1 | 9/2010 | Wyrick |
| 2010/0249746 A1 | 9/2010 | Klein |
| 2010/0256570 A1 | 10/2010 | Maritan |
| 2010/0258631 A1 | 10/2010 | Rueblinger et al. |
| 2010/0262082 A1 | 10/2010 | Brooks et al. |
| 2010/0262083 A1 | 10/2010 | Grunhut et al. |
| 2010/0268170 A1 | 10/2010 | Carrel et al. |
| 2010/0274198 A1 | 10/2010 | Bechtold |
| 2010/0274273 A1 | 10/2010 | Schraga et al. |
| 2010/0288593 A1 | 11/2010 | Chiesa et al. |
| 2010/0292643 A1 | 11/2010 | Wilmot et al. |
| 2010/0292653 A1 | 11/2010 | Maritan |
| 2010/0298780 A1 | 11/2010 | Laiosa |
| 2010/0312196 A1 | 12/2010 | Hirschel et al. |
| 2010/0318035 A1 | 12/2010 | Edwards et al. |
| 2010/0318037 A1 | 12/2010 | Young et al. |
| 2010/0324480 A1 | 12/2010 | Chun |
| 2011/0021989 A1 | 1/2011 | Janek et al. |
| 2011/0034879 A1 | 2/2011 | Crow |
| 2011/0054414 A1 | 3/2011 | Shang et al. |
| 2011/0077599 A1 | 3/2011 | Wozencroft |
| 2011/0087192 A1 | 4/2011 | Uhland et al. |
| 2011/0098655 A1 | 4/2011 | Jennings et al. |
| 2011/0098656 A1 | 4/2011 | Burnell et al. |
| 2011/0125076 A1 | 5/2011 | Kraft et al. |
| 2011/0125100 A1 | 5/2011 | Schwirtz et al. |
| 2011/0137246 A1 | 6/2011 | Cali et al. |
| 2011/0137247 A1 | 6/2011 | Mesa et al. |
| 2011/0144594 A1 | 6/2011 | Sund et al. |
| 2011/0190725 A1 | 8/2011 | Pettis et al. |
| 2011/0196300 A1 | 8/2011 | Edwards et al. |
| 2011/0196311 A1 | 8/2011 | Bicknell et al. |
| 2011/0224620 A1 | 9/2011 | Johansen et al. |
| 2011/0238003 A1 | 9/2011 | Bruno-Raimondi et al. |
| 2011/0269750 A1 | 11/2011 | Kley et al. |
| 2011/0319864 A1 | 12/2011 | Beller et al. |
| 2012/0004608 A1 | 1/2012 | Lesch, Jr. |
| 2012/0010529 A1 | 1/2012 | Chickering et al. |
| 2012/0016296 A1 | 1/2012 | Cleathero |
| 2012/0046609 A1 | 2/2012 | Mesa et al. |
| 2012/0053563 A1 | 3/2012 | Du |
| 2012/0059319 A1 | 3/2012 | Segal |
| 2012/0071829 A1 | 3/2012 | Edwards et al. |
| 2012/0095443 A1 | 4/2012 | Ferrari et al. |
| 2012/0101475 A1 | 4/2012 | Wilmot et al. |
| 2012/0116318 A1 | 5/2012 | Edwards et al. |
| 2012/0123350 A1 | 5/2012 | Giambattista et al. |
| 2012/0123385 A1 | 5/2012 | Edwards et al. |
| 2012/0130318 A1 | 5/2012 | Young |
| 2012/0130342 A1 | 5/2012 | Cleathero |
| 2012/0136303 A1 | 5/2012 | Cleathero |
| 2012/0136318 A1 | 5/2012 | Lanin et al. |
| 2012/0143144 A1 | 6/2012 | Young |
| 2012/0157931 A1 | 6/2012 | Nzike |
| 2012/0157965 A1 | 6/2012 | Wotton et al. |
| 2012/0172809 A1 | 7/2012 | Plumptre |
| 2012/0172811 A1 | 7/2012 | Enggaard et al. |
| 2012/0172812 A1 | 7/2012 | Plumptre et al. |
| 2012/0172813 A1 | 7/2012 | Plumptre et al. |
| 2012/0172814 A1 | 7/2012 | Plumptre et al. |
| 2012/0172815 A1 | 7/2012 | Holmqvist |
| 2012/0172816 A1 | 7/2012 | Boyd et al. |
| 2012/0172818 A1 | 7/2012 | Harms et al. |
| 2012/0172885 A1 | 7/2012 | Drapeau et al. |
| 2012/0179100 A1 | 7/2012 | Sadowski et al. |
| 2012/0179137 A1 | 7/2012 | Bartlett et al. |
| 2012/0184900 A1 | 7/2012 | Marshall et al. |
| 2012/0184917 A1 | 7/2012 | Bom et al. |
| 2012/0184918 A1 | 7/2012 | Bostrom |
| 2012/0186075 A1 | 7/2012 | Edginton |
| 2012/0191048 A1 | 7/2012 | Eaton |
| 2012/0191049 A1 | 7/2012 | Harms et al. |
| 2012/0197209 A1 | 8/2012 | Bicknell et al. |
| 2012/0197213 A1 | 8/2012 | Kohlbrenner et al. |
| 2012/0203184 A1 | 8/2012 | Selz et al. |
| 2012/0203185 A1 | 8/2012 | Kristensen et al. |
| 2012/0203186 A1 | 8/2012 | Vogt et al. |
| 2012/0209192 A1 | 8/2012 | Alexandersson |
| 2012/0209200 A1 | 8/2012 | Jones et al. |
| 2012/0209210 A1 | 8/2012 | Plumptre et al. |
| 2012/0209211 A1 | 8/2012 | Plumptre et al. |
| 2012/0209212 A1 | 8/2012 | Plumptre et al. |
| 2012/0215162 A1 | 8/2012 | Nielsen et al. |
| 2012/0215176 A1 | 8/2012 | Veasey et al. |
| 2012/0220929 A1 | 8/2012 | Nagel et al. |
| 2012/0220941 A1 | 8/2012 | Jones |
| 2012/0220953 A1 | 8/2012 | Holmqvist |
| 2012/0220954 A1 | 8/2012 | Cowe |
| 2012/0226226 A1 | 9/2012 | Edwards et al. |
| 2012/0230620 A1 | 9/2012 | Holdgate et al. |
| 2012/0232517 A1 | 9/2012 | Saiki |
| 2012/0245516 A1 | 9/2012 | Tschirren et al. |
| 2012/0245532 A1 | 9/2012 | Frantz et al. |
| 2012/0253274 A1 | 10/2012 | Karlsson et al. |
| 2012/0253287 A1 | 10/2012 | Giambattista et al. |
| 2012/0253288 A1 | 10/2012 | Dasbach et al. |
| 2012/0253289 A1 | 10/2012 | Cleathero |
| 2012/0253290 A1 | 10/2012 | Geertsen |
| 2012/0253314 A1 | 10/2012 | Harish et al. |
| 2012/0259285 A1 | 10/2012 | Schabbach et al. |
| 2012/0265153 A1 | 10/2012 | Jugl et al. |
| 2012/0267761 A1 | 10/2012 | Kim et al. |
| 2012/0271233 A1 | 10/2012 | Bruggemann et al. |
| 2012/0271243 A1 | 10/2012 | Plumptre et al. |
| 2012/0277724 A1 | 11/2012 | Larsen et al. |
| 2012/0283645 A1 | 11/2012 | Veasey et al. |
| 2012/0283648 A1 | 11/2012 | Veasey et al. |
| 2012/0283649 A1 | 11/2012 | Veasey et al. |
| 2012/0283650 A1 | 11/2012 | MacDonald et al. |
| 2012/0283651 A1 | 11/2012 | Veasey et al. |
| 2012/0283652 A1 | 11/2012 | MacDonald et al. |
| 2012/0283654 A1 | 11/2012 | MacDonald et al. |
| 2012/0283660 A1 | 11/2012 | Jones et al. |
| 2012/0283661 A1 | 11/2012 | Jugl et al. |
| 2012/0289907 A1 | 11/2012 | Veasey et al. |
| 2012/0289908 A1 | 11/2012 | Kouyoumjian et al. |
| 2012/0289909 A1 | 11/2012 | Raab et al. |
| 2012/0289929 A1 | 11/2012 | Boyd et al. |
| 2012/0291778 A1 | 11/2012 | Nagel et al. |
| 2012/0296276 A1 | 11/2012 | Nicholls et al. |
| 2012/0296287 A1 | 11/2012 | Veasey et al. |
| 2012/0302989 A1 | 11/2012 | Kramer et al. |
| 2012/0302992 A1 | 11/2012 | Brooks et al. |
| 2012/0310156 A1 | 12/2012 | Karlsson et al. |
| 2012/0310206 A1 | 12/2012 | Kouyoumjian et al. |
| 2012/0310208 A1 | 12/2012 | Kirchhofer |
| 2012/0310289 A1 | 12/2012 | Bottlang et al. |
| 2012/0316508 A1 | 12/2012 | Kirchhofer |
| 2012/0323177 A1 | 12/2012 | Adams et al. |
| 2012/0323186 A1 | 12/2012 | Karlsen et al. |
| 2012/0325865 A1 | 12/2012 | Forstreuter et al. |
| 2012/0330228 A1 | 12/2012 | Day et al. |
| 2013/0006191 A1 | 1/2013 | Jugl et al. |
| 2013/0006192 A1 | 1/2013 | Teucher et al. |
| 2013/0006193 A1 | 1/2013 | Veasey et al. |
| 2013/0006310 A1 | 1/2013 | Bottlang et al. |
| 2013/0012871 A1 | 1/2013 | Pommereu |
| 2013/0012884 A1 | 1/2013 | Pommerau et al. |

(56) References Cited

U.S. PATENT DOCUMENTS

| | | | |
|---|---|---|---|
| 2013/0012885 A1 | 1/2013 | Bode et al. |
| 2013/0018310 A1 | 1/2013 | Boyd et al. |
| 2013/0018313 A1 | 1/2013 | Kramer et al. |
| 2013/0018317 A1 | 1/2013 | Bobroff et al. |
| 2013/0018323 A1 | 1/2013 | Boyd et al. |
| 2013/0018327 A1 | 1/2013 | Dasbach et al. |
| 2013/0018328 A1 | 1/2013 | Jugl et al. |
| 2013/0023830 A1 | 1/2013 | Bode |
| 2013/0030367 A1 | 1/2013 | Wotton et al. |
| 2013/0030378 A1 | 1/2013 | Jugl et al. |
| 2013/0030383 A1 | 1/2013 | Keitel |
| 2013/0030409 A1 | 1/2013 | Macdonald et al. |
| 2013/0035641 A1 | 2/2013 | Moller et al. |
| 2013/0035642 A1 | 2/2013 | Daniel |
| 2013/0035644 A1 | 2/2013 | Giambattista et al. |
| 2013/0035645 A1 | 2/2013 | Bicknell et al. |
| 2013/0035647 A1 | 2/2013 | Veasey et al. |
| 2013/0041321 A1 | 2/2013 | Cross et al. |
| 2013/0041324 A1 | 2/2013 | Daniel |
| 2013/0041325 A1 | 2/2013 | Helmer et al. |
| 2013/0041327 A1 | 2/2013 | Daniel |
| 2013/0041328 A1 | 2/2013 | Daniel |
| 2013/0041347 A1 | 2/2013 | Daniel |
| 2013/0060231 A1 | 3/2013 | Adlon et al. |

FOREIGN PATENT DOCUMENTS

| | | |
|---|---|---|
| AU | 2007253481 | 11/2007 |
| AU | 2007301890 | 4/2008 |
| AU | 2008231897 | 10/2008 |
| AU | 2008309660 | 4/2009 |
| AU | 2009217376 | 10/2009 |
| AU | 2009272992 | 1/2010 |
| AU | 2009299888 | 4/2010 |
| AU | 2009326132 | 8/2011 |
| AU | 2009326321 | 8/2011 |
| AU | 2009326322 | 8/2011 |
| AU | 2009326323 | 8/2011 |
| AU | 2009326324 | 8/2011 |
| AU | 2009326325 | 8/2011 |
| AU | 2009341040 | 9/2011 |
| AU | 2010233924 | 11/2011 |
| AU | 2010239762 | 12/2011 |
| AU | 2010242096 | 12/2011 |
| AU | 2010254627 | 1/2012 |
| AU | 2010260568 | 2/2012 |
| AU | 2010260569 | 2/2012 |
| AU | 2010287033 | 4/2012 |
| AU | 2010303987 | 5/2012 |
| AU | 2010332857 | 7/2012 |
| AU | 2010332862 | 7/2012 |
| AU | 2010337136 | 7/2012 |
| AU | 2010338469 | 7/2012 |
| AU | 2010314315 | 8/2012 |
| AU | 2011212490 | 8/2012 |
| AU | 2011212556 | 8/2012 |
| AU | 2011212558 | 8/2012 |
| AU | 2011212561 | 8/2012 |
| AU | 2011212564 | 8/2012 |
| AU | 2011212566 | 8/2012 |
| AU | 2011212567 | 8/2012 |
| AU | 2011214922 | 8/2012 |
| AU | 2011221472 | 8/2012 |
| AU | 2011231688 | 9/2012 |
| AU | 2011231691 | 9/2012 |
| AU | 2011224884 | 10/2012 |
| AU | 2011231570 | 10/2012 |
| AU | 2011231697 | 10/2012 |
| AU | 2011233733 | 10/2012 |
| AU | 2011234479 | 10/2012 |
| AU | 2011238967 | 11/2012 |
| AU | 2011244232 | 11/2012 |
| AU | 2011244236 | 11/2012 |
| AU | 2011244237 | 11/2012 |
| AU | 2011249098 | 11/2012 |
| AU | 2011262408 | 12/2012 |
| AU | 2011270934 | 1/2013 |
| AU | 2011273721 | 1/2013 |
| AU | 2011273722 | 1/2013 |
| AU | 2011273723 | 1/2013 |
| AU | 2011273724 | 1/2013 |
| AU | 2011273725 | 1/2013 |
| AU | 2011273726 | 1/2013 |
| AU | 2011273727 | 1/2013 |
| AU | 2011273728 | 1/2013 |
| BR | 0208013 | 3/2004 |
| BR | 0308262 | 1/2005 |
| BR | PI712805 | 10/2012 |
| BR | PI0713802-4 | 11/2012 |
| BR | 0214721 | 12/2012 |
| CA | 2552177 | 7/1999 |
| CA | 2689022 | 11/2002 |
| CA | 2473371 | 7/2003 |
| CA | 2557897 | 10/2005 |
| CA | 02702412 | 12/2008 |
| CN | 101094700 | 12/2007 |
| CN | 101128231 | 2/2008 |
| CN | 101184520 | 5/2008 |
| CN | 101400394 | 4/2009 |
| CN | 101405582 | 4/2009 |
| CN | 101479000 | 7/2009 |
| CN | 101511410 | 8/2009 |
| CN | 101516421 | 8/2009 |
| CN | 101557849 | 10/2009 |
| CN | 101563123 | 10/2009 |
| CN | 101563124 | 10/2009 |
| CN | 101594898 | 12/2009 |
| CN | 101600468 | 12/2009 |
| CN | 101605569 | 12/2009 |
| CN | 101610804 | 12/2009 |
| CN | 101626796 | 1/2010 |
| CN | 101678166 | 3/2010 |
| CN | 101678172 | 3/2010 |
| CN | 101678173 | 3/2010 |
| CN | 101687078 | 3/2010 |
| CN | 101687079 | 3/2010 |
| CN | 101687080 | 3/2010 |
| CN | 101715371 | 5/2010 |
| CN | 101909673 | 12/2010 |
| CN | 101912650 | 12/2010 |
| CN | 101939034 | 1/2011 |
| CN | 101939036 | 1/2011 |
| CN | 102548599 | 7/2012 |
| CN | 102548601 | 7/2012 |
| CN | 102548602 | 7/2012 |
| CN | 102573955 | 7/2012 |
| CN | 102573958 | 7/2012 |
| CN | 102573960 | 7/2012 |
| CN | 102573963 | 7/2012 |
| CN | 102630172 | 8/2012 |
| CN | 102630173 | 8/2012 |
| CN | 102630174 | 8/2012 |
| CN | 102639170 | 8/2012 |
| CN | 102639171 | 8/2012 |
| CN | 102648014 | 8/2012 |
| CN | 102655899 | 9/2012 |
| CN | 102665800 | 9/2012 |
| CN | 102665802 | 9/2012 |
| CN | 102686255 | 9/2012 |
| CN | 102686256 | 9/2012 |
| CN | 102686258 | 9/2012 |
| CN | 102695531 | 9/2012 |
| CN | 102695532 | 9/2012 |
| CN | 102711878 | 10/2012 |
| CN | 102727965 | 10/2012 |
| CN | 102740907 | 10/2012 |
| CN | 102753222 | 10/2012 |
| CN | 102753223 | 10/2012 |
| CN | 102753224 | 10/2012 |
| CN | 102753227 | 10/2012 |
| CN | 102770170 | 11/2012 |
| CN | 102770173 | 11/2012 |
| CN | 102781499 | 11/2012 |
| CN | 102781500 | 11/2012 |

(56) References Cited

FOREIGN PATENT DOCUMENTS

| | | |
|---|---|---|
| CN | 102802699 | 11/2012 |
| CN | 102802702 | 11/2012 |
| CN | 102802703 | 11/2012 |
| CN | 102665801 | 12/2012 |
| CN | 102821801 | 12/2012 |
| CN | 102821802 | 12/2012 |
| CN | 102821805 | 12/2012 |
| CN | 102834133 | 12/2012 |
| CN | 102869399 | 1/2013 |
| CN | 102895718 | 1/2013 |
| CN | 102905613 | 1/2013 |
| CN | 102905742 | 1/2013 |
| CN | 102905743 | 1/2013 |
| CN | 102905744 | 1/2013 |
| CN | 102905745 | 1/2013 |
| CN | 102917738 | 2/2013 |
| CN | 102917743 | 2/2013 |
| DE | 102006041809 | 3/2008 |
| DE | 202011110155 | 12/2012 |
| DK | 1646844 | 12/2009 |
| DK | 2229201 | 7/2012 |
| DK | 2023082 | 10/2012 |
| DK | 2274032 | 10/2012 |
| DK | 02346552 | 11/2012 |
| DK | 1888148 | 1/2013 |
| DK | 2288400 | 1/2013 |
| DK | 2373361 | 1/2013 |
| DK | 1885414 | 2/2013 |
| DK | 2174682 | 2/2013 |
| DK | 2310073 | 2/2013 |
| EG | 25844 | 9/2012 |
| EP | 0072057 | 2/1983 |
| EP | 0103664 | 3/1984 |
| EP | 1752174 | 3/1986 |
| EP | 245895 | 11/1987 |
| EP | 255044 | 2/1988 |
| EP | 361668 | 4/1990 |
| EP | 0518416 | 12/1992 |
| EP | 525525 | 2/1993 |
| EP | 1067823 | 1/2001 |
| EP | 1161961 | 12/2001 |
| EP | 1307012 | 5/2003 |
| EP | 1457208 A1 | 9/2004 |
| EP | 1518575 | 3/2005 |
| EP | 1140260 | 8/2005 |
| EP | 1944050 | 7/2008 |
| EP | 2174682 | 4/2010 |
| EP | 2258424 | 12/2010 |
| EP | 2258425 | 12/2010 |
| EP | 02275158 | 1/2011 |
| EP | 2364742 | 9/2011 |
| EP | 2393062 | 12/2011 |
| EP | 2471564 | 7/2012 |
| EP | 02477681 | 7/2012 |
| EP | 02484395 | 8/2012 |
| EP | 2526987 | 11/2012 |
| EP | 02529773 | 12/2012 |
| EP | 02529774 | 12/2012 |
| EP | 02529775 | 12/2012 |
| EP | 2549789 | 1/2013 |
| ES | 02385630 | 7/2012 |
| ES | 2389866 | 11/2012 |
| ES | 2392667 | 12/2012 |
| ES | 02393173 | 12/2012 |
| ES | 2394556 | 2/2013 |
| FR | 2506161 | 11/1982 |
| FR | 2635009 | 2/1990 |
| GB | 6677523 | 8/1952 |
| GB | 1181037 | 2/1970 |
| GB | 1216813 | 12/1970 |
| GB | 2463034 | 3/2010 |
| IL | 171247 | 8/2012 |
| IL | 198750 | 10/2012 |
| JP | 10-507935 | 8/1998 |
| JP | 11-347121 | 12/1999 |
| JP | 2000-245839 | 9/2000 |
| JP | 2001-523485 | 11/2001 |
| JP | 2005-516737 | 6/2005 |
| JP | 5016490 | 5/2008 |
| JP | 2008-528126 | 7/2008 |
| JP | 5026411 | 11/2008 |
| JP | 5033792 | 11/2008 |
| JP | 5074397 | 2/2009 |
| JP | 2009-529395 | 8/2009 |
| JP | 5066177 | 9/2009 |
| JP | 5039135 | 11/2009 |
| JP | 5044625 | 12/2009 |
| JP | 2010-005414 | 1/2010 |
| JP | 2010-046507 | 3/2010 |
| JP | 2010-209102 | 9/2010 |
| JP | 4970282 | 7/2012 |
| JP | 4970286 | 7/2012 |
| JP | 4972147 | 7/2012 |
| JP | 4977209 | 7/2012 |
| JP | 4977252 | 7/2012 |
| JP | 4979686 | 7/2012 |
| JP | 4982722 | 7/2012 |
| JP | 2012515566 | 7/2012 |
| JP | 2012515585 | 7/2012 |
| JP | 2012515587 | 7/2012 |
| JP | 2012516168 | 7/2012 |
| JP | 2012516736 | 7/2012 |
| JP | 2012516737 | 7/2012 |
| JP | 4990151 | 8/2012 |
| JP | 4992147 | 8/2012 |
| JP | 4994370 | 8/2012 |
| JP | 5001001 | 8/2012 |
| JP | 2012143646 | 8/2012 |
| JP | 2012148198 | 8/2012 |
| JP | 2012519508 | 8/2012 |
| JP | 2012519511 | 8/2012 |
| JP | 2012519514 | 8/2012 |
| JP | 2012176295 | 9/2012 |
| JP | 2012183322 | 9/2012 |
| JP | 2012520128 | 9/2012 |
| JP | 2012521821 | 9/2012 |
| JP | 2012521825 | 9/2012 |
| JP | 2012521826 | 9/2012 |
| JP | 2012521827 | 9/2012 |
| JP | 2012521828 | 9/2012 |
| JP | 2012521829 | 9/2012 |
| JP | 2012521830 | 9/2012 |
| JP | 2012521831 | 9/2012 |
| JP | 2012521834 | 9/2012 |
| JP | 2012522547 | 9/2012 |
| JP | 2012-525172 | 10/2012 |
| JP | 2012-525180 | 10/2012 |
| JP | 2012-525185 | 10/2012 |
| JP | 2012523876 | 10/2012 |
| JP | 2012525200 | 10/2012 |
| JP | 5084825 | 11/2012 |
| JP | 2012232151 | 11/2012 |
| JP | 2012528618 | 11/2012 |
| JP | 2012528619 | 11/2012 |
| JP | 2012528620 | 11/2012 |
| JP | 2012528621 | 11/2012 |
| JP | 2012528622 | 11/2012 |
| JP | 2012528623 | 11/2012 |
| JP | 2012528624 | 11/2012 |
| JP | 2012528625 | 11/2012 |
| JP | 2012528626 | 11/2012 |
| JP | 2012528627 | 11/2012 |
| JP | 2012528628 | 11/2012 |
| JP | 2012528629 | 11/2012 |
| JP | 2012528630 | 11/2012 |
| JP | 2012528631 | 11/2012 |
| JP | 2012528632 | 11/2012 |
| JP | 2012528633 | 11/2012 |
| JP | 2012528634 | 11/2012 |
| JP | 2012528635 | 11/2012 |
| JP | 2012528636 | 11/2012 |
| JP | 2012528637 | 11/2012 |
| JP | 2012528638 | 11/2012 |
| JP | 2012528640 | 11/2012 |

(56) References Cited

FOREIGN PATENT DOCUMENTS

| | | |
|---|---|---|
| JP | 2012530576 | 12/2012 |
| JP | 2012532635 | 12/2012 |
| JP | 2012532636 | 12/2012 |
| JP | 2012532717 | 12/2012 |
| JP | 2012532720 | 12/2012 |
| JP | 2012532721 | 12/2012 |
| JP | 2012532722 | 12/2012 |
| JP | 5112330 | 1/2013 |
| JP | 5113847 | 1/2013 |
| KR | 101160735 | 7/2012 |
| KR | 20120091009 | 8/2012 |
| KR | 20120091153 | 8/2012 |
| KR | 20120091154 | 8/2012 |
| KR | 20120095919 | 8/2012 |
| KR | 20120099022 | 9/2012 |
| KR | 20120099101 | 9/2012 |
| KR | 20120102597 | 9/2012 |
| KR | 20120106754 | 9/2012 |
| KR | 20120106756 | 9/2012 |
| KR | 20120112503 | 10/2012 |
| MX | 2012006694 | 7/2012 |
| NO | 332622 | 10/2003 |
| NZ | 572765 | 8/2012 |
| NZ | 587235 | 8/2012 |
| NZ | 00590352 | 10/2012 |
| PL | 2023982 | 11/2012 |
| PT | 2274032 | 10/2012 |
| PT | 2346552 | 11/2012 |
| RU | 2462275 | 3/2011 |
| RU | 2459247 | 8/2012 |
| RU | 2011104496 | 8/2012 |
| RU | 2460546 | 9/2012 |
| RU | 2011109925 | 10/2012 |
| RU | 2011119019 | 11/2012 |
| SG | 181710 | 7/2012 |
| SG | 181790 | 7/2012 |
| SG | 184182 | 10/2012 |
| SG | 184328 | 11/2012 |
| SG | 184500 | 11/2012 |
| SG | 184501 | 11/2012 |
| SG | 184502 | 11/2012 |
| SI | 2274032 | 12/2012 |
| SI | 2346552 | 12/2012 |
| WO | WO 88/08724 | 11/1988 |
| WO | WO 91/13299 | 9/1991 |
| WO | WO 91/13430 | 9/1991 |
| WO | WO 92/19296 | 11/1992 |
| WO | WO 94/09839 | 5/1994 |
| WO | WO 94/11041 | 5/1994 |
| WO | WO 95/29720 | 11/1995 |
| WO | WO 95/29730 | 11/1995 |
| WO | WO 96/21482 | 7/1996 |
| WO | WO 97/14455 | 4/1997 |
| WO | WO 97/21457 | 6/1997 |
| WO | WO 1997/41907 | 11/1997 |
| WO | WO 97/48430 | 12/1997 |
| WO | WO 1998/031369 | 7/1998 |
| WO | WO 1998/032451 | 7/1998 |
| WO | WO 9831369 | 7/1998 |
| WO | WO 9832451 | 7/1998 |
| WO | WO 99/03521 | 1/1999 |
| WO | WO 99/10030 | 3/1999 |
| WO | WO 99/22790 | 5/1999 |
| WO | WO 9922789 | 5/1999 |
| WO | 9967271 A1 | 12/1999 |
| WO | WO 1999/062525 | 12/1999 |
| WO | WO 9962525 | 12/1999 |
| WO | WO 0006228 | 2/2000 |
| WO | WO 00/24441 | 5/2000 |
| WO | WO 00/29050 | 5/2000 |
| WO | WO 01/93926 | 12/2001 |
| WO | WO 02/083216 | 10/2002 |
| WO | WO 2002/089805 | 11/2002 |
| WO | WO 2089805 | 11/2002 |
| WO | WO 3047663 | 6/2003 |
| WO | 03065992 A2 | 8/2003 |
| WO | WO 2003/070296 | 8/2003 |
| WO | WO 3068290 | 8/2003 |
| WO | WO 03/070296 | 8/2003 |
| WO | WO 2003/097133 | 11/2003 |
| WO | WO 3097133 | 11/2003 |
| WO | WO 2004/028598 | 4/2004 |
| WO | WO 2004/041331 | 5/2004 |
| WO | WO 2004/047892 | 6/2004 |
| WO | WO 2004/108194 | 12/2004 |
| WO | WO 2005/002653 | 1/2005 |
| WO | WO 2005/005929 | 1/2005 |
| WO | WO 2005/009515 | 2/2005 |
| WO | WO 2005/053778 | 6/2005 |
| WO | WO 2006/079064 | 7/2006 |
| WO | WO 2006/086899 | 8/2006 |
| WO | WO 2006/125328 | 11/2006 |
| WO | WO 2006/130098 | 12/2006 |
| WO | WO 2007/047200 | 4/2007 |
| WO | WO 2007/063342 | 6/2007 |
| WO | WO 2007/100899 | 9/2007 |
| WO | WO 2006/079064 | 11/2007 |
| WO | WO 2007/129106 | 11/2007 |
| WO | WO 2007/131013 | 11/2007 |
| WO | WO 2007/131025 | 11/2007 |
| WO | WO 2007/143676 | 12/2007 |
| WO | WO 2008/005315 | 1/2008 |
| WO | WO 2008/009476 | 1/2008 |
| WO | WO 2008/058666 | 5/2008 |
| WO | WO 2008/089886 | 7/2008 |
| WO | WO 2008/100576 | 8/2008 |
| WO | WO 2008/107378 | 9/2008 |
| WO | WO 2008/112472 | 9/2008 |
| WO | WO 2007/104636 | 12/2008 |
| WO | WO 2009049885 | 4/2009 |
| WO | WO 2008/071804 | 8/2009 |
| WO | WO 2009/114542 | 9/2009 |
| WO | WO 2009/132778 | 11/2009 |
| WO | WO 2009/141005 | 11/2009 |
| WO | WO 2010/003569 | 1/2010 |
| WO | WO 2010/043533 | 4/2010 |
| WO | WO 2010/046394 | 4/2010 |
| WO | WO 2010/097116 | 9/2010 |
| WO | WO 2010/108116 | 9/2010 |
| WO | WO 2011/023736 | 3/2011 |
| WO | WO 2011/023882 | 3/2011 |
| WO | WO 2011/035877 | 3/2011 |
| WO | WO 2011/036133 | 3/2011 |
| WO | WO 2011/036134 | 3/2011 |
| WO | WO 2011/039163 | 4/2011 |
| WO | WO 2011/039201 | 4/2011 |
| WO | WO 2011/039202 | 4/2011 |
| WO | WO 2011/039207 | 4/2011 |
| WO | WO 2011/039208 | 4/2011 |
| WO | WO 2011/039209 | 4/2011 |
| WO | WO 2011/039211 | 4/2011 |
| WO | WO 2011/039216 | 4/2011 |
| WO | WO 2011/039217 | 4/2011 |
| WO | WO 2011/039218 | 4/2011 |
| WO | WO 2011/039219 | 4/2011 |
| WO | WO 2011/039228 | 4/2011 |
| WO | WO 2011/039231 | 4/2011 |
| WO | WO 2011/039232 | 4/2011 |
| WO | WO 2011/039233 | 4/2011 |
| WO | WO 2011/039236 | 4/2011 |
| WO | WO 2011/040861 | 4/2011 |
| WO | WO 2011/045385 | 4/2011 |
| WO | WO 2011/045386 | 4/2011 |
| WO | WO 2011/045611 | 4/2011 |
| WO | WO 2011/046756 | 4/2011 |
| WO | WO 2011/048223 | 4/2011 |
| WO | WO 2011/048422 | 4/2011 |
| WO | WO 2011/050359 | 4/2011 |
| WO | WO 2011/053225 | 5/2011 |
| WO | WO 2011/054648 | 5/2011 |
| WO | WO 2011/054775 | 5/2011 |
| WO | WO 2011/056127 | 5/2011 |
| WO | WO 2011/060087 | 5/2011 |
| WO | WO 2011/067187 | 6/2011 |

(56) References Cited

FOREIGN PATENT DOCUMENTS

| WO | WO 2011/067268 | 6/2011 |
|----|----------------|--------|
| WO | WO 2011/067320 | 6/2011 |
| WO | WO 2011/067615 | 6/2011 |
| WO | WO 2011/068253 | 6/2011 |
| WO | WO 2011/069936 | 6/2011 |
| WO | WO 2011/073302 | 6/2011 |
| WO | WO 2011/073307 | 6/2011 |
| WO | WO 2011/076280 | 6/2011 |
| WO | WO 2011/080092 | 7/2011 |
| WO | WO 2011/081867 | 7/2011 |
| WO | WO 2011/081885 | 7/2011 |
| WO | WO 2011/089206 | 7/2011 |
| WO | WO 2011/089207 | 7/2011 |
| WO | WO 2011/095478 | 8/2011 |
| WO | WO 2011/095480 | 8/2011 |
| WO | WO 2011/095483 | 8/2011 |
| WO | WO 2011/095486 | 8/2011 |
| WO | WO 2011/095488 | 8/2011 |
| WO | WO 2011/095489 | 8/2011 |
| WO | WO 2011/095503 | 8/2011 |
| WO | WO 2011/099918 | 8/2011 |
| WO | WO 2011/101349 | 8/2011 |
| WO | WO 2011/101351 | 8/2011 |
| WO | WO 2011/101375 | 8/2011 |
| WO | WO 2011/101376 | 8/2011 |
| WO | WO 2011/101377 | 8/2011 |
| WO | WO 2011/101378 | 8/2011 |
| WO | WO 2011/101379 | 8/2011 |
| WO | WO 2011/101380 | 8/2011 |
| WO | WO 2011/101381 | 8/2011 |
| WO | WO 2011/101382 | 8/2011 |
| WO | WO 2011/101383 | 8/2011 |
| WO | WO 2011/107805 | 9/2011 |
| WO | WO 2011/109205 | 9/2011 |
| WO | WO 2011/110464 | 9/2011 |
| WO | WO 2011/110465 | 9/2011 |
| WO | WO 2011/110466 | 9/2011 |
| WO | WO 2011/111006 | 9/2011 |
| WO | WO 2011/112136 | 9/2011 |
| WO | WO 2011/113806 | 9/2011 |
| WO | WO 2011/117212 | 9/2011 |
| WO | WO 2011/117284 | 9/2011 |
| WO | WO 2011/117404 | 9/2011 |
| WO | WO 2011/121003 | 10/2011 |
| WO | WO 2011/121061 | 10/2011 |
| WO | WO 2011/123024 | 10/2011 |
| WO | WO 2011/124634 | 10/2011 |
| WO | WO 2011/126439 | 10/2011 |
| WO | WO 2012020084 | 2/2012 |
| WO | WO 2012022771 | 2/2012 |
| WO | WO 2012/090186 | 7/2012 |
| WO | WO 2011/042537 | 8/2012 |
| WO | WO 2011/042540 | 8/2012 |
| WO | WO 2011/043714 | 8/2012 |
| WO | WO 2011/051366 | 9/2012 |
| WO | WO 2012/122643 | 9/2012 |

OTHER PUBLICATIONS

Supplementary Search Report and Written Opinion issued in counterpart European Application No. EP 13772839, dated Apr. 22, 2016.
Food and Drug Administration (FDA) Brief Package, Joint Meeting for Bone, Reproductive and Urologic Drugs Advisory Committee (BRUDAC) and the Drug Safety and Risk Management Advisory Committee (DSARM AC); Sep. 17, 2014.
International Patent Application No. PCT/US2013/035509, International Search Report, dated Aug. 27, 2013, 5 pages.
International Patent Application No. PCT/US2013/035509, International Written Opinion, dated Aug. 27, 2013, 13 pages.
"Skin", American Medical Association (AMA) Current Procedural Terminology, 1998, http://www.ama-assn.org/ama/pub/category/print/7176.html, 1 page.
Becks et al., "Comparison of Conventional Twice-Daily Subcutaneous Needle Injections to Multiple Jet Injections of Insulin in Insulin-Dependent Diabetes", Clinical and Investigative Medicine, 1981, p. 33B.
Binder, "Absorption of Injected Insulin", ACTA Pharmacological ET Toxicologica, 1969, 27(Supp 2), 3 pages.
Bonetti et al., "An Extended-Release formulation of Methotrexate for Subcutaneous Administration", Cancer Chemotherapy Pharmacology, 1994, 33, 303-306.
Braun et al., "Comparison of the Clinical Efficacy and Safety of Subcutaneous Versus Oral Administration of Methotrexate in Patients with Active Rheumatoid Arthritis", Arthritis and Rheumatism, Jan. 2008, 58(1), pp. 73-81.
Chen et al., "Blood Lipid Profiles and Peripheral Blood Mononuclear Cell Cholesterol Metabolism Gene Expression in Patients with and Without Methotrexate" BMC Medicine, 2011, 9(4), 9 pages.
Chiasson et al., "Continuous Subcutaneous Insulin Infusion (Mill-Hill Infuser) Versus Multiple Injections (Medi-Jector) in the Treatment of Insulin-Dependent Diabetes Mellitus and the Effects of Metabolic Control on Microangiopathy" Diabetes Care, Jul.-Aug. 1984, 7(4), pp. 331-337.
Cohn et al., "Clincal Experience with Jet Insulin Injection in Diabetes Mellitus Therapy: A Clue to the Pathogenesis of Lipodystrophy", Ala. J. Med. Sci., 1974, 11(3), pp. 265-272.
Cowie et al., "Physical and Metabolic Characteristics of Persons with Diabetes", National Institutes of Health/National Institute of Diabetes and Digestive and Kidney Diseases, 1995, 95(1468), pp. 117-120.
European Patent Application No. 03707823.5, Supplementary European Search Report, dated Mar. 30, 2005 with Communication dated Apr. 25, 2005 regarding Proceeding Further with the European Patent Application Pursuant to Article 96(1), and Rule 51(1) EPC, 3 pages.
European Patent Application No. 00976612.2, Communication Pursuant to Article 96(2) EPC, dated May 10, 2004, 5 pages.
Hingson et al., "A Survey of the Development of Jet Injection in Parenteral Therapy", Nov./Dec. 1952, 31(6), pp. 361-366.
Hoekstra et al., Bioavailability of Higher Dose Methotrexate Comparing Oral and Subcutaneous Administration i n Patients with Rheumatoid Arthritis, The Journal of Rheumatology, 2004, 31(4), pp. 645-648.
International Patent Application No. PCT/US2012/46742, International Search Report and Written Opinion dated Nov. 16, 2012, 11 pages.
International Patent Application No. PCT/US2009/052835, International Search Report dated Mar. 15, 2010, 5 pages.
International Patent Application No. PCT/US2013/029085, International Search Report dated May 13, 2013, 2 pages.
International Patent Application No. PCT/US2010/028011, International Search Report, dated Jun. 29, 2010, 5 pages.
International Patent Application No. PCT/US2009/036682, International Search Report, dated Jul. 7, 2009, 5 pages.
International Patent Application No. PCT/US2007/068010, International Search Report, dated Sep. 24, 2007, 3 pages.
International Patent Application No. PCT/US03/03917, International Search Report, dated Nov. 26, 2003, 1 page.
Jansen et al., Methotrexaat Buiten de Kliniek, Pharmaceutisch Weekblad, Nov. 1999, 134(46), pp. 1592-1596.
Japanese Patent Application No. 2007-552367, Office Action dated Apr. 9, 2011.
Katoulis et al., Efficacy of a New Needleless Insulin Delivery System Monitoring of Blood Glucose Fluctuations and Free Insulin Levels, The International Journal of Artificial Organs, 1989, 12(5), 333-339.
Kurnik et al., "Bioavailability of Oral vs. Subcutaneous low-dose Methotrexate in Patients with Crohn's Disease", Aliment Pharmacol Ther., Apr. 2003, 18, pp. 57-63.
Malone et al., "Comparison of Insulin Levels After Injection by Jet Stream and Disposable Insulin Syringe", Diabetes Care, Nov.-Dec. 1986, 9(6), 637-640.

(56) References Cited

OTHER PUBLICATIONS

"The Historical Development of Jet Injection and Envisioned Uses in Mass Immunization and Mass Therapy Based Upon Two Decades' Experience", Military Medicine, Jun. 1963, 128, pp. 516-524.
Pehling et al, "Comparison of Plasma Insulin Profiles After Subcutaneous Administration of Insulin by Jet Spray and Conventional Needle Injection in Patients with Insulin-Dependent Diabetes Mellitus", Mayo Clin. Proc., Nov. 1984, 59, pp. 751-754.
Reiss et al., "Atheroprotective Effects of Methotrexate on Reverse Cholesterol Transport Proteins and Foam Cell Transformation in Human THP-1 Monocyte/Macrophages", Arthritis and Rheumatism, Dec. 2008, 58(12), pp. 3675-3683.
Taylor et al., "Plasma Free Insulin Profiles After Administration of Insulin by Jet and Conventional Syringe Injection", Diabetes Care, May-Jun. 1981, 4(3), 337-339.
Weller et al., "Jet Injection of Insulin vs the Syringe-and-Needle Method", JAMA, Mar. 1966, 195(10), pp. 844-847.
Westlake et al., "The Effect of Methotrexate on Cardiovascular Disease in Patients with Rheumatoid Arthritis: A Systematic Literature Review", Rheumatology, Nov. 2009, 49, pp. 295-307.
Worth, "Jet Injection of Insulin: Comparison with Conventional Injection by Syringe and Needle", British Medical Journal, Sep. 1980, 281, pp. 713-714.
International Patent Application No. PCT/US20131029085, Written Opinion, dated May 13, 2013, 5 pages.
International Patent Application No. PCT/US2010/028011, Written Opinion, dated Jun. 29, 2010, 5 pages.
Zachheim et al., "Subcutaneous Administration of Methotrexate", Journal of the American Academy of Dermatology, 1992, 26(6), p. 1008.
Halle et al., "Twice-Daily Mixed Regular and NPH Insulin Injections with New Jet Injector Versus Conventional Syringes: Pharmacokinetics of Insulin Absorption", Diabetes Care, May-Jun. 1986 9(3), pp. 279-282.
International Patent Application No. PCT/US2012/046639, International Search Report and Written Opinion dated Apr. 22, 2013, 8 pages.
Glynn-Barnhart et al., "Pharmacotherapy: The Journal of Human Pharmacology and Drug Therapy", 1992, 12(5), abstract only, 2 pages.
Hamilton et al., "Why Intramuscular Methotrexate May be More Efficacious Than Oral Dosing in Patients with Rheumatoid Arthritis", British Journal of Rheumatology, 1997, 36(1), pp. 86-90.
Stamp et al., "Effects of Changing from Oral to Subcutaneous Methotrexate on Red Blood Cell Methotrexate Polyglutamate Concentrations and Disease Activity in Patients with Rheumatoid Arthritis", The Journal of Rheumatology, 2011, 38(12), 2540-2547.
Tukova et al., "Methotrexate Bioavailability after Oral and Subcutaneous Administration in Children with Juvenile Idiopathic Arthritis", Clinical and Experimental Rheumatology, 2009, 27, 1047-1053.
Wright et al., "Stability of Methotrexate Injection in Prefilled Plastic Disposable Syringes", International Journal of Pharmaceutics, Aug. 1988, 45(3), 237-244.
Lunenfeld, "Stable Testosterone Levels Achieved with Subcutaneous Testosterone Injections", The aging Male, Mar. 2006, 9(1), 70 pages.
International Patent Application No. PCT/US14/23883, International Search Report, dated Jul. 10, 2014, 3 pages.
International Patent Application No. PCT/US14/23485, International Search Report, dated Jul. 7, 2014, 2 pages.
International Patent Application No. PCT/US14/24530, International Search Report, dated Jul. 15, 2014, 2 pages.
International Patent Application No. PCT/US14/24543, International Search Report, dated Jul. 28, 2014, 2 pages.
Notification of Reasons for Refusal dated Feb. 15, 2017 for Japanese Patent Application No. 2015-504755.
English Translation of Notification of Reasons for Refusal dated Feb. 15, 2017 for Japanese Patent Application No. 2015-504755.
Official Action dated Oct. 24, 2016 for Canadian Patent Application No. 2,868,500, 3 pp.

\* cited by examiner

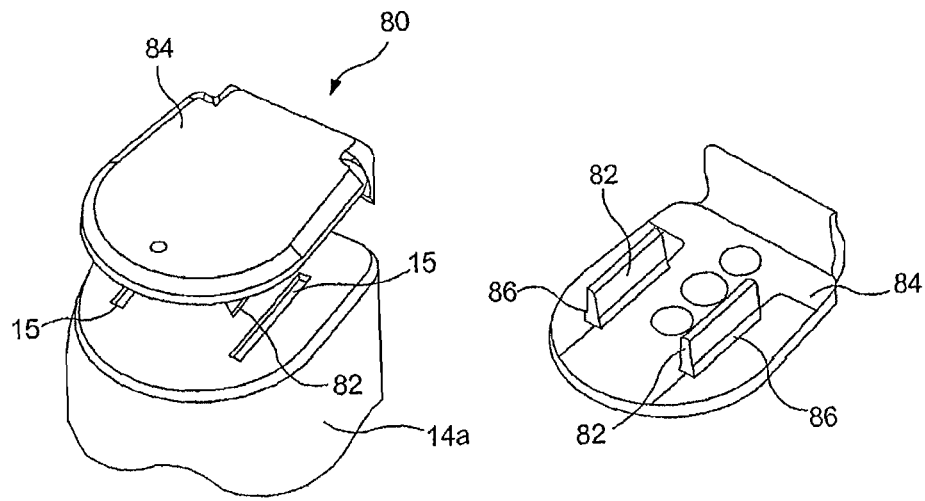
F I G. 4a          F I G. 4b
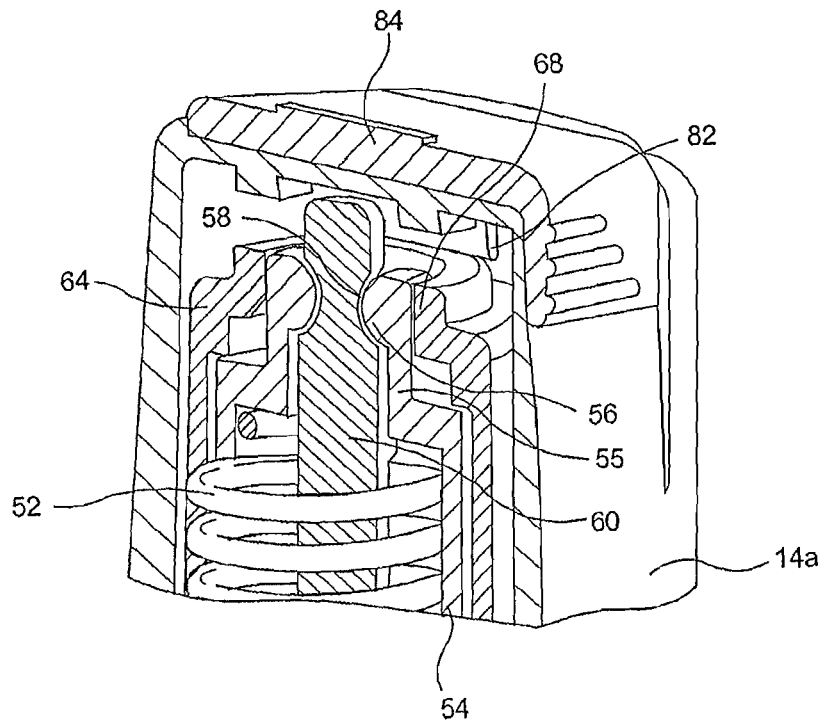
F I G. 5

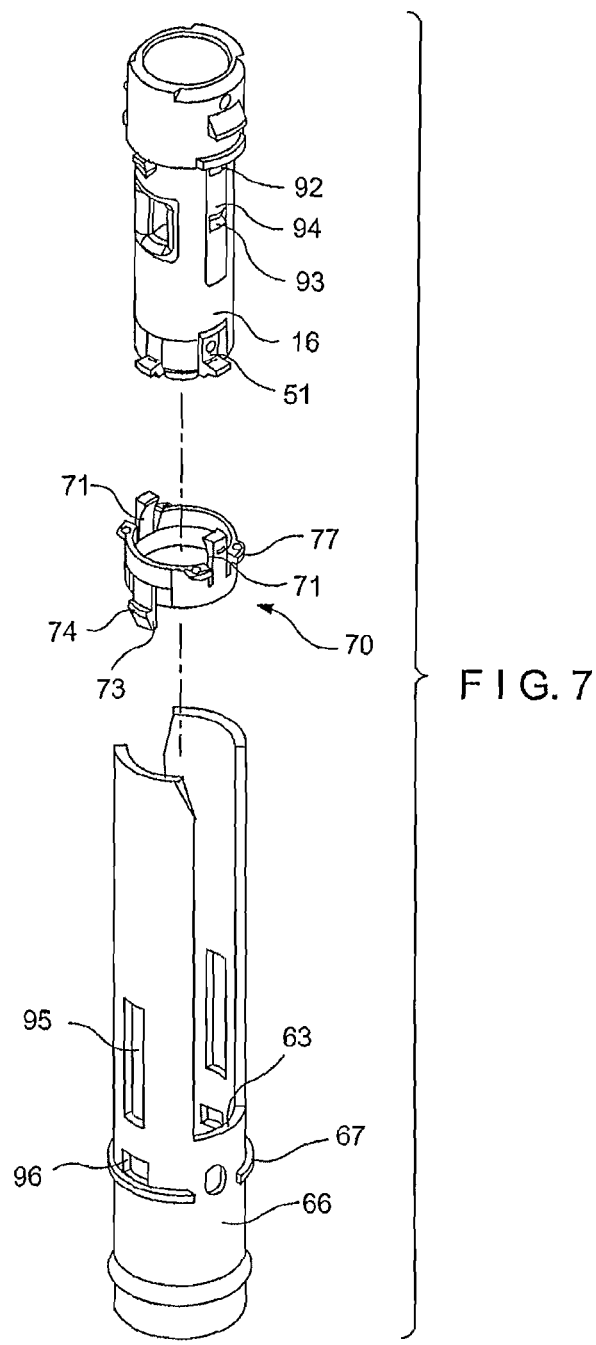
F I G. 7

| Mean Concentrations (ng/mL) of Testosterone in Mini-Pig Serum | | | | | | |
|---|---|---|---|---|---|---|
| | GROUP 1 | | | GROUP 2 | | |
| TIME (h) | Day 1 (autoinject) | SE (ng/mL) | Day 15 (needle/syr) | SE (ng/mL) | Day 1 (autoinject) | SE (ng/mL) | Day 15 (needle/syr) | SE (ng/mL) |
| 0.00 | NA | NA | NA | NA | NA | NA | 1.50 | 0.210 |
| 3.00 | 1.29 | 0.367 | 3.75 | 0.888 | NA | NA | 8.03 | 1.14 |
| 6.00 | 2.29 | 0.297 | 5.04 | 0.628 | 2.65 | 0.550 | 12.4 | 1.29 |
| 12.00 | 3.56 | 0.892 | 6.77 | 0.917 | 5.77 | 1.28 | 21.8 | 0.240 |
| 24.00 | 4.65 | 0.823 | 6.54 | 0.580 | 7.07 | 1.74 | 21.7 | 2.97 |
| 48.00 | 5.56 | 0.573 | 6.49 | 0.907 | 7.20 | 1.03 | 17.8 | 2.06 |
| 72.00 | 4.96 | 0.688 | 5.57 | 0.514 | 7.16 | 1.23 | 16.3 | 1.66 |
| 96.00 | 4.85 | 0.667 | 3.83 | 0.156 | 6.65 | 1.20 | 11.8 | 1.64 |
| 168.00 | 2.17 | 0.0764 | 1.74 | 0.297 | 3.58 | 0.688 | 6.61 | 1.02 |

| Mean PK Parameters | | GROUP 1 | | GROUP 2 | |
|---|---|---|---|---|---|
| AUC(0-x) | ng·h/mL | 679 | 81.4 | 975 | 165 |
| AUC(0-∞) | ng·h/mL | 891 | 63.2 | 1420 | 225 |
| %AUC Extrap | % | 24.3 | 4.41 | 31.5 | 5.62 |
| Cmax | ng/mL | 5.65 | 0.586 | 7.80 | 1.36 |
| tmax | h | 64.0 | 16.0 | 56.0 | 21.2 |
| t1/2 | h | 68.1 | 10.0 | 59.3 | 23.2 |

| | | GROUP 1 | | GROUP 2 | |
|---|---|---|---|---|---|
| AUC(0-x) | ng·h/mL | 735 | 13.5 | 2260 | 252 |
| AUC(0-∞) | ng·h/mL | 889 | 56.0 | 3010 | 423 |
| %AUC Extrap | % | 16.9 | 3.75 | 24.2 | 2.76 |
| Cmax | ng/mL | 7.81 | 0.0899 | 23.6 | 1.63 |
| tmax | h | 28.0 | 10.6 | 16.0 | 4.00 |
| t1/2 | h | 87.0 | 7.51 | 76.7 | 8.04 |

FIG. 13

NEEDLE ASSISTED JET INJECTION ADMINISTRATION OF TESTOSTERONE COMPOSITIONS

CROSS-REFERENCE TO RELATED APPLICATIONS

This application claims priority to U.S. Provisional Patent Application No. 61/621,298, filed Apr. 6, 2012, U.S. Provisional Patent Application No. 61/783,444, filed Mar. 14, 2013, U.S. Provisional Patent Application No. 61/763,395, filed Feb. 11, 2013, and U.S. Provisional Patent Application No. 61/776,283, filed Mar. 11, 2013, all of which are herein incorporated by reference.

BACKGROUND OF THE INVENTION

Testosterone is a steroid hormone from the androgen group. In general, androgens promote protein synthesis and growth of those tissues with androgen receptors. Testosterone is anabolic, meaning it builds up bone and muscle mass. Testosterone has the following structural formula:

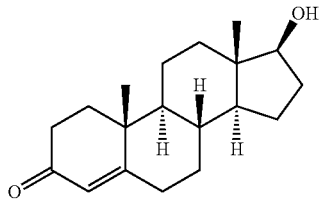

The original and primary use of testosterone is for the treatment of males who have too little or no natural endogenous testosterone production—males with hypogonadism. However, over the years, testosterone has also been given for many other conditions, e.g., reducing infertility, correcting lack of libido or erectile dysfunction, correcting osteoporosis, encouraging penile enlargement, encouraging height growth, encouraging bone marrow stimulation, reversing the effects of anemia and appetite stimulation.

There are several application methods for testosterone, including hypodermic injections and transdermal creams, gels and patches. However, hypodermic injections tend to be painful, inconvenient, and increase the risk of polycythemia. Transdermal creams, gels and patches are often expensive, cause acne and skin irritation at the site of administration, have poor compliance with daily administration, and fail to provide some patients with adequate testosterone levels.

Accordingly, an urgent need exists for methods of administering testosterone to provide benefits and improvements over conventional methods, e.g., hypodermic injections and transdermal creams, gels and patches, of administering testosterone to patients.

SUMMARY OF THE INVENTION

In one embodiment, the present invention includes an injection device, comprising a housing member having a distal end and a proximal end, a chamber disposed within the housing member configured to hold an amount of a preservative-free medicament comprising testosterone, a needle operatively associated with the chamber and having a length sufficient to deliver the medicament to an injection site at a depth below a patient's skin sufficient to minimize leak-back, a plunger movable within the chamber, and a force generating source capable of providing sufficient force on the plunger to eject at least a portion of the medicament from the chamber through the needle in less than about 20 seconds.

In another embodiment, the present invention includes a composition comprising testosterone enanthate and sesame oil, the testosterone enanthate being present at a concentration selected from the group consisting of about 50 mg/ml, about 75 mg/ml, about 100 mg/ml, about 125 mg/ml, about 150 mg/ml, about 175 mg/ml, about 200 mg/ml, about 225 mg/ml, and about 250 mg/ml.

In another embodiment, the present invention includes a composition comprising testosterone enanthate and sesame oil, the testosterone enanthate being present at a concentration selected from the group consisting of about 50 mg/ml, about 75 mg/ml, about 100 mg/ml, about 125 mg/ml, about 150 mg/ml, about 175 mg/ml, about 200 mg/ml, about 225 mg/ml, and about 250 mg/ml, wherein the composition is substantially free of testosterone enanthate precipitate.

In another embodiment, the present invention includes a method of administering testosterone comprising administering preservative-free composition comprising a unit dose of a testosterone or pharmaceutically acceptable ester or salt thereof in a pharmaceutically acceptable carrier subcutaneously to a mammal, wherein after administration, the plasma level of testosterone is maintained between about 200 ng/dl and about 1800 ng/dl for a Z1 time period.

In another embodiment, the present invention includes method of administering testosterone comprising administering a preservative-free composition comprising a unit dose of testosterone or pharmaceutically acceptable ester or salt thereof in a pharmaceutically acceptable carrier subcutaneously to a mammal, wherein after administration the plasma level of testosterone is maintained at a therapeutically effective level for a Z2 time period, (e.g., an extended period of time during treatment).

BRIEF DESCRIPTION OF THE DRAWINGS

These and other objects, features and advantages of the disclosure will be apparent from a consideration of the following non-limiting detailed description considered in conjunction with the drawing figures, in which:

FIGS. 4A and 4B are perspective views of a safety member used in connection with the injection device of FIG. 1;

FIG. 5 is an additional cross-sectional view of the device of FIG. 1 in the safety state;

FIG. 7 is an exploded view of an assembly of the needle guard, sleeve and locking ring associated with the injection device of FIG. 1;

FIG. 13 is a table illustrating the mean concentrations of testosterone in mini-pig serum;

Figure 1:
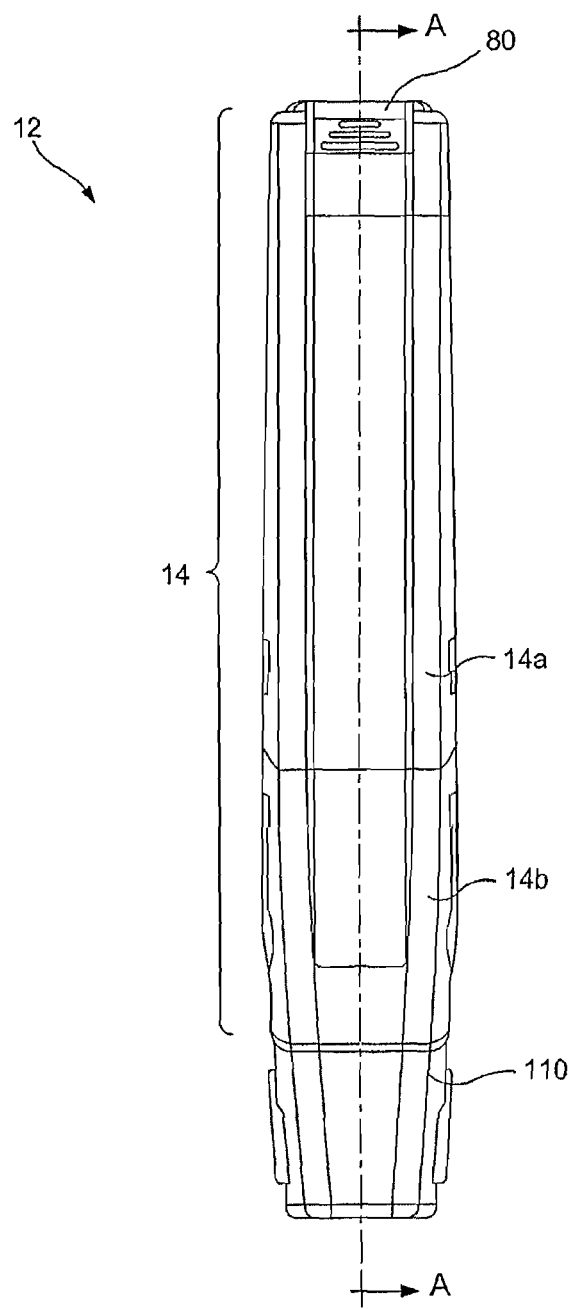
FIG. 1 is a side view of an injection device according to an embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF THE INVENTION

With reference to the accompanying drawings, various embodiments of the present invention are described more fully below. Some but not all embodiments of the present invention are explicitly shown. Indeed, various embodiments of the invention may be embodied in many different forms and should not be construed as limited to the embodiments expressly described. Like numbers refer to like elements throughout. The singular forms "a," "an," and "the" include the singular and plural unless the context clearly dictates otherwise.

A. Definitions

"Leak back", as the term is used herein, refers to the leakage of medicament out of an injection site during and/or after injection of a medicament.

"Substantially no leak back", as used herein refers an amount of leak back from an injection, the amount being less than about 0.05 ml or less than about 6% of the total volume or less than about 6% of the weight of the medicament. In an embodiment, "substantially no leak back" is an amount of leak back at or below an amount that cannot be readily detected by swiping a finger across the site of injection immediately after the injection has been completed. In an embodiment, "substantially no leak back" is an amount of leak back such that the therapeutic effect of testosterone administered by the injection is not materially altered. By way of non-limiting examples, the amount of leak back can be referenced in a liquid volume of a fluid composition having a specific concentration of testosterone, or the amount of leak back can be referred to in terms of amount of testosterone (e.g., mg testosterone) present in the total leak back volume or the number of injecting patients out of a population that experience leak back.

To "minimize leak back", as the term is used herein, is to inhibit or prevent the leak back associated with an injection of medicament, including but not limited to reducing the number of patients experiencing leak back associated with an injection A "preservative", as the term is used herein, refers to compounds known in the art to be used for the purpose of preserving a pharmaceutical composition, such as a medicament. As used herein, the preservative is purposefully used to aid in antimicrobial stability and thus possess antimicrobial activity. Substances not typically considered to be preservatives, or not typically used for preserving other compositions, are not encompassed by this definition.

"AUC" is the area under a curve representing the concentration of a compound, such as testosterone, or metabolite thereof in the blood or plasma or serum of a patient as a function of time following administration of the compound to the patient. For example, following administration of a testosterone as described herein, the AUC of the testosterone may be determined by measuring the concentration of it or its metabolite in blood using methods such as liquid chromatography-tandem mass spectrometry (LC-MS/MS), at various time intervals, and calculating the area under the blood, plasma or serum concentration-versus-time curve. The concentration versus time curve is sometime referred to as the pharmacokinetic profile. Suitable methods for calculating the AUC from a drug concentration-versus-time curve are well known in the art. Therefore, an AUC for testosterone may be determined by measuring the concentration of testosterone in the blood of a patient following administration of the testosterone to a patient.

"Bioavailability" refers to the amount of a compound, such as testosterone, that reaches the systemic circulation of a patient following administration of the compound to the patient and can be determined by evaluating, for example, the blood or plasma concentration for the compound.

"Bioequivalent," as the term is used herein, refers to one or more of confidence intervals of (a) the maximum concentration of a medicament (e.g., testosterone) in blood plasma of a patient following administration of a dose of the medicament to a patient ("Cmax") with an injector, (b) the time to reach the maximum concentration of the medicament in blood plasma of a patient following administration of a dose of the medicament to the patient with an injector ("Tmax"), and (c) area under the curve of the concentration of the medicament in blood plasma of a patient following administration of a dose of the medicament to the patient with the injector injected medicament ("AUC") falls between about 80% and about 125% of the measured confidence interval of the same medicament delivered by an alternative route.

"Patient" and "Subject" both independently include mammals, such as for example, humans.

"About" is understood to mean the range of + and −10% of the value referenced. However, use of "about" in reference to a value does not exclude the possibility of the referenced value alone. For example, "about 400" is understood to fully support both "400" as well as "360 to 440."

B. Compositions, Methods, and Embodiments of the Present Invention

The present disclosure encompasses injector embodiments and compositions and methods suitable for use alone or in combination with the injector embodiments.

I. Injectors

Typical hypodermic syringes utilize the force of one or more of a user's fingers pushing to deliver an injection. In some embodiments, powered injectors of the present disclosure are configured to help a subject repeatably and accurately and quickly administer a testosterone formulation to a preset depth at each injection without the need to utilize such pushing force.

In some embodiments, the powered injector includes an autoinjector, a needle-free jet injector, or a needle-assisted jet injector (collectively referred to as "injectors").

Known autoinjector embodiments of powered injectors use an energy source that produces moderate to low pressure in the medicament chamber so that a medicament contained in the medicament chamber is fired at a slow speed, similar to the pressure and speed from a finger-driven syringe. In contrast, autoinjector embodiments of the powered injectors of the present disclosure use an energy source that produces moderate to high pressure in the medicament chamber so that a medicament contained in the medicament chamber is fired at a fast speed and is completely injected into a subject in less than about 10 seconds. Other embodiments of the powered injectors are jet injectors, which can be needle-assisted or needle-free jet injectors. Jet injector embodiments can be configured to have an energy source selected to produce a high pressure in the medicament chamber to eject the medicament with sufficient pressure, force, and speed to exit the injector as a fluid jet. As described in greater detail below, whereas a medicament injected into a subject via an autoinjector or hypodermic syringe is delivered in a bolus typically near the needle tip such that leak back can occur, the medicament delivered from a jet injector is sprayed rapidly into the tissue, typically remotely from the needle tip, and typically does not deposit the medicament in a bolus local to a needle tip such that leak back is minimized Needle-free jet injectors use sufficient pressure and injection speed so that the fluid jet breaks through the outer layer of the skin, depositing the medicament thereunder. Needle-assisted jet injectors can use lower pressures than needle free jet injectors because they employ a needle to break through the outer part of the skin, but have pressures and speeds that are sufficiently high so that the medicament exits the needle tip as a fluid jet.

Some embodiments of the injectors disclosed herein are single-use or -dose injectors, configured to deliver in a single shot the entire volume of the agent(s) contained within a chamber of the injector or within a cartridge contained within the injector. In other embodiments, the injectors are configured to inject only a portion of the contents of the injector or a cartridge within the injector and can use dosage-setting mechanisms to enable the selection of the volume of injection to be delivered in one shot, or other mechanisms to provide an adjustable dosage. In each of the foregoing embodiments, the injector can be pre-filled, or configured to receive a cartridge that has the dosage of medicament. Alternative embodiments are configured to be fillable as known in the art.

Injectors provided by the present disclosure may be utilized by patients to self-inject testosterone formulations. Various aspects of the present disclosure relate to self-injection of testosterone formulations by a subject without the aid of a health care provider. In certain embodiments, the injectors use a needle to inject testosterone formulations into a target tissue of a subject, such as autoinjector or needle-assisted jet injector embodiments, while other embodiments are needle-free injectors and thus do not require a needle to inject testosterone formulations into a target tissue of a subject. In certain embodiments, the injectors may utilize pressure sufficient to deliver testosterone formulations completely and quickly. In certain embodiments, the injectors may utilize sufficiently high pressure to deliver one or more testosterone formulations completely and quickly in a fluid jet.

In some embodiments, powered injectors provided by the present disclosure do not require any priming or preparatory step in order to place them in condition to deliver an injection, thereby reducing or eliminating exposure of the testosterone formulation to the air and/or premature expulsion of the testosterone formulation from a needle of the injector prior to the delivery shot. Therefore, the risk of contact with the testosterone formulation contained in the injector, by the subject or by a non-user of the injectors, is reduced or eliminated.

A suitable injector for use with the present invention includes the injector shown in application Ser. No. 61/763,395 entitled "Needle Assisted Jet Injector Device Having Reduced Trigger Force" and Ser. No. 61/776,283 entitled "Needle Assisted Jet Injector Device Having Reduced Trigger Force", the contents of each which are hereby incorporated by reference in their entirety.

Referring to FIGS. 1-5, an embodiment of an injector according to an embodiment of the present disclosure is presented. The embodiment shown in these figures is a needle injector, and depending on the spring used and delivery conduit, including the needle and injection outlet, can be configured as an autoinjector or a needle-assisted jet injector. The depicted injector 12 has an outer housing member 14 configured for allowing a user to handle the injector 12 and that substantially houses most of the components shown in FIG. 2. In some embodiments, outer housing 14 is formed from two mating portions 14a, 14b that can be configured to attach to one another by a snap or press fit or by using adhesives, welding or the like. Housing 14 includes a medicament chamber 22 therein that is configured for storing and dispensing one or more liquid medicaments, such as, for example, a testosterone formulation. In the embodiment shown in FIG. 2, medicament chamber 22 is formed in a prefilled syringe 18 that fits within housing 14, but other types of fluid chambers can be used, including known types of cartridges that can be prefilled, refillable, or the like with the medicament(s). Additionally, medicament chamber 22 can be integrally formed within housing 14.

In an embodiment, a stopper portion of a prefilled syringe, or other portion of the prefilled syringe designed to assist in containing the medicament contained within the prefilled syringe, is made of a material that is chemically resistant to one or more constituents contained in the prefilled syringe. In an embodiment, a suitable stopper has minimized or reduced leachable or extractable material and/or is resistant to one or more of acids, bases, hydrocarbons, oils, lipids, carbohydrates, or oxygen. Non-limiting examples of suitable stoppers include physically-modified rubber, chemically-modified rubber, teflon, and teflon-coated materials. In an embodiment, a stopper is comprised of any material that enhances the stability of the stopper and/or its function for the containment of an oil-based composition, and in particular, when compared to the function of a standard rubber stopper used to contain the same oil-based composition.

In the embodiment shown, a safety member 80 is located on the proximal end of outer housing 14 and is removably affixed thereto by a plurality of tabs that extend through matching openings formed in outer housing 14 to form a press-fit between safety member 80 and outer housing 14. Safety member 80 is configured to prevent or reduce the likelihood of unintended firing of the injection device during, for example, shipping or handling of injector 12. Safety member 80 can be removed by a user of injector 12 to allow for unrestricted use of injector 12. Alternative embodiments of the injectors can be constructed without safety member 80.

In a further embodiment, a sleeve 16 is housed within and mounted to the housing 14 and acts as a syringe support member. In some embodiments, the sleeve 16 is configured to hold and position a prefilled syringe 18, carpule or other container of the type known in the art, such as, for example, a BD Hypak™ prefilled syringe (Becton, Dickinson and Company). One example of a suitable prefilled syringe for use in the depicted embodiments is one which is available in various sizes and volumes, such as the Becton Dickinson Hypak™. In some embodiments, the glass of the syringe body can be adhered to the needle. Using a prefilled syringe facilitates handling of the medicament when the injector is assembled, and there is an extensive body of knowledge of how the medicaments keep and behave in a prefilled syringe. In some embodiments, sleeve 16 is substantially fixed to the housing 12, such as by snaps, an adhesive, a weld, or another known attachment. The prefilled syringe 18 can have a container portion 20 that defines in its interior a medicament chamber 22, which is prefilled with an injectable medicament such as, for example, a testosterone formulation. In other embodiments, the medicament container and chamber are provided by other structures, such as a chamber that can be integral with or held in the housing, needle hub 32, or other injection outlet portion of the injector, for example. At the distal end of the prefilled syringe 18 is an injection-assisting needle 24. In certain embodiments, the length of needle 24 is less than 5 mm. In one embodiment, the length of needle 24 is greater than 5 mm. In one embodiment, the length of needle 24 is less than 10 mm. In one embodiment, the length of needle 24 is greater than 10 mm. In one embodiment, the length of needle 24 is less than 20 mm. In one embodiment, the length of needle 24 is greater than 20 mm. In other embodiments, the length of needle 24 is about 1 mm, about 2 mm, about 3 mm, about 4, about 5 mm, about 6 mm, about 7 mm, about 8 mm, about 9 mm, about 10 mm, or any range determinable from the preceding lengths (for example, about 4 mm to about 6 mm, or about 8 mm to about 10 mm). Needle 24 has an injecting tip 26 configured as known in the art to penetrate the tissue of a patient which, in some embodiments, is the skin. A needle bore extends through the needle 24, as known in the art. The bore is in fluid communication with the medicament in the medicament chamber 22 and is open at the needle tip 26 to inject the medicament.

At a proximal end of the medicament chamber 22, opposite from the needle 24, is a plunger 28 that seals the medicament in the medicament chamber 22. In some embodiments, a syringe wall comprises a tubular portion which, is closed at a distal end and open at a proximal end, to define the medicament chamber 22. Plunger 28 is slideably received in the tubular portion.

The prefilled syringe 18 is configured such that when the plunger 28 is displaced in a distal direction, the volume of the medicament chamber 22 is decreased, forcing the medicament out of the chamber 22 and through the bore of needle 24. At the distal end of the medicament chamber 22 is a needle hub portion 32 to which the needle is mounted. A syringe flange 35 extends radially from the proximal end of the syringe wall. In injector embodiments that use cartridges, carpules or other containers that define a chamber to contain the medicament, the needle can be fluidly connected with the chamber in a different manner, such as by connecting directly to the cartridge, carpule, or other container, or by connecting to another portion of the injector, such as a housing thereof, by a separate needle hub.

Figures 2, 3:
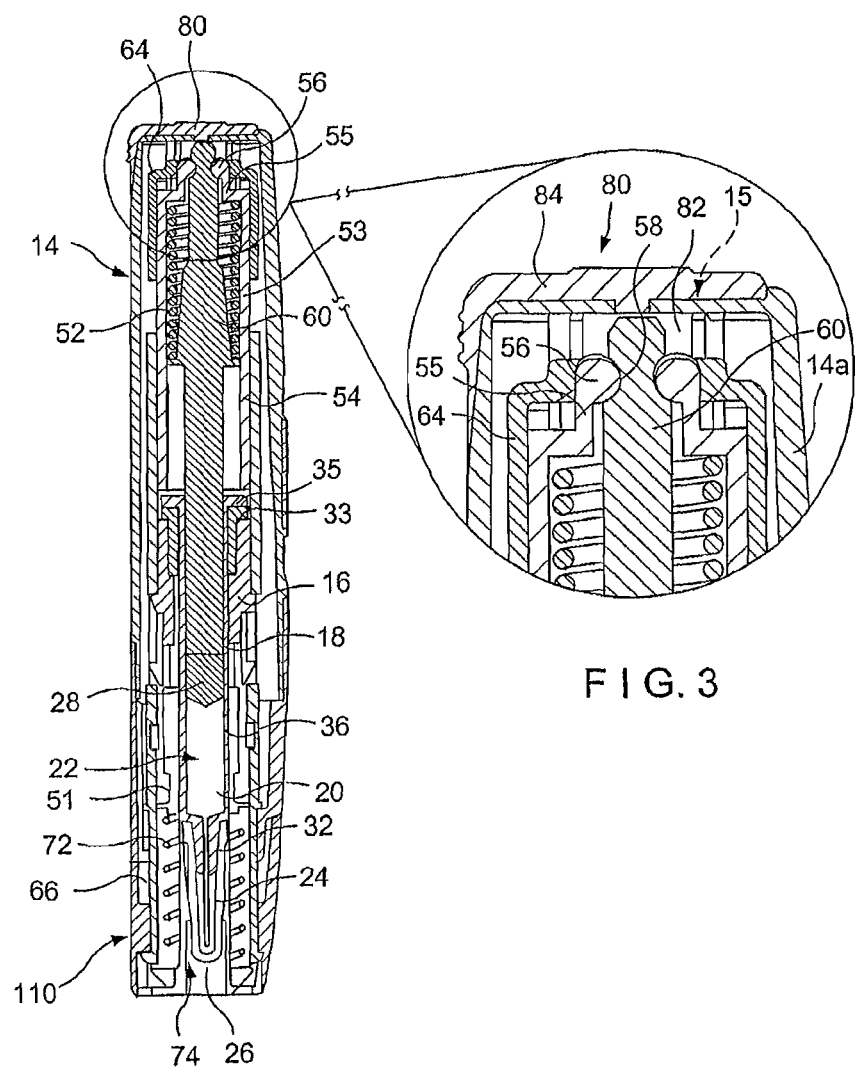
FIG. 2 is a cross-sectional view of the injection device of FIG. 1 in a safety state taken along line A-A.
FIG. 3 is an enlarged view of a portion of the cross-section shown in FIG. 2.

In the embodiment depicted in FIG. 2, the prefilled syringe 18 has a syringe body 36 wherein the flange 35, syringe wall, and hub portion 32 is of unitary construction. In some embodiments, the material comprising the syringe body 36 is glass, but other materials such as, for example, plastic or metal, can be used in other embodiments. To radially position the distal end of the prefilled syringe 18, in some embodiments sleeve 16 has a narrowed bore portion 51 that can be configured to abut the outside of the syringe wall. The narrowed bore portion 51 can be made of a resilient material, such as an elastomer, or it can be made unitarily with the rest of sleeve 16, such as by a series of radially-aligned, resiliently-flexible fingers. Additionally, the proximal portion of the syringe 18 can be held in place by a shock-absorbing device 33, which, in some embodiments, locates the proximal side of the syringe body 36 axially, and absorbs shocks from the impact of a sudden firing of the ram 60, such as in jet-injector embodiments, which produce elevated pressures in the medicament chamber 22 or container 20.

A trigger mechanism can also be housed within housing 14. In some embodiments, the trigger mechanism includes an inner housing 54 that can be attached to the outer housing 14, such as by snaps, an adhesive, a weld, or other known attachment. Trigger protrusions 56 extend inwardly from the proximal end of the inner housing 54 and are resiliently biased outwardly. Trigger protrusions 56 are received in a recess 58 of ram 60 in blocking association therewith to prevent distal movement of the ram 60 prior to the firing of the device. The ram 60 is moved toward the distal end of the injector 10 by an energy source, which in some embodiments is a compression spring 52, although in other embodiments other suitable energy sources can be used such as elastomer or compressed-gas springs, or a gas generator. An example of a compression spring 52 suitable for use with injectors of the present disclosure is a coil spring. Alternative embodiments can also use other suitable trigger mechanisms as known in the art.

In one embodiment, the invention includes a cammed ram assembly as described in U.S. patent application Ser. No. 13/184,229, which is hereby incorporated by reference in its entirety.

A latch housing 64 can be provided exterior to the inner housing 54 to retain the trigger protrusions 56 in the blocking association in the recess 58 to hold ram 60 in the proximal position until firing is actuated. Latch 64 is slideable inside outer housing 14 with respect to the inner housing 54, in some embodiments in an axial direction, and in some embodiments latch 64 surrounds the inner housing 54. In some embodiments latch 64 is free to move relative to outer housing 14 and is only secured in place, after the removal of safety member 80, by the pressure exerted thereon by trigger protrusions 56. In several aspects, nothing is present that biases latch housing 54 away from the proximal end of outer housing 14, including springs or the like. Alternative embodiments can use a medicament container that is shuttled forward when the device is activated to pierce the skin with the needle, and some embodiments use trigger mechanisms that are activated by a button on another part of the injector, such as at the proximal end or on a side of the housing as known in the art.

Figure 6:
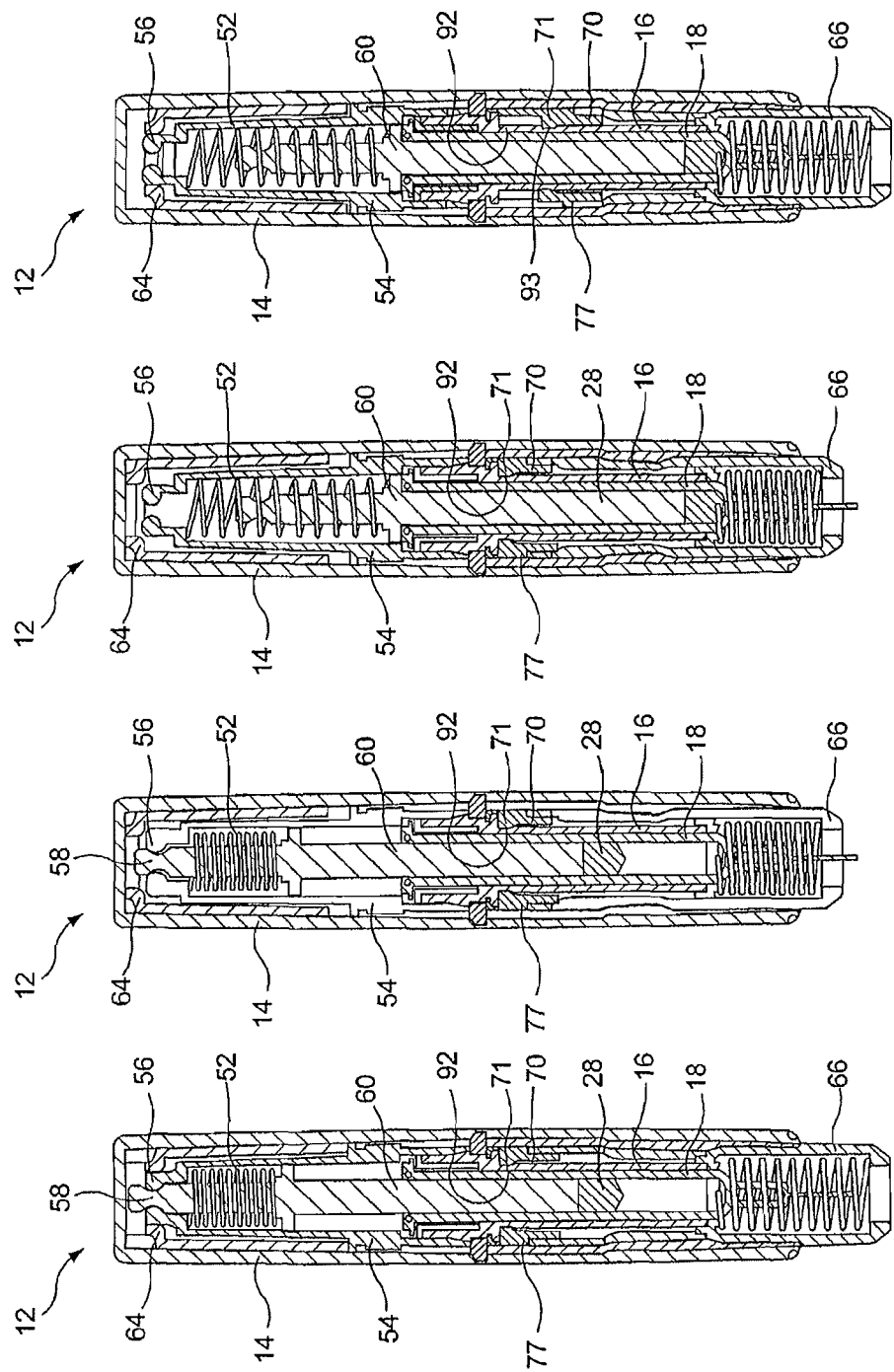
FIG. 6A is a cross-sectional view of the injection device of FIG. 1 in a ready state.
FIG. 6B is a cross-sectional view of the injection device of FIG. 1 at the start of an injection state.
FIG. 6C is a cross-sectional view of the injection device of FIG. 1 at the end of an injection state.
FIG. 6D is a cross-sectional view of the injection device of FIG. 1 in a locked state.
Figure 8:
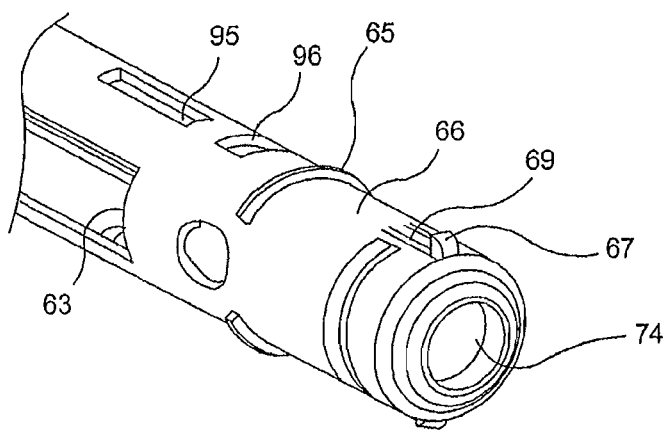
FIG. 8 is a perspective view of a needle guard according to an embodiment of the injector of FIG. 1.

The housing 14 can have a needle guard 66 that is moveable with respect to the outer housing 14. In the embodiment of the needle guard 66 shown in FIG. 2, the needle guard 66 is in a protecting position, in which the needle 24 is disposed within the guard 66. A ridge 65 (FIG. 8) abuts an interior surface of outer housing 14 so as to maintain needle guard 66 within housing 14 when needle guard 66 is fully extended into the protecting position. The needle guard 66 can be retractable, in some embodiments into the outer housing 14, in a proximal direction to an injecting position, in which the needle tip 26 and an end portion of the needle 24 are exposed as shown in FIGS. 6B and 6C for insertion into a patient. In some embodiments, the proximal movement of the guard 66 is prevented at the injecting position.

The needle guard 66 can be associated with the latch 64 such that when the guard 66 is displaced proximally it slides the latch 64 in a proximal direction to release the trigger protrusions 56 from the recess 58. In some embodiments, the latch 64 has a latching portion 68 that abuts the inner housing 54 in an association to bias and maintain the trigger protrusions 58 positioned in the blocking association with the ram 60 prior to the firing of the injector 12. In some embodiments, when the latch 64 is slid proximately by the retracting of the guard 66 to the injecting position, the latching portion 68 slides beyond the portion of inner housing 54 that it contacts and the trigger protrusions 56 flex away from the recess 58 of the ram 60, allowing the trigger protrusions 56 to move radially outwardly from the recess 58 and therefore from the blocking association. When this happens, spring 52 biases the ram 60 against plunger 28 to move distally in the injector 12.

In some embodiments, a cap 110 can be affixable on the distal end of the injector 12 so as to cover needle guard 66 and prevent accidental displacement thereof during shipping or during handling prior to injection. Cap 110 can affix to the distal end of outer housing 14 by press-fit, screw fit or the like. In certain embodiments, cap 110 can include a pair of projections 112 extending inwardly (FIG. 9), that form a distally-facing ridge 114. In such embodiments, needle guard 66 can be formed with a pair of radially-extending flanges 67 (FIG. 8) that are configured to abut the distal ridge 114 of projection 112 to secure cap 110 to injector 12. In some embodiments, the upper edge 116 (FIG. 9) of cap 110 can abut the distal end of outer housing 14 such that distal ridges 114 of projection 112 are held against flanges 67. This arrangement of the cap 110 prevents compression of the needle guard 66 proximally into the housing, as the cap 110 is juxtaposed between the guard 66 and housing, securing needle guard 66 in the protecting position to help prevent accidental firing of the injection mechanism.

Figure 9:
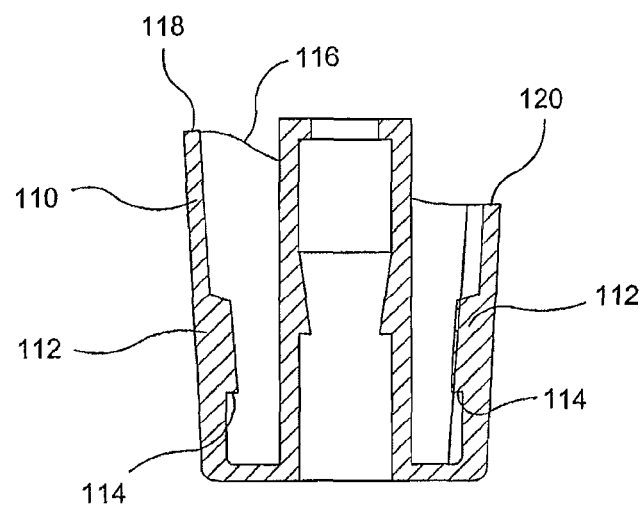
FIG. 9 is a cross-sectional view of the cap shown in FIG. 1.

In some embodiments, cap 110 can be removed from injector 12 by twisting cap 110 relative to housing 14 such that projections 112 are moved out of alignment with flanges 67, which allows the cap 110 to be moved distally away from needle guard 66. To prevent accidental removal of cap 110 from injector 12 due to inadvertent twisting of cap 110, in some embodiments the cap 110 engages the housing 14 and/or the needle guard 66 to require an initially elevated force, such as requiring the cap 110 to snap away from its closed position before completing the rotation to remove the cap 110. For example, upper edge 116 of cap 110 can be inclined, as shown in FIG. 9 The incline can include a curve, as shown, but generally the edge 116 can have one edge 118 that is higher than the other edge 120. In some embodiments, the distal end of outer housing 14 can have a profile that matches that of upper edge 118 of cap 110. This arrangement requires deflection of cap 110 to allow for twisting thereof and increases the force necessary to cause cap 110 to twist relative to needle guard 66. In an alternative embodiment, the cap 110 can have a threaded or cammed association with the flanges 67, or can have another arrangement therewith so that the cap 110 is removed by rotating.

Cap 110 can be attached to injector 12 during assembly thereof. This can be done by properly aligning cap 110 and twisting it relative to needle guard 66 while applying a proximally-directed force thereto such that projections 112 move behind flanges 67. Alternatively, flanges 67 can be structured to be deflectable inwardly by disposing them on a corresponding tab 69 formed on needle guard 66. In such an embodiment, cap 110 can be assembled onto needle guard 66 prior to assembly of spring 72 thereinto, as spring 72 can interfere with the inward deflection of flanges 67. Alternatively, cap 110 can be resiliently deformable to allow cap 110 to be pressed onto needle guard 66 such that projections 112 pass over flanges 67.

In some embodiments, needle guard 66 can be resiliently biased distally towards the protecting position by compression coil spring 72. Also, the needle guard 66 can have an axial opening 74 to allow the needle 24 pass therethrough, and which may be sized according to the type of injector desired. In some embodiments, the construction of the injector 12 allows a user to push the distal end of the injector 12 against the patient's skin, pushing the needle 24 into the skin at an insertion location, substantially at the same speed as the injector 12 is pushed into the skin. Once the needle 24 is fully inserted to an insertion point at a desired penetration depth, the trigger mechanism fires causing the injector 12 to inject the medicament into an injection site.

In some embodiments, such as for subcutaneous injection using a needle-assisted jet injector, the needle guard 66 can be configured to allow insertion of the needle 24 to a penetration depth in the skin that is up to about 5 mm below the skin surface. In some embodiments, the penetration depth is about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6 mm, about 6.5 mm or any range determinable from the preceding depths (for example, about 0.5 mm to about 2.0 mm or about 3.5 mm to about 5.5 mm). In another embodiment, the distance by which the needle tip 26 extends past the needle guard 66 or the distal surface of the needle guard 66 that contacts the skin is up to about 5 mm. In some embodiments, the distance by which the needle tip 26 extends past the needle guard 66 or the distal surface of the needle guard 66 that contacts the skin is about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6 mm or any range determinable from the preceding depths (for example, about 0.5 mm to about 2.0 mm or about 3.5 mm to about 5.5 mm).

In another embodiment, such as for intramuscular injection using a needle-assisted jet injector, the injector 12 can be configured to allow the needle 24 to be inserted into the patient to a penetration depth in the skin, or alternatively beyond the distal surface of the needle guard 66, by a distance of up to about 20 mm. In some embodiments, the injector 12 can be configured to allow the needle 24 to be inserted into the patient to a penetration depth in the skin, or alternatively beyond the distal surface of the needle guard 66, by a distance of about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6 mm, about 6.5 mm, about 7.0 mm, about 7.5 mm, about 8.0 mm, about 8.5 mm, about 9.0 mm, about 9.5 mm, about 10.0 mm, about 10.5 mm, about 11.0 mm, about 11.5 mm, about 12.0 mm, about 12.5 mm, about 13.0 mm, about 13.5 mm, about 14.0 mm, about 14.5 mm, about 15.0 mm, about 15.5 mm, about 16.0 mm, about 16.5 mm, about 17.0 mm, about 17.5 mm, about 18.0 mm, about 18.5 mm, about 19.0 mm, about 19.5 mm, about 20.0 mm, or any range determinable from the preceding depths (for example, about 0.5 mm to about 20.0 mm or about 3.5 mm to about 15.5 mm). Other exposed needle 24 lengths can be selected for jet injection to different depths below the skin, with an overall penetration length of between about 0.5 mm and about 20 mm. In these embodiments, the needle guard 66 can be configured for retracting from a protecting position, in some embodiments covering the entire needle, to an injecting position, in which the desired length of the tip 26 of the needle 24 is exposed.

In an embodiment, the injection device may comprise a collar surrounding the needle and defining a collar cavity, the collar having a peripheral and forward skin-contacting surface that surrounds, is discontinuous, and is radially spaced from the needle and injection site by an area that is sufficiently large to allow a patient's skin to move into the collar cavity to properly position the needle to penetrate the patient for intradermal delivery of the substance to the injection site to allow spread of the injected substance under the skin while inhibiting or preventing backpressure within the skin from forcing the substance out through the injection site. An example of such an embodiment can be found in U.S. Pat. No. 8,162,886, hereby incorporated by reference in its entirety.

Safety member 80 can be removably affixed to the distal end of outer housing 14 and can include a body portion 84 and a pair of resiliently-flexible legs 82 extending therefrom (FIGS. 4A and 4B). Legs 82 are configured to extend into corresponding holes or slots 15 formed in the proximal surface of outer housing 14 and can be shaped to provide a pressure fit within slots 15 to retain safety member 80 on housing 14. The legs 82 can be biased outwardly and can further include tabs 86 disposed on the outside surfaces thereof to engage the inside of outer housing 14 at the location of slots 15 to further the retention of safety member 80 onto outer housing 14. In some embodiments, legs 82 are shaped to allow a user to remove safety member 80 from outer housing 14, when injection is desired. In some embodiments, however, legs 82 prevent safety member 80 from becoming accidentally or unintentionally dislodged from its attachment to outer housing 14.

Legs 82 abut (FIG. 3) the proximal-most surface of latching portion 64 when properly attached to outer housing 14 to hinder or prevent jostling or other motion of latching portion 64 in the proximal direction, which would cause the injection mechanism to fire. In some embodiments, legs 82 are configured in relationship to the housing 14 and the trigger mechanism of the injector 12 such that the force necessary for latching portion 64 to move legs 82 out of slots 15 is sufficient to prevent latching portion 64 from being jostled out of position due to vibration during shipping or from acute shock during shipping or handling caused by dropping of injector 12. Alternative safety members can be used to prevent inadvertent firing of the injector 12.

In an embodiment in which the injector 12 is configured as a needle-assisted jet injector, the spring 72 and the prefilled syringe 18 can be configured to jet inject a medicament such as a testosterone formulation. Thus, the spring 72 applies a force on the plunger 28 that can be sufficient to elevate the pressure within the medicament chamber 22 to a level high enough to eject the medicament from the needle 24 as a fluid jet. In several embodiments, jet injection is an injection of medicament from the needle tip 26 of the injector 12 with sufficient velocity and force to drive the medicament to locations remote from the needle tip 26.

Several jet injector embodiments, whether needle-assisted or needle-free, have an energy source selected to produce a high pressure in the medicament chamber 22 to eject the medicament therefrom with sufficient force and speed to exit the injector 12 as a fluid jet. It is believed that jet injectors deliver medicaments rapidly over a wider surface area under the subject's skin, by essentially "spraying" the medicaments into a subject subcutaneously, thereby rapidly exposing a greater surface area of the subject's target tissue to the medicaments. When delivered by an autoinjector, a medicament typically leaves the autoinjector and is deposited locally, since it is not shot remotely from an injection outlet, and is thus delivered in a bolus typically near the needle tip of the autoinjector. This is because an autoinjector requires additional injection time to deliver an injection into resistive media, such as tissue, as opposed to delivery into air. In contrast, embodiments of a powered injector disclosed herein, and in particular embodiments of a disclosed jet injector, display approximately no difference in injection time when injecting into resistive media versus air. Because the medicament delivered by a jet injector is essentially sprayed rapidly into the subject's tissue, typically remotely from the needle tip, the medicament does not leave the jet injector as a single drop or bolus and is thus typically not delivered to a subject as a bolus local to a needle tip. Therefore, by using the jet injectors disclosed herein, a medicament can be dispersed into a subject's tissue more efficiently. Additionally, because jet injectors deliver medicaments via high pressure and speed, the delivered medicaments have a far lower tendency to leak back out of the injection site around the needle or injection track. Therefore, leak-back from the depth the medicament is delivered back toward the injection site, and/or back to the surface of the subject's skin, can be significantly reduced by use of a jet injector. Therefore, when used to deliver one or more medicaments according to the present disclosure, such as, for example, a testosterone formulation, jet injectors significantly reduce the risk of exposure to the medicaments outside of the injection site, thereby reducing the risk of exposure to the medicaments to non-users and to the subject himself, in addition to reliably delivering the entire dose to the desired depth. Preventing or reducing leak-back is beneficial in improving compliance by ensuring that the medicament remains at the injection site at the desired depth. Preventing or reducing leak-back can also be beneficial to keeping medicaments contained to a single area, thereby preventing inadvertent exposure to the subject and/or to other individuals in his vicinity from leak-back to the surface of the skin. Such exposure can include, for example, direct contact with the medicament on the subject's skin or from atomized medicament that may reach the subject or nearby individuals through the air, or through another medium. Additionally, in many cases, patients who use the slow injection of a hand-powered hypodermic syringe or autoinjector risk removing the hand-powered injector from the injection site prematurely, before the shot is completed, leading to exposure of the medicament outside the patient's tissue. In some embodiments, there is substantially no leak-back or no leak-back. In other embodiments, there is no leak-back in about 95% of the injections. In certain embodiments, the amount of leak back is less than about 15% of the total injected volume of medicament, and in other embodiments, when used, the amount of leak back is no more than about 0.05% to about 15% of the total injected volume of medicament, about 0.1% to about 12.5% of the total injected volume of medicament, about 0.2% to about 10% of the total injected volume of medicament, about 0.3% to about 7.5% of the total injected volume of medicament, about 0.4% to about 5% of the total injected volume of medicament, about 0.5% to about 3% of the total injected volume of medicament, about 0.6% to about 2% of the total injected volume of medicament, or about 0.7% to about 1% of the total injected volume of medicament. In certain embodiments, the amount of leak back is less than about 15% of the total weight of the injected medicament. In certain other embodiments, the amount of leak back is no more than about 0.1% to about 15% of the total weight of the injected medicament, about 0.5% to about 12.5% of the total weight of the injected medicament, about 1% to about 10% of the total weight of the injected medicament, about 2% to about 7.5% of the total weight of the injected medicament, or about 3% to about 5% of the total weight of the injected medicament.

In some embodiments, the injector 12 is configured, and the injection conducted, to deliver a medicament in a manner to prevent or significantly reduce leak-back and the risk and incidence of undue exposure of the medicament to the air or to the outside surface of the patient's skin.

In some embodiments of needle-assisted jet injectors, short needles can be used to inject medicaments to different parts of the skin, in some embodiments subcutaneously, without any leak-back. Using a needle 24 that extends about 2.5 mm beyond the distal surface of the needle guard 66, a 27 gauge needle 24, and a pressure in the medicament chamber 22 peaking at about 300 p.s.i. and ending at around 100 p.s.i., resulting in a flow rate of about 0.5 mL/sec, 1 mL of medicament can be successfully be injected without significant leak-back in about 100% of the tested injections as shown, for example, in Table 3 where only slight or measurable, but still slight, wetness at an injection site was observed. Thus, needle-assisted jet injectors of the present disclosure permit jet injection of one or more medicaments using a very short needle reliably, regardless of the thickness of the patient's skin, age, weight or other factors.

In some embodiments, selection of the type of spring as a power source, adjustment of the force delivered by the spring, and/or the manner in which the spring is packaged within the assembled injector can lead to a significant reduction in the amount of time required to deliver a complete injection into a subject, a significant reduction m the spring force required to deliver the injection, and a longer shelf-life. For example, the spring present in many known auto injectors is configured so that a typical injection, in the volume range of about 0.8-1.5 ml, is completely delivered into a subject in 10-15 seconds. Embodiments of the injectors of the present disclosure can have their spring configured so as to deliver a complete injection of about 0.8-about 1.0 ml in volume in about 1 to about 5 seconds, in some embodiments in about 2 to about 4 seconds, and in some embodiments in about 3 seconds. It is believed that this decrease in time will increase patient compliance when embodiments of the autoinjectors of the present disclosure are used, as less time is required to deliver a complete injection and, thus, the patient will experience less pain.

Additionally, in some embodiments spring material can be selected so as to only allow a decrease in spring force over the stroke length of the injection as shown. Many known autoinjectors show a decrease in spring force over the course of a single injection of less than approximately 20%. In contrast, embodiments of the injectors of the present disclosure can be configured so that their spring force decreases by at least about 25% over the course of a single injection, in some embodiments from about 25% to about 50% over the course of a single injection, in some embodiments from about 30% to about 50% over the course of a single injection, and in some embodiments by about 50% over the course of a single injection Spring material can also be selected, and/or the spring can be set in the injector, so as to not have the spring in an overly compressed state during packaging and shipment of the spring to an end user or patient. This is advantageous because springs that are overly compressed for expended periods of time become over-stressed and show a loss of force over time For example, many known autoinjectors are packaged such that they spend most of their shelf-life with their springs compressed. When packaged in this manner, such known autoinjectors experience a decrease in spring force over time as the autoinjector sits on a shelf awaiting use. In contrast, embodiments of the injectors of the present disclosure can have springs that are made of a material that is sufficiently resilient so as to lose less force over time as it is compressed, and/or can have a spring configured in a fully assembled injector such that it is not in a fully compressed state until the time of injection. In this manner, embodiments of the injectors of the present disclosure lose from about 0% to about 15% of their spring force over a typical shelf life. In some embodiments, the injectors of the present disclosure lose from about 10% to about 12% of their spring force over a three year shelf life.

In some embodiments of single-shot injectors, injector 12 includes a disabling mechanism, such as a locking element, which can be provided as a locking ring 70 associated with the injection mechanism. As shown in FIGS. 6A-6D, locking ring 70 can be disposed between sleeve 16 and needle guard 66, and can interact with sleeve 16 and needle guard 66 such that the locking ring 70 only permits needle guard 66 to move relative to outer housing 14 through a single injection cycle. This includes movement from the protecting position (FIG. 6A) into the injecting position (FIGS. 6B, 6C) and then to return to the protecting position (FIG. 6D) under the force of compression spring 72. When needle guard 16 returns to the protecting position at the end of the injection cycle, locking ring is positioned relative to sleeve 16 and needle guard 66 such that further movement therebetween is restricted, thus disabling the injector from further making injections and retaining the needle 24 safely within the housing 14 of the injector 12.

As shown in FIGS. 6A-6D, movement of needle guard 66 through one locking cycle causes locking ring 70 to move relative to sleeve 16 from an injecting position to a locking position. In the injecting position, locking ring 70 is disposed such that the upper arms 71 of locking ring 70 engage a portion of the device that is associated with the medicament chamber 22, such as, for example, proximal notches 92 formed in the outer surface of sleeve 16. The engagement of upper arms 71 within proximal notches 92 releasably maintains locking ring 70 in the injecting position. As shown in FIG. 7, locking ring 70 can be generally annular in shape so as to surround the medicament chamber 22, either directly or indirectly, such as by surrounding sleeve 16. Locking ring 70 further includes a pair of lower arms 73, each having a tab 74 formed on the end thereof. When locking ring 70 is in the injecting position, tabs 74 are received in slot 95 formed in needle guard 66 such that needle guard 66 is slideable through a predetermined distance over locking ring 70. As needle guard 66 is moved into the injecting position with respect to outer housing 14, needle guard 66 slides over locking ring 70 such that tabs 74 reach the end of slot 95 and are depressed inwardly, allowing needle guard 66 to continue to move into the injecting position. When the injecting position is reached, tabs 74 align with holes 96 of needle guard 66, allowing lower arms 73 to return to their natural position, wherein the upper surfaces of tabs 74 engage an edge of the holes 96, thereby coupling locking ring 70 to needle guard 66.

As needle guard 66 returns to the protecting position, needle guard 66 pulls distally on locking ring 70, causing upper arms 71 to release from proximal notches 92. In some embodiments, upper arms 71 and proximal notches 92 are formed with mating inclined surfaces such that the inclined surfaces of upper arms 71 engage another portion of the injector 12 that is associated with the medicament chamber 22, such as by extending into proximal notches 92, but are forced outwardly by distally-directed movement relative thereto. This configuration allows the needle guard 66 to cause locking ring 70 to move therewith and out of the injecting position as needle guard 66 moves distally toward the protecting position over sleeve 16, which remains stationary.

When needle guard 66 reaches the protecting position, upper arms 71 move over distal notches 93 formed in sleeve 16 such that the upper surfaces of upper arms 71 engage the upper surface 94 of distal notches 93. Further, in such a position, flange 77 of locking ring 70 abuts surface 67 of needle guard to block needle guard 66 from distal motion relative to locking ring 70. This engagement prevents locking ring 70 from moving proximally with respect to sleeve 16. Because locking ring 70 is coupled to needle guard 66 in this configuration, and because sleeve 16 is attached to outer housing 14, needle guard 66 is locked relative to outer housing 14, and is prevented from being moved back into the injecting position. This prevents needle 24 from being accidentally exposed after use of injector 12. Alternative embodiments can use other mechanisms to prevent re-use of the injector or portion thereof. Some embodiments do not employ such a mechanism so that the injector can be reused. In some embodiments, after injection of the medicament, subsequent injection can be prevented automatically and exposure to or contact with remnants of the medicament that may remain on portions of the injector after the injection, such as on a needle tip or jet injection nozzle, can also be prevented or avoided by the construction of the injector 12.

Figure 11:
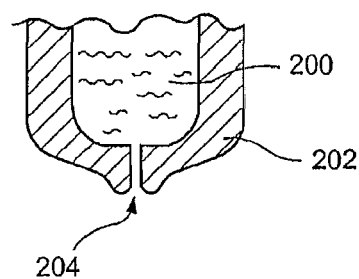
FIG. 11 is a cross-sectional view of a needle-free jet injection nozzle.

Referring to FIG. 11, a distal end of an embodiment of a needle-free jet injector is shown. The depicted injector can use the systems disclosed herein to fire the injection as described above for the needle injector embodiments, but instead of a needle, a jet nozzle 202 is used to inject the medicament into the subject. Nozzle 202 defines a jet outlet 204 having a diameter selected for causing the medicament 200 to exit the nozzle 202 as a fluid jet that is sufficiently strong to pierce the outer skin layers and to continue to the desired depth of injection.

In an embodiment, an injector may have one or more indicators that that injection of medicament has been completed. In an embodiment, an injector may have one or more indicators that injection of medicament is ongoing. In an embodiment, one or more indicators which independently and distinctively indicate that an injection is ongoing and that an injection has been completed. In an embodiment, a first indicator is different than a second indicator. Indicators can include, but are not limited to, audible indicators, tactile indicators (e.g., a click or a vibration), visual indicators, physical indicators, electronic indicators, or chemical indicators.

Table 1 shows the results of a trial comparing medicament leak-back that reached the surface of the skin of a subject after injection; data for needle-assisted jet injectors as compared to hand-driven hypodermic syringes is presented. The total number of injections for each group in the trial was 126, and all were administered by a trained health care professional.

TABLE 1

Medicament leak-back to the surface of the skin of a subject post injection.
% = percent of the total 126 injections administered.

| Injection site assessment post-injection | Needle-assisted jet injector | Syringe and needle |
|---|---|---|
| Site completely dry | 89 (71%) | 76 (60%) |
| Slight wetness on site | 36 (29%) | 50 (40%) |
| Measurable wetness, but slight (a drop) | 1 (0%) | 0 (0%) |
| Considerable wetness at injection site | 0 (0%) | 0 (0%) |

Because jet injectors deliver medicaments rapidly, in some embodiments in less than about 2 seconds, the amount of time patients must hold the injector in their tissue is dramatically decreased as compared to an injection delivered by a typical syringe or autoinjector. It is therefore believed that utilizing jet injectors according to the present disclosure will result in increased patient compliance and adherence to instructions and will therefore result in an increase in correctly administered injected doses. Additionally, the speed at which jet injectors deliver medicaments can further enhance patient compliance with regular injections as the amount of pain experienced by a patient self injecting a medicament will be minimized and, in many cases, may not exist.

In an embodiment, encompassed herein are a device and method for administering a viscous pharmaceutical formulation to a subject. In an embodiment, a method for administering a viscous pharmaceutical formulation to a subject comprises formulating a pharmaceutical formulation in the form of a solution or suspension having a viscosity of between about 25 and 2500 cps, providing the formulation in a injection device that includes a needle having an insertion length of less than about 10 mm or is needle-free; and administering the formulation from the injection device through an orifice having a diameter of at least about 0.2 mm by jet injection into a subject. In certain embodiments, the viscosity referenced herein can be a dynamic viscosity which can be measured by a Brookfied viscometer. In other embodiments, the viscosity referenced herein can be a kinematic viscosity which is determined by using a capillary viscometer in which a fixed volume of fluid is passed through a small orifice at a controlled temperature under the influence of gravity. In certain embodiments, the viscosity is measured at 20 degrees C. In other embodiments, the viscosity is measured at 25 degrees C.

In other embodiments, an injectable carrier including an amount of testosterone suspended or dissolved therein has a viscosity between 25 and 300 cps at room temperature (e.g., 20-25 degrees C.). In certain embodiments, the viscosity is between 90 to 120 cps, in other embodiments the viscosity is about 110 cps. In other embodiments the viscosity is greater than or equal to about 70 cps.

In certain embodiments, the carrier is coconut oil, soybean oil, sesame oil, castor oil. Other oils include: arachis (peanut) oil, castor oil, cottonseed oil, ethyl oleate, polyoxyethylated castor oil (HCO-60, polyoxyl 60 hydrogenated castor oil, Cremophor® EL), safflower oil, and soybean oil In an embodiment, the formulation includes a pharmaceutically suitable oil and is administered from the injection device at a pressure of greater than about 50 psi. In an embodiment, the oil is sesame oil.

In an embodiment, the injection device has an injection needle with a bore of about 0.3 mm or about 0.5 mm. Other gauges can also have suitable bores, e.g., 22 gauge, 25 gauge or 27 gauge.

Figure 10:
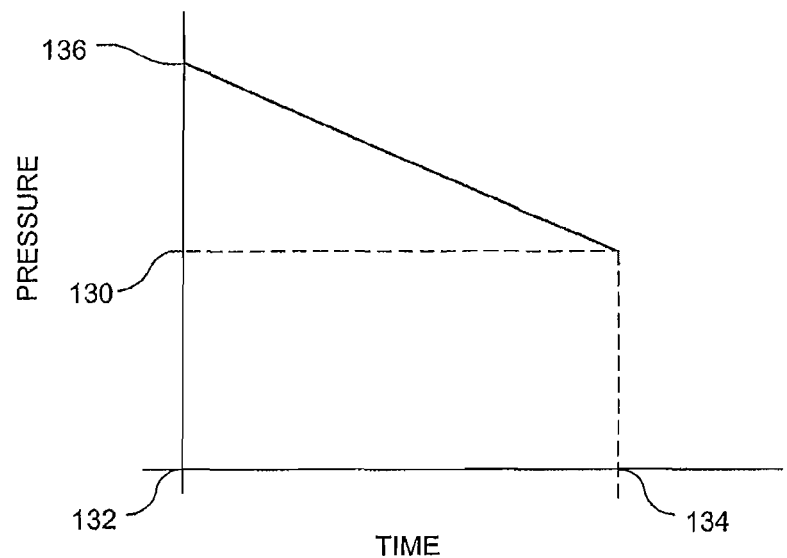
FIG. 10 is a graph showing the pressure within the liquid chamber of an embodiment of an injection device according to the present disclosure, as a function of time.

Referring to the graph shown in FIG. 10, numeral 132 represents the point in time when an embodiment of injector 12 is fired, and numeral 134 represents the point of completion of injection. In some embodiments, injection is completed when the plunger 28 hits the distal wall of the medicament container 20. Numeral 136 represents the initial and peak pressure during the injection, and numeral 130 represents the final pressure during the injection. In some embodiments, the spring 72 has a linear spring constant and an injection-assisting needle 24 is used to puncture the skin before commencing the injection. The pressure of injection therefore drops substantially linearly from the start of the injection 132 until the injection is completed 134 The final pressure 130 at the end 134 of the injection is sufficiently elevated so that even at the end of the firing stroke of ram 60, the medicament is still jet injected, and a very small amount or none of the medicament is deposited in a bolus around the needle tip 26

In some embodiments of needle-assisted jet injectors, the peak pressure 136 during the injection is less than about 1,000 p.s.i., in some embodiments less than 950 p.s.i., in some embodiments less than 900 p.s.i., in some embodiments less than 850 p.s.i., in some embodiments less than 800 p.s.i., in some embodiments less than 750 p.s.i., in some embodiments less than 700 p.s.i., in some embodiments less than 650 p.s.i., in some embodiments less than 600 p.s.i., in some embodiments less than 550 p.s.i., in some embodiments less than 500 p.s.i., in some embodiments less than 450 p.s.i., in some embodiments less than 400 p.s.i., and in some embodiments less than about 350 p.s.i. In some embodiments, at the end of the injection, the pressure 130 applied to the medicament in the medicament chamber 22 can be at least about 80 p.s.i., in some embodiments at least about 90 p.s.i., in some embodiments at least about 100 p.s.i., in some embodiments at least about 150 p.s.i., in some embodiments at least about 200 p.s.i., in some embodiments at least about 250 p.s.i., in some embodiments at least about 300 p.s.i., in some embodiments at least about 350 p.s.i., in some embodiments at least about 400 p.s.i., in some embodiments at least about 450 p.s.i., and in some embodiments at least about 500 p.s.i. In some embodiments, the initial pressure 136 can be about 330 p.s.i., and the final pressure 130 is about 180 p.s.i. In some embodiments, the initial pressure 136 is about 300 p.s.i., dropping to around 60 p.s.i. at the end 134 of the injection. Other injection rates are used for other embodiments discussed herein. For example, needle-free jet injectors can exert an injection pressure in the range of about 4,000 p.s.i. or greater. Other embodiments of jet injectors utilize lower injection pressures, such as at least about 80 p.s.i. or at least about 60 p.s.i. In contrast, known autoinjectors typically use pressures lower than 60 p.s.i.

The needles used in some embodiments of both autoinjectors and needle-assisted jet injectors are between 26 and 28 gauge, and in some embodiments are around 27 gauge. Other needle gages can also be used where the other components are cooperatively configured to produce the desired injection including, for example, mini-needles. In some embodiments, the components of the injector 12 can be configured to jet inject one or more medicaments to a subcutaneous injection site.

At about room temperature, in a device having a gauge needle as described herein, in embodiments of needle-assisted jet injectors, injection rates are below about 0.75 mL/sec, in some embodiments below about 0.6 mL/sec, in some embodiments at least about 0.2 mL/sec, in some embodiments at least about 0.3 mL/sec, and in some embodiments at least about 0.4 mL/sec. In some embodiments, the injection rate is selected from below about 0.75 mL/sec, below about 0.7 mL/sec, below about 0.65 mL/sec, below about 0.6 mL/sec, below about 0.55 mL/sec, below about 0.5 mL/sec, below about 0.45 mL/sec, below about 0.4 mL/sec, below about 0.35 mL/sec, below about 0.3 mL/sec, and below about 0.25 mL/sec. In some embodiments, the injection rate is about 0.05 mL/sec, 0.1 mL/sec, about 0.15 mL/sec, about 0.20 mL/sec, about 0.25 mL/sec, about 0.30 mL/sec, about 0.35 mL/sec, about 0.40 mL/sec, about 0.45 mL/sec, about 0.50 mL/sec, about 0.55 mL/sec, about 0.60 mL/sec, about 0.65 mL/sec, about 0.70 mL/sec, about 0.75 mL/sec, about 0.80 mL/sec, about 0.85 mL/sec, about 0.90 mL/sec, or any range determinable from the preceding injection rates (for example, about 0.05 mL/sec to about 1.5 mL/sec or about 0.70 mL/sec to about 0.75 mL/sec). In embodiments of needle-assisted jet injectors, injection rates are selected from at least about 0.2 ml/sec, at least about 0.25 ml/sec, at least about 0.3 ml/sec, at least about 0.35 ml/sec, at least about 0.4 ml/sec, at least about 0.45 ml/sec, at least about 0.5 ml/sec, at least about 0.55 ml/sec, at least about 0.6 ml/sec, at least about 0.65 ml/sec, and at least about 0.7 ml/sec.

In some embodiments, the injection of the entire amount of medicament is completed in less than about 15 seconds, in some embodiments in less than about 12 seconds, in some embodiments in less than about 11.5 seconds, in some embodiments in less than about 11.0 seconds, in some embodiments in less than about 10.5 seconds, in some embodiments in less than about 10.0 seconds, in some embodiments in less than about 9.5 seconds, in some embodiments in less than about 9.0 seconds, in some embodiments in less than about 8.5 seconds, in some embodiments in less than about 8.0 seconds, in some embodiments in less than about 7.5 seconds, in some embodiments in less than about 7.0 seconds, in some embodiments in less than about 6.5 seconds, in some embodiments in less than about 6.0 seconds, in some embodiments in less than about 5.5 seconds, in some embodiments in less than about 5.0 seconds, in some embodiments in less than about 4.5 seconds, in some embodiments in less than about 4 seconds, in some embodiments in less than about 3.5 seconds, in some embodiments in less than about 3 seconds, in some embodiments in less than about 2.5 seconds, in some embodiments in less than about 2 seconds, and in some embodiments in less than about 1.5 seconds. In some embodiments, the medicament injection takes at least about 1.0 second, about 1.5 seconds, about 2.0 seconds, about 2.5 seconds, about 3.0 seconds, about 3.5 seconds, about 4.0 seconds, about 4.5 seconds, about 5.0 seconds, about 5.5 seconds, about 6.0 seconds, about 6.5 seconds, about 7.0 seconds, about 7.5 seconds, about 8.0 seconds, about 8.5 seconds, about 9.0 seconds, about 9.5 seconds, about 10.0 seconds, about 10.5 seconds, about 11.0 seconds, about 11.5 seconds, about 12.0 seconds, or any range determinable from the preceding times (for example, about 3.0 seconds to about 8 seconds or about 10 seconds to about 12 seconds).

In some embodiments, injection of the medicament occurs at about 0.1 mL/sec, completing an injection of 1 mL in about 10 seconds. Other injection rates however, are possible for the alternative embodiments of the injectors 12 disclosed herein. For example, in some embodiments injector 12 can be configured to deliver a typical flow rate for needle-free jet injection, which can be about 1.5 mL/second, and in some embodiments injector 12 can be configured to deliver a typical flow rate for an autoinjector, which can be about 0.5 mL in 0.3 seconds.

Injection rates can be affected by a number of factors such as, for example, the gauge of the needle used to inject the medicament, the viscosity of the medicament itself, the glide force of the plunger 28 in the syringe barrel, the temperature of the medicament to be injected, and the temperature of the room in which the injection is administered, as temperature can have a direct effect on viscosity. In various embodiments, tissue resistance does not impact the rate of injection embodiments of the injectors of the present disclosure are capable of achieving. In various aspects, these parameters can be selected and optimized in order to deliver a volume of injection in a desired manner. Such selection and optimization can be readily performed by a person having ordinary skill in the art without undue experimentation.

In an embodiment, an injector may have the capability to heat the testosterone composition contained therein to thereby reduce viscosity and thereby decrease injection time of the composition contained therein. In an embodiment, a heating device is an integral part of the injector. In an embodiment, a heating device is external to the injector. In an embodiment, a heating device has an optional temperature sensing controller. In an embodiment, an injector has one heating device. In an embodiment, an injector has more than one heating device. Non-limiting examples of heating methods and/or devices include electrical, chemical, and exothermic sources.

In an embodiment, a heating mechanism heats the medicament contained within the injector to a temperature above room temperature. In an embodiment, a heating device heats the medicament contained within the injector to a temperature about 5 degrees C. above room temperature, or about 10, about 15, about 20, about 25, about 30, about 35, about 40, about 45, or about 50 degrees C. above room temperature (e.g., 20 to 25 degree C.). In one embodiment, the heating mechanism is an electronic, chemical or mechanical heating mechanism. In another embodiment, the mechanism or method of use includes placing a device proximal to a heat source (e.g., under a human arm).

In an embodiment, a heating device or mechanism further comprises at least one indicia that the heating device is operational, non-operational, and/or at the desired temperature. In an embodiment, a heating device has one or more indicia to indicate to the user that the device has reached a temperature suitable for dispensation of the medicament from the device. In an embodiment, an indicator is a visual indicator. In an embodiment, an indicator is an audible or a tactile indicator In some embodiments, a viscous medicament that would otherwise require a longer injection time can still be injected into a subject in the rates set forth above by varying the gauge of the needle. For example, in some embodiments a 26 gauge needle can be utilized with the needle-assisted injectors of the present disclosure to inject a viscous material, in some embodiments a 27 gauge needle can be utilized with the needle-assisted injectors of the present disclosure to inject a viscous material, and in some embodiments a 28 gauge needle can be utilized with the needle-assisted injectors of the present disclosure to inject a viscous material. In each of the foregoing embodiments, the rates of injection are the same as those rates disclosed above. Therefore, by varying the gauge of the needle according to the viscosity of the medicament to be injected, the rates of injection can be maintained. In some embodiments, a 27 gauge needle can be utilized with one or more embodiments of the injectors of the present disclosure to deliver 1.0 ml of an aqueous solution into air in a duration of time from between about 1.0 to about 2.0 seconds, in some embodiments between about 1.5 and about 2.0 seconds, and in some embodiments in about 1.7 seconds. In some embodiments, a 27 gauge needle can be utilized with one or more embodiments of the injectors of the present disclosure to deliver 1.0 ml of an aqueous solution into tissue in a duration of time from between about 1.0 to about 2.0 seconds, in some embodiments between about 1.3 and about 2.0 seconds, in some embodiments in about 1.5 seconds, and in some embodiments in about 1.3 seconds. In some embodiments, a 27 gauge needle can be utilized with one or more embodiments of the injectors of the present disclosure to deliver 1.0 ml of a viscous solution, having a viscosity equivalent to 10% w/w polyethylene glycol 20,000 in water, into air in a duration of time from between about 1.0 to about 5.0 seconds, in some embodiments between about 2.5 and about 5.0 seconds, in some embodiments in about 4.3 seconds, and in some embodiments in about 4.0 seconds. In some embodiments, a 27 gauge needle can be utilized with one or more embodiments of the injectors of the present disclosure to deliver 1.0 ml of a viscous solution, having a viscosity equivalent to 20% w/w polyethylene glycol 20,000 in water, into air in a duration of time from between about 10 to about 15 seconds, in some embodiments between about 12 and about 15 seconds, and in some embodiments in about 14 seconds.

The cgs physical unit for dynamic viscosity is the poise (P), which is more commonly expressed in ASTM standards as centipoise (cP). Typically, aqueous solutions at 20° C. have a viscosity of approximately 1 cP In several embodiments, injectors of the present disclosure can be configured to produce a flow rate, or a rate of injection, of 0.5 ml/second for aqueous solutions having a cP of, or close to, 1.0, through a 27 gauge needle. In several embodiments, injectors of the present disclosure can be configured to produce a flow rate, or a rate of injection, into skin of 0.5 ml/second for aqueous solutions having a cP of, or close to, 1.0, through a 27 gauge needle.

U.S. Pat. No. 6,391,003, discloses the experimental results of pressures that can be successfully applied to a medicament in a glass cartridge, using 26 and 27 gauge needles. Table 2 illustrates exemplary injections with different peak pressures that can be used with a needle-assisted jet injector, especially when using a glass, prefilled syringe:

TABLE 2 exemplary injections that may be delivered by
a needle-assisted jet injector.
Pressure and Time (sec.) to Inject 1 cc

| Pressure | 26 Gauge needle | 27 Gauge needle |
|---|---|---|
| 150 p.s.i. | 2.1 | 4.2 |
| 200 p.s.i. | 1.9 | 3.9 |
| 240 p.s.i. | 1.7 | 3.3 |
| 375 p.s.i. | 1.4 | 3.1 |

Alternative embodiments can use higher or lower injection pressures. For instance, needle-free injectors may use higher pressures to penetrate the skin without a needle, and autoinjectors will typically use lower pressures to simulate a hand-powered syringe injection.

II. Other Injectors

In one or more alternative embodiments, the present disclosure relates to an auto-injector for dispensing a predetermined dosage of a medicament comprising testosterone (e.g., preservative-free), the auto-injector including a housing that is preferably oval or elliptical in shape such that it is more ergonomic. In these alternative embodiments, U.S. Pat. Nos. 7,449,012 and 7,794,432 are hereby incorporated by reference in their entirety. The oval shape prevents the auto-injector from rolling off a table or flat surface, while providing a larger surface area for printing user instructions. A cartridge container is disposed within the housing. A cartridge is received within the cartridge container. The cartridge has at least one opening therein and contains a medicament. The medicament is rearwardly confined by a plunger. The cartridge includes a needle assembly to dispense the medicament therethrough. The cartridge is advanced within the cartridge container from a stored position to an operation position where the needle extends from the cartridge container such that the dose of medicament can be administered. An actuation assembly or power pack provides a stored energy source that is capable of being released to drive the plunger within the cartridge to dispense the medicament through the needle assembly into the user and allowing the needle to be accessible on activation.

Another aspect of the auto-injector of an alternative embodiment is the provision of a needle cover received within the housing. The needle cover shields the user from inadvertent exposure to the needle after use of the auto-injector providing sharps protection. Theoretically, the operation of the needle cover is fail safe because the cover will not deploy until after the needle penetrates the user. During operation, the needle of the cartridge extends through an opening in the needle cover to permit the dispensing of a dose of medicament. After use of the auto-injector, the needle cover is held in a locked position to prevent the cover from being retracted to expose the needle. According to another aspect of an alternative embodiment, the needle cover has a locked retracted position prior to activation of the auto-injector, thus maintaining a compact configuration of the device prior to use. According to another aspect of an alternative embodiment, the actuation forces associated with the auto-injector are not imparted on the needle cover.

In accordance with another aspect of an alternative embodiment, the auto-injector has a first locking assembly that holds the needle cover in the first locked position. The first locking assembly may be located on the cartridge container. The first locking assembly may include at least one locking tooth pivotally connected to the cartridge container or the needle cover. Each locking tooth releasably engages the needle cover and includes a locking surface constructed and arranged to contact a surface on the needle cover or the cartridge container. Each locking tooth may be formed as a separate component that is connected to the container or cover. It is contemplated that the locking teeth may be formed as integral parts of the needle cover or cartridge. A spring force of the locking tooth biases the locking surface into contact with the needle cover. The spring force may be provided by a spring portion of the locking tooth. The spring force may also be provided by a separate spring assembly biasing the locking surface into contact with the needle cover. Each locking tooth is preferably pivotally connected to the cartridge container. Each locking tooth pivots in response to movement of the cartridge within the cartridge container. It is also contemplated that the locking teeth can pivot in response to movement of the collet or the power pack. Typically, the locking surface pivots out of contact with the needle cover when the locking tooth pivots in response to the movement of the cartridge. The spring force and the force exerted by the locking teeth on the cartridge are controlled such that they negligibly or minimally impede the motion of the cartridge during the injection operation to avoid any premature rupturing of the diaphragm within the cartridge and premature administering of the medicament.

In an aspect of an alternative embodiment, the needle cover is spring biased so that the cover is biased outwardly from the housing to cover the exposed needle after the first locking assembly is released. In accordance with another aspect of an alternative embodiment, the auto-injector has a second locking assembly that holds the needle cover in the second locked position. The second locking assembly may be located on the cartridge container, the outer body or the cover member. The second locking assembly may include at least one locking arm or wing preferably connected to the cartridge container. Each locking arm is spaced from the cartridge container such that the locking arm can be temporarily compressed against the cartridge container as the needle cover moves from the first locked position to the second locked position. Each locking arm has a locking surface to engage the needle cover when the needle cover is in the locked extended position. Each locking arm has a thick strut portion and a thin strut portion, wherein the thick strut portion is outwardly curved and the thin strut portion is inwardly curved. This construction maintains the locking arm in a normal uncompressed state to reduce stress on the cartridge container. This also permits a smooth deployment of the cover member. Furthermore, this arrangement ensures that the thick strut portion will buckle into a stable condition. This creates a stronger lock to prevent the cover member from being moved rearwardly to a retracted position. The inwardly curved nature of the thin strut portion allows the thick portion to buckle in a controlled manner to a stable condition. Additionally, the outwardly curved shape of the thick strut portion provides for fail safe locking of the cover member in the extended position. In the event that the thin strut breaks, the thick strut portion will still engage the cover member to maintain it in an extended locked position.

The cartridge container of an alternative embodiment may further include at least one ledge extending outwardly therefrom. Each ledge is constructed and arranged to engage an edge of an opening in the needle cover to limit the travel of the needle cover with the respect to the cartridge container when the needle cover is in the extended position. When the ledge on the cartridge container engages the edge of the opening, the outward travel of the needle cover is limited.

The second locking assembly limits the inward travel of the needle cover. The needle cover and the cartridge container contain openings formed therein. When the openings are aligned prior to activation of the auto-injector, user can view the contents of the cartridge through the housing and the openings. The housing may be transparent or opaque. When opaque, the housing may contain an opening that can be aligned with the openings in the needle cover and cartridge container so that the color of the medicament may be checked to determine whether or not the medicament is suitable for injection. If the medicament is discolored, the user will know not to administer the medicament. When the openings are not aligned after operation of the auto-injector, the user is no longer able to view the contents of the cartridge through the openings providing a visual indication to the user that the auto-injector has been used.

Another aspect of an alternative embodiment is the construction and arrangement of the actuation assembly or power pack, which is mounted within the housing adjacent to an open end. A release pin or safe pin is removably attached to the actuation assembly to prevent inadvertent actuation of the auto-injector when the release pin is in place. A pin or stem on the release pin is received within an opening in the actuation assembly to prevent actuation of the auto-injector. This opening in the power pack is spaced from the open end of the housing such that the opening is less visible to a user prior to administering the drug. This arrangement is provided so that user will not orient the incorrect end of the auto-injector against the injection surface of the user. The power pack is recessed or spaced from the end of the housing, which provides an indication to the user that pressing the power pack will not operate the auto-injector. The recessed nature of the power pack serves to hide the release pin hole in the power pack when the user is viewing the instructions on the outer body such that the user does not confuse the release pin hole with the opening through which the needle passes for administering the medicament. The release pin includes at least one tab extending therefrom. The tab is compression fit into a complimentary recess formed in the actuation assembly to prevent the inadvertent removal of the release pin. The tabs also prevent rotation of the release pin such that the user easily recognizes that the release pin must be pulled in order to be removed.

The actuation assembly of an alternative embodiment includes an outer body, which is configured to engage the release pin. The outer body is constructed to be connected to the housing. An inner body is operatively coupled to the outer body. At least one retention tab on the inner body secures the inner body to the outer body. The inner body is capable of limited movement with respect to the outer body. A collet is operatively coupled to the inner body. An energy source is operatively connected to the inner body and the collet. Unlike conventional collets, the collet in the present invention is molded as a single piece. No spacers or other components are provided between the collet and the plunger in the cartridge. This arrangement simplifies construction of an alternative embodiment. Different sized collets can be produced and installed into the actuation assembly, such that only the collet needs to altered when different sized cartridges are used or a different sized dosage of medicament is to be administered.

III. Medicament Compositions

In certain embodiments, a medicament of the present invention can be any drug, including testosterone, which can be useful alone or in combination with other embodiments and/or devices encompassed herein. In one embodiment, the drug is testosterone.

In one embodiment, a testosterone formulation encompassed herein comprises at least one preservative, and in particular, a pharmaceutically-acceptable preservative, and more particularly, a preservative suitable for one or more of intramuscular, subdermal, and subcutaneous administration. Suitable preservatives include, but are not limited to, antimicrobial agents, halogenated alcohols, parabens, and phenylmercuric salts. Non-limiting examples of preservatives include phenol, meta-cresol, benzyl alcohol, methyl paraben, propyl paraben, butyl paraben, benzalkonium chloride, chlorobutanol, thimerosal, phenylmercuric acetate, phenylmercuric borate, and phenylmercuric nitrate.

In one embodiment, a testosterone formulation encompassed herein does not comprise a preservative or is free of a preservative and in particular, free of a preservative described above. In one embodiment, a preservative-free testosterone formulation encompassed herein comprises testosterone enanthate. In an embodiment, a preservative free testosterone formulation is a unit dose of testosterone or a pharmaceutically acceptable ester or salt thereof in a pharmaceutically acceptable carrier. In an embodiment, a preservative free testosterone formulation is a multiple of at least two unit doses of testosterone or a pharmaceutically acceptable ester or salt thereof in a pharmaceutically acceptable carrier. In yet another embodiment, the composition is free or substantially free of precipitate (e.g., testosterone enanthate or testosterone cypionate precipitate).

In an embodiment, a testosterone formulation (e.g., preservative-free) comprises at least one viscous carrier. In yet another embodiment, a testosterone formulation (e.g., preservative-free) includes testosterone in oil. In an embodiment, a testosterone formulation (e.g., preservative-free) includes testosterone in sesame oil.

In an embodiment, testosterone in a composition encompassed herein is present in an amount selected from: about 5 mg, about 10 mg, about 15, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg of medicament or any range determinable from the preceding dosage amounts (for example, about 75 mg to about 150 mg or about 100 mg to about 200 mg). In another embodiment, testosterone is present in an amount greater than about 5 mg.

As will be understood by the skilled artisan, the amounts of testosterone encompassed herein may be contained within a suitable volume of fluid (e.g., a suitable carrier or oil), based on the method of administration and/or the device used for administration, desired testosterone concentration, etc., among other things. In an embodiment, the amount of medicament contained in and injected from medicament chamber 22 can be between about 0.02 mL and about 4 mL, in some embodiments less than about 3 mL. In other embodiments, the amount of medicament contained in and injected from medicament chamber 22 can be about 0.02 mL, about 0.04 mL, about 0.06 mL, about 0.08 mL, about 1.00 mL, about 1.02 mL, about 1.04 mL, about 1.06 mL, about 1.08 mL, about 2.00 mL, about 2.02 mL, about 2.04 mL, about 2.06 mL, about 2.08 mL, about 3.00 mL, about 3.02 mL, about 3.04 mL, about 3.06 mL, about 3.08 mL, about 4.00 mL, about 4.02 mL, about 4.04 mL, about 4.06 mL, about 4.08 mL, about 5.00 mL, or any range determinable from the preceding volumes (for example, about 0.04 mL to about 5.00 mL or about 1.04 mL to about 3.02 mL). Larger volumes may also be selected depending on the particular medicament(s) utilized and dosage required. In some embodiments, e.g., in reference FIG. 6A, a pre-filled syringe 18 containing the desired amount of medicament is assembled into the remaining parts of an injector 12. In some embodiments, the pre-filled syringe 18 contains from about 0.02 mL to about 4.00 mL of medicament-containing fluid. In some embodiments, the pre-filled syringe 18 contains about 0.02 mL, about 0.04 mL, about 0.06 mL, about 0.08 mL, about 1.00 mL, about 1.02 mL, about 1.04 mL, about 1.06 mL, about 1.08 mL, about 2.00 mL, about 2.02 mL, about 2.04 mL, about 2.06 mL, about 2.08 mL, about 3.00 mL, about 3.02 mL, about 3.04 mL, about 3.06 mL, about 3.08 mL, about 4.00 mL, about 4.02 mL, about 4.04 mL, about 4.06 mL, about 4.08 mL, about 5.00 mL, or any range determinable from the preceding volumes (for example, about 0.04 mL to about 5.00 mL or about 1.04 mL to about 3.02 mL) of one or more medicaments.

In one embodiment, an ester form of testosterone is used. In one embodiment, a testosterone formulation encompassed herein comprises testosterone enanthate and/or testosterone cypionate, collectively referred to herein as "testosterone". It is understood that alternative compounds that include the testosterone moiety are within the scope of the term "testosterone", including active metabolites of testosterone.

In an embodiment, a testosterone formulation encompassed herein is such that it can be administered through a fine-gauge needle, the methods of administration and the devices for administration encompassed and/or described in detail elsewhere herein. A non-limiting example of a fine gauge needle is a 27 gauge needle. However, other examples of fine gauge needles are described in detail elsewhere herein. In an embodiment, a testosterone formulation encompassed herein, when administered in combination with device encompassed herein, a dose can be administered using a force sufficient to smoothly overcome resistance to flow through the syringe body or needle. Methods of determining and optimizing flow rate for injection of a medicament are also described in detail elsewhere herein.

IV. Methods of Treatment

The present disclosure provides, in part, a method, device, and composition for treating hypogonadism, reduced infertility, lack of libido or erectile dysfunction, osteoporosis and anemia, a method for encouraging penile enlargement and height growth, and method of stimulating bone marrow and appetite.

The concentration of testosterone in the blood stream of a subject will depend on the amount of testosterone in the composition administered to the subject as well as the route of administration and the specific formulation used.

In an embodiment, a subject is treated with a single dose of a composition as encompassed herein. In an embodiment, a subject is treated with two or more doses of a composition as encompassed herein. In an embodiment, a subject is treated with multiple doses of a composition as encompassed herein. In an embodiment, a subject treated with multiple doses is treated for at least one day. In an embodiment, a subject treated with multiple doses is treated for at least one week. In an embodiment, a subject treated with multiple doses is treated for at least one month. In some embodiments, a patient is injected weekly or bi-weekly with one or more testosterone doses. The patient is preferably, but not limited to, being injected in the abdomen or thigh.

V. Pharmacokinetics

In an embodiment, a composition comprising testosterone (e.g., a preservative-free testosterone composition) administered to a subject as encompassed herein provides pharmacokinetics, including systemic bioavailability, that has substantially the same (or similar) pharmacokinetics, including systemic bioavailability, of testosterone when the same dose of testosterone is administered to said subject using needle and syringe, intramuscularly or subcutaneously. In another embodiment, the method of treating hypogonadism as encompassed herein comprises introducing into the subcutaneous, intradermal, or intramuscular tissue of a subject, from a needle assisted jet injection device, a composition comprising testosterone (e.g., preservative-free) in a dose ranging from about 5 mg to about 400 mg, wherein the pharmacokinetic profile of said testosterone delivered by said needle assisted jet injection device is substantially the same as the pharmacokinetic profile of the same dose of said testosterone when administered to said subject via needle and syringe, intramuscularly or subcutaneously.

As used herein, the values obtained or calculated for measured testosterone can be in reference to total testosterone, free testosterone, bio-available testosterone or serum testosterone.

In an embodiment, testosterone administered in accordance with the disclosure encompassed herein achieves comparable, e.g., bioequivalence, pharmacokinetic profile by generating $C_{max}$ and $T_{max}$ for the same period of time as compared to when the same dose of testosterone is delivered via a needle and syringe, intramuscularly, intradermally, or subcutaneously. In an embodiment, testosterone administered in accordance with the disclosure encompassed herein achieves a pharmacokinetic profile that is superior to that obtained by generating $C_{max}$ and $T_{max}$ for the same period of time as compared to when the same dose of testosterone is delivered via a needle and syringe, intramuscularly, intradermally, or subcutaneously.

In an embodiment, a composition comprising testosterone (e.g., a preservative-free composition) administered to a subject in accordance with the methods disclosed herein provides enhanced pharmacokinetics, including systemic bioavailability, of testosterone when the same dose of testosterone is administered to said subject using one of a transdermal cream, gel or patch or needle and syringe, intramuscularly, intradermally, or subcutaneously. In an embodiment, a method of administering testosterone in accordance with the disclosure encompassed herein comprises introducing into the subcutaneous, intradermal, or intramuscular tissue of a subject, from an injector device as encompassed herein and described elsewhere herein, a composition comprising testosterone (e.g., preservative-free) in a dose ranging from about 5 mg to about 400 mg, wherein the pharmacokinetic profile of testosterone delivered by the injector device is enhanced relative to the pharmacokinetic profile of the same dose of said testosterone when administered to said subject via one of a transdermal cream, gel or patch or needle and syringe, intramuscularly, intradermally, or subcutaneously. In an embodiment, a method of administering testosterone in accordance with the disclosure encompassed herein comprises introducing into the subcutaneous, intradermal, or intramuscular tissue of a subject, from a needle assisted jet injection device as encompassed herein and described elsewhere herein, a composition comprising testosterone (e.g., preservative-free) in a dose ranging from about 5 mg to about 400 mg, wherein the pharmacokinetic profile of testosterone delivered by the needle assisted jet injection device is bioequivalent to the reference-listed drug when administered via needle and syringe, intramuscularly, intradermally, or subcutaneously. In another embodiment, bioequivalent pharmacokinetic profile of testosterone delivered by the needle assisted jet injection device is enhanced as compared to the reference-listed drug when administered via needle and syringe, intramuscularly, intradermally, or subcutaneously.

In an embodiment of a 5 mg to 400 mg dose of the present disclosure, the pharmacokinetic profile provides a linear increase in testosterone exposure with increases in dose of testosterone administered. In an embodiment, the pharmacokinetic profile provides dose proportional increases in testosterone exposure (AUC and/or $C_{max}$). In another embodiment, the pharmacokinetic profile provides a linear or nonlinear relationship between AUC (ng*h/ml) of testosterone and dose of testosterone when the AUC (ng*h/ml) values are plotted against the corresponding dose values in a Cartesian Plane. In another embodiment, the pharmacokinetic profile provides a linear or nonlinear relationship between $C_{max}$ of testosterone and dose of testosterone when the $C_{max}$ values are plotted against the corresponding dose values in a Cartesian Plane. Pharmacokinetic information concerning testosterone and a needle assisted jet injector can also be found in provisional application Ser. No. 61/621,298, the content of which is hereby incorporated by reference in its entirety.

Accordingly, one embodiment of the present invention provides a method of treating hypogonadism in a subject in need of treatment, said method comprising introducing into the subcutaneous or intramuscular tissue of a patient in need of testosterone, from a needle assisted jet injection device, a composition comprising testosterone (e.g., preservative-free) in a dose ranging from about 5 mg to about 400 mg, wherein said method provides a pharmacokinetic profile whereby testosterone exposure increases linearly in proportion to increases in the dose strength (or level) of testosterone. In an embodiment, the pharmacokinetic profile provides an AUC that increases linearly in proportion to increases in the dose strength (or level) of testosterone administered. In another embodiment, the pharmacokinetic profile provides a $C_{max}$ that increases linearly in proportion to increases in testosterone dose level administered.

For comparison purposes, commercially available testosterone and the associated medication guides and package insert labels of Androgel 1% (NDA No. 021015), Androgel 1.62% (NDA No. 022309), Testim (NDA No. 021454) and Axiron (NDA No. 022504) can be used, and the package insert labels of each of the foregoing are hereby incorporated by reference in their entirety.

A. Effective Plasma Levels of Testosterone

In one embodiment, a method of administering testosterone comprises administering a composition comprising a unit dose of testosterone (e.g., preservative-free) or pharmaceutically acceptable ester or salt thereof in a pharmaceutically acceptable carrier subcutaneously to a mammal, wherein after administration the plasma level of testosterone is maintained at a therapeutically effective level for a period of time. In one embodiment, a Z1 time period is the time period for which the plasma level of testosterone is maintained at a therapeutically effective level.

In another embodiment, a composition encompassed herein, when administered according to the methods and the devices encompassed herein, maintains the plasma level of testosterone at a therapeutically effective level starting at about 1 minute after administration and ending at about 1 month after administration. In such an embodiment, a composition encompassed herein, when administered according to the methods and the devices encompassed herein, maintains the plasma level of testosterone at a therapeutically effective level starting at about 2 minutes after administration, or at about 3 minutes, about 4 minutes, about 5 minutes, about 10 minutes, about 20 minutes, about 30 minutes, about 45 minutes, about 60 minutes, about 2 hours, about 3 hours, about 4 hours, about 5 hours, about 6 hours about 7 hours about 8 hours about 9 hours, about 10 hours, about 11 hours, or about 12 hours after administration, up to about 1 month after administration. In an embodiment, a composition encompassed herein, when administered according to the methods and the devices encompassed herein, maintains the plasma level of testosterone at a therapeutically effective level starting at about 1 minute after administration and ending at about 25 days after administration, about 20 days after administration, about 15 days after administration, about 14 days after administration, about 13 days after administration, about 12 days after administration, about 11 days after administration, about 10 days after administration, about 9 days after administration, about 8 days after administration, about 7 days after administration, about 6 days after administration, about 5 days after administration, about 4 days after administration, about 3 days after administration, about 2 days after administration, about 1 day after administration, or about 0.5 days after administration.

In one embodiment, a first dose has a first profile and subsequent doses (which may be the same as or different from the first dose) impart different profiles. Depending upon patient response, dose, dose volume and timing of subsequent dosings, the pharmacokinetic profile of a patient can be customized to meet a particular patient's needs through the use of the present invention. In some embodiments, the present invention can be used to maintain therapeutic levels of testosterone during and/or across a prescribed dosing cycle (e.g., once weekly dosing for: 2 weeks, 3 weeks, 4 weeks, 5 weeks, two months, five months, a year, or more).

In an embodiment, a method of administering testosterone comprises administering a composition comprising a unit dose of a testosterone (e.g., preservative-free) or pharmaceutically acceptable ester or salt thereof in a pharmaceutically acceptable carrier subcutaneously to a mammal, wherein after administration, the plasma level of testosterone is maintained between about 300 ng/dl and about 1100 ng/dl for a time period, "Z1"

In one embodiment, a composition encompassed herein, when administered according to the methods and the devices encompassed herein, maintains the plasma level of testosterone between, e.g., about 300 ng/dl and about 1100 ng/dl starting at about 1 minute after administration and ending at about 1 month after administration. In yet another embodiment, a composition encompassed herein, when administered according to the methods and the devices encompassed herein, maintains the plasma level of testosterone between, e.g., about 300 ng/dl and about 1100 ng/dl starting at about 2 minutes after administration, or at about 3 minutes, about 4 minutes, about 5 minutes, about 10 minutes, about 20 minutes, about 30 minutes, about 45 minutes, about 60 minutes, about 2 hours, about 3 hours, about 4 hours, about 5 hours, about 6 hours about 7 hours about 8 hours about 9 hours, about 10 hours, about 11 hours, or starting at about 12 hours after administration, up to about 1 month after administration. In an embodiment, a composition encompassed herein, when administered according to the methods and the devices encompassed herein, maintains the plasma level of testosterone between, e.g., about 300 ng/dl and about 1100 ng/dl starting at about 1 minute after administration and ending at about 25 days after administration, about 20 days after administration, about 15 days after administration, about 14 days after administration, about 13 days after administration, about 12 days after administration, about 11 days after administration, about 10 days after administration, about 9 days after administration, about 8 days after administration, about 7 days after administration, about 6 days after administration, about 5 days after administration, about 4 days after administration, about 3 days after administration, about 2 days after administration, about 1 day after administration, or ending about 0.5 days after administration.

In an embodiment, the plasma level of testosterone is maintained at a value selected from the group consisting of about 300 ng/dl to about 1100 ng/dl, about 350 ng/dl to about 1050 ng/dl, about 400 ng/dl to about 1000 ng/dl, about 450 ng/dl to about 950 ng/dl, about 500 ng/dl to about 900 ng/dl, about 550 ng/dl to about 850 ng/dl, about 600 ng/dl to about 800 ng/dl, about 650 ng/dl to about 750 ng/dl, and about 675 ng/dl to about 725 ng/dl. In an embodiment, the plasma level of testosterone is maintained at a value selected from the group consisting of about 300 ng/dl, about 350 ng/dl, about 400 ng/dl, about 450 ng/dl, about 500 ng/dl, about 550 ng/dl, about 600 ng/dl, about 650 ng/dl, about 700 ng/dl, about 750 ng/dl, about 800 ng/dl, about 850 ng/dl, about 900 ng/dl, about 950 ng/dl, about 1000 ng/dl, about 1050 ng/dl, and about 1100 ng/dl. In an embodiment, the plasma level of testosterone is maintained at a value selected from the group consisting of at least about 300 ng/dl, at least about 350 ng/dl, at least about 400 ng/dl, at least about 450 ng/dl, at least about 500 ng/dl, at least about 550 ng/dl, at least about 600 ng/dl, at least about 650 ng/dl, at least about 700 ng/dl, at least about 750 ng/dl, at least about 800 ng/dl, at least about 850 ng/dl, at least about 900 ng/dl, at least about 950 ng/dl, at least about 1000 ng/dl, at least about 1050 ng/dl, and at least about 1100 ng/dl. In an embodiment, the plasma level of testosterone is maintained at a value selected from the group consisting of about 300 ng/dl or less, about 350 ng/dl or less, about 400 ng/dl or less, about 450 ng/dl or less, about 500 ng/dl or less, about 550 ng/dl or less, about 600 ng/dl or less, about 650 ng/dl or less, about 700 ng/dl or less, about 750 ng/dl or less, about 800 ng/dl or less, about 850 ng/dl or less, about 900 ng/dl or less, about 950 ng/dl or less, about 1000 ng/dl or less, about 1050 ng/dl or less, and about 1100 ng/dl or less.

Figure 12:
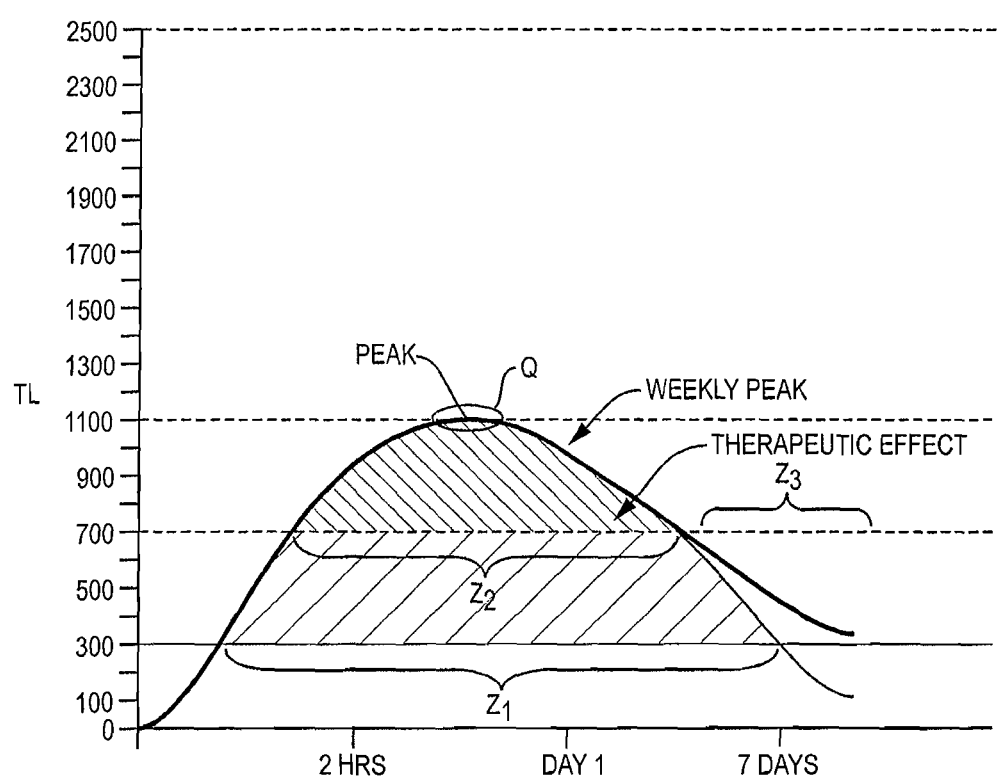
FIG. 12 is a graph illustrating an embodiment of the present disclosure in which serum testosterone demonstrates a peak upon injection and subsequently decreases to a therapeutically effective level.
Figure 14:
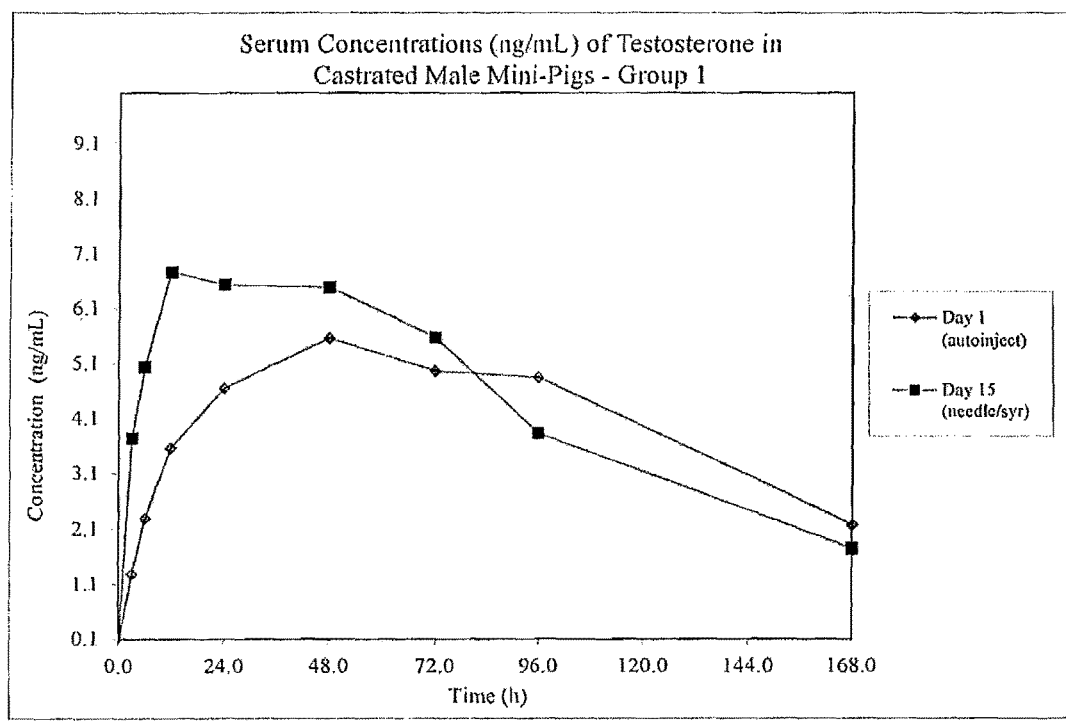
FIG. 14 is graph illustrating the serum concentration of testosterone in the group 1 mini-pigs of FIG. 13.
Figure 15:
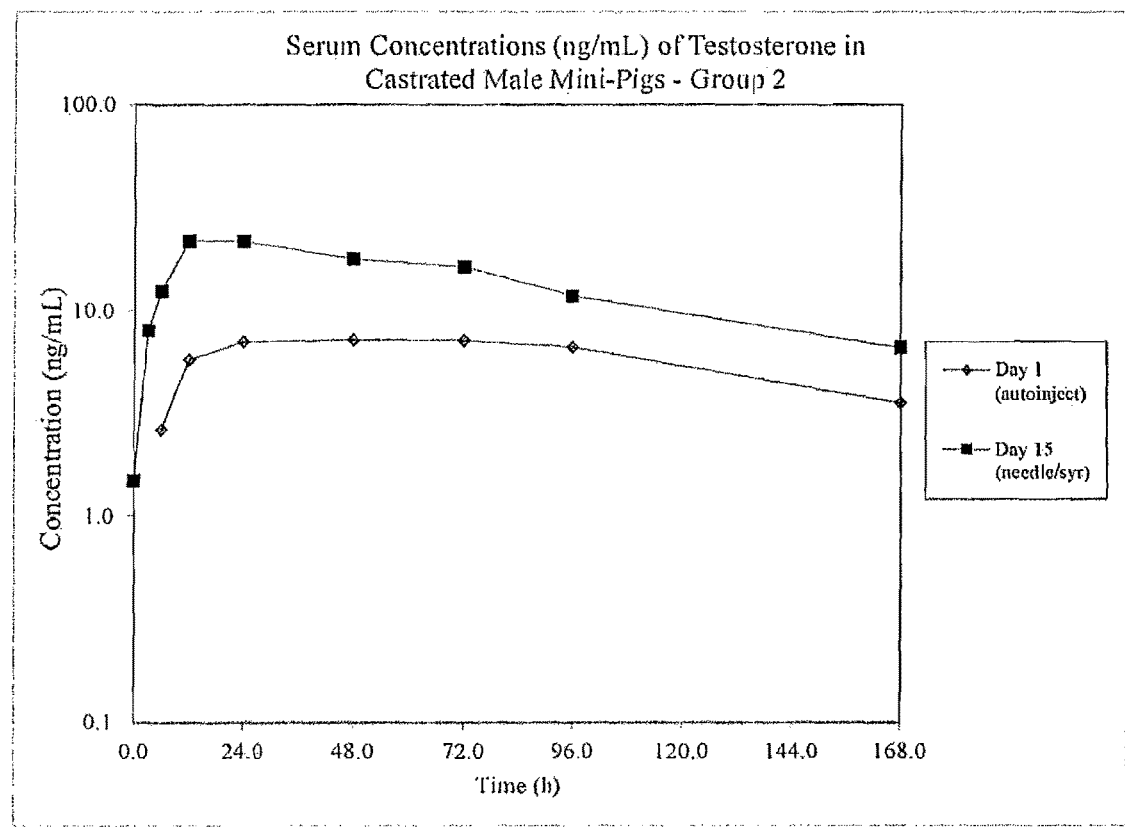
FIG. 15 is graph illustrating the serum concentration of testosterone in the group 2 mini-pigs of FIG. 13.
Figure 16:
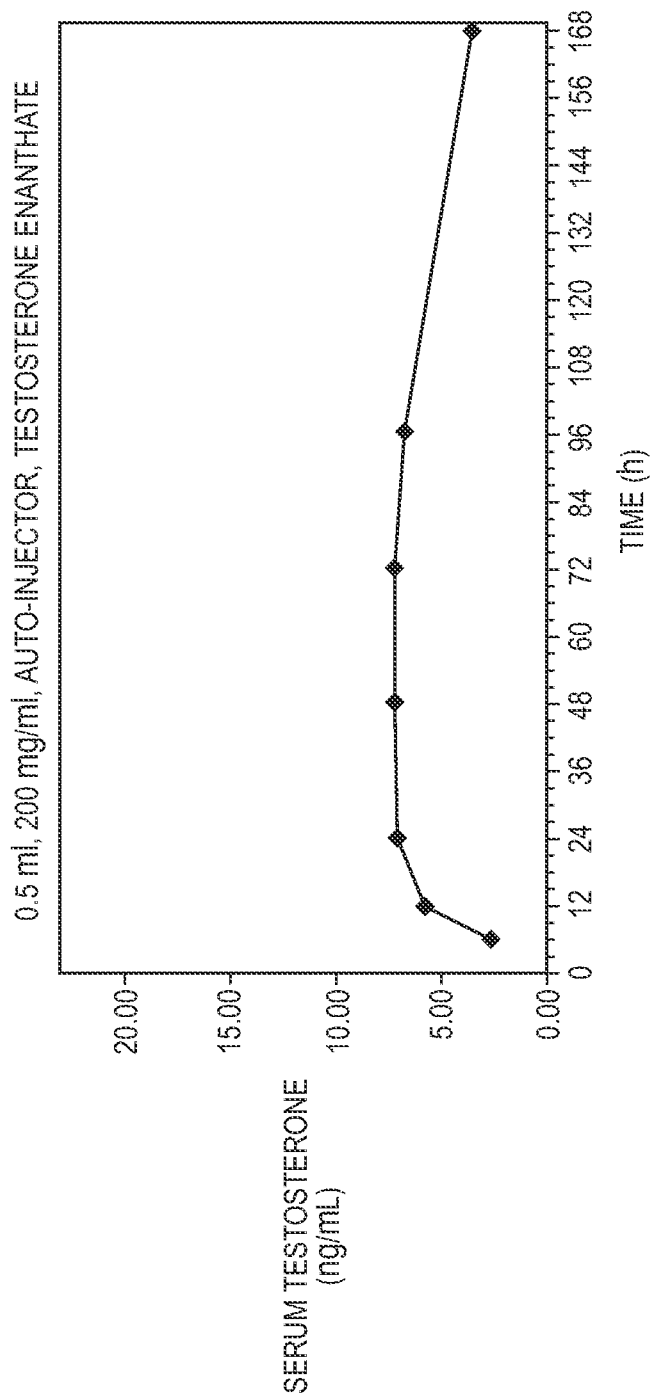
FIG. 16 is graph illustrating the serum concentration of testosterone for a 0.5 ml auto-injector injection of 200 mg/ml testosterone enanthate in sesame oil.
Figure 17:
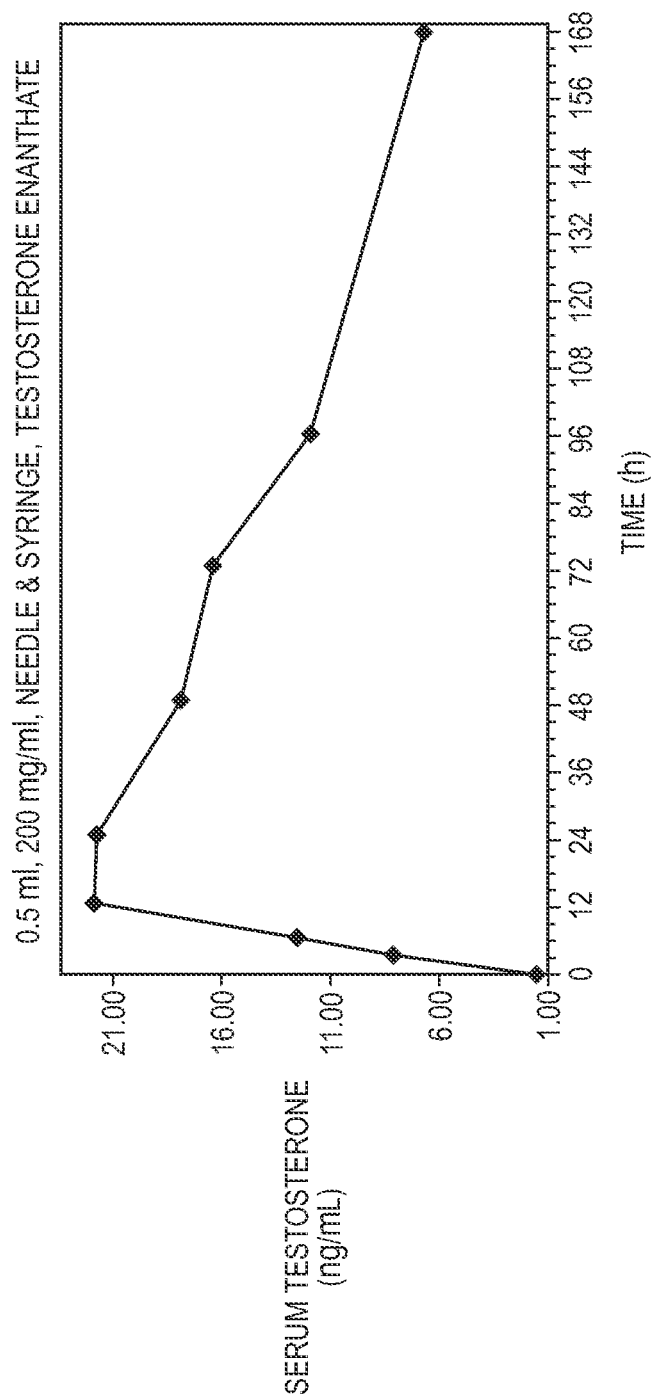
FIG. 17 is graph illustrating the serum concentration of testosterone for a 0.5 ml needle and syringe injection of 200 mg/ml testosterone enanthate in sesame oil.
Figure 18:
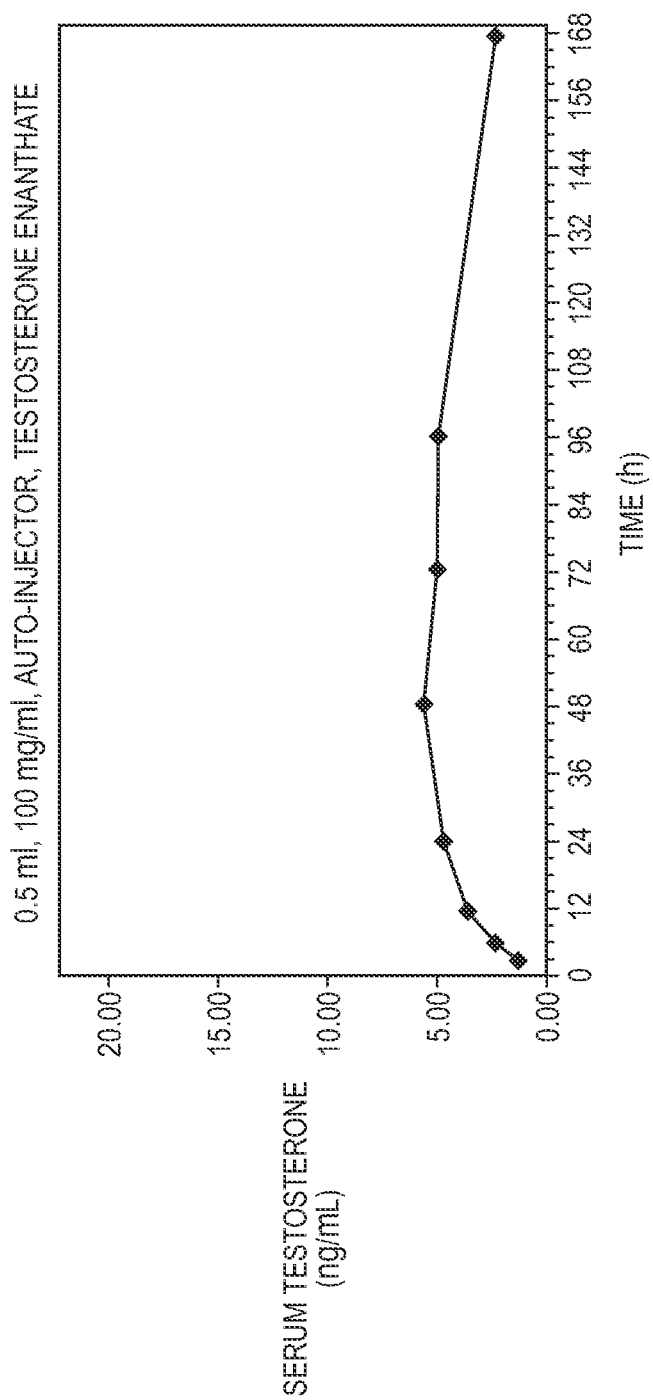
FIG. 18 is graph illustrating the serum concentration of testosterone for a 0.5 ml auto-injector injection of 100 mg/ml testosterone enanthate in sesame oil.
Figure 19:
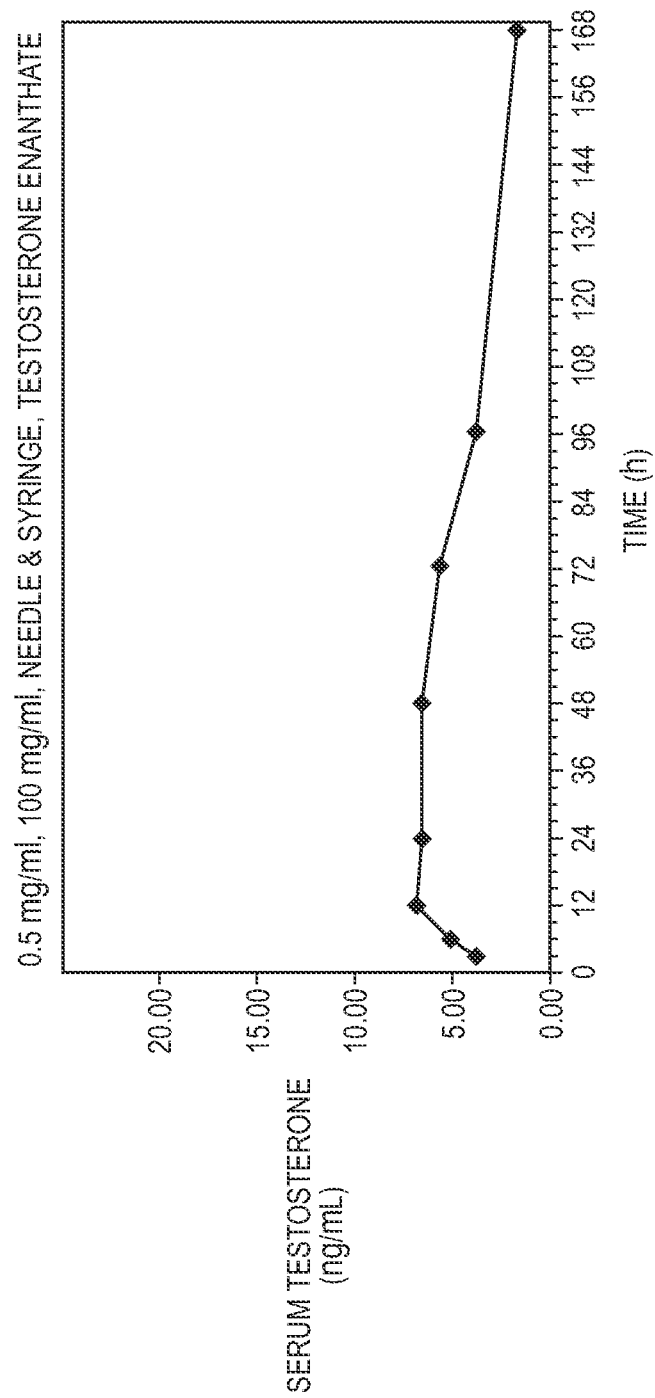
FIG. 19 is graph illustrating the serum concentration of testosterone for a 0.5 ml needle and syringe injection of 100 mg/ml testosterone enanthate in sesame oil.

In some embodiments, the level of testosterone is maintained as illustrated in FIG. 12. In an embodiment, the level of testosterone maintained as illustrated in FIG. 12 is in a mammal. In an embodiment, the level of testosterone maintained as illustrated in FIG. 12 is in the serum of a mammal. In an embodiment, the mammal is a human.

B. Maintenance of Plasma Testosterone at Elevated Levels or within Effective Levels In another embodiment, a method is provided herein for maintaining elevated plasma levels of testosterone in a mammal in need thereof. In certain embodiments, this entails maintaining plasma levels from a subcutaneous dose at or above therapeutic levels (e.g., about 400 ng/dl, about 500 ng/dl, about 600 ng/dl, about 700 ng/dl, about 800 ng./ml, about 900 ng/dl) for an extended period of time. In some embodiments the level is maintained for a period of time that is longer than an intramuscular dose of the same volume and concentration. In an embodiment, the method comprises administering a composition comprising a unit dose of testosterone (e.g., preservative-free) or pharmaceutically acceptable ester or salt thereof in a pharmaceutically acceptable carrier subcutaneously to a mammal, wherein after administration the plasma level of testosterone is maintained at an elevated level of up to about 1800 ng/dl for a period of time. In an embodiment, the time period for which plasma levels of testosterone are maintained at an elevated level is referred to as a "Z2 time period".

In some embodiments, the plasma level of testosterone is maintained at an elevated value selected from the group consisting of about 300 ng/dl to about 1800 ng/dl, about 400 ng/dl to about 1800 ng/dl, about 500 ng/dl to about 1800 ng/dl, about 600 ng/dl to about 1800 ng/dl, about 700 ng/dl to about 1800 ng/dl, about 800 ng/dl to about 1800 ng/dl, about 900 ng/dl to about 1800 ng/dl, about 1000 ng/dl to about 1800 ng/dl, about 300 ng/dl to about 1100 ng/dl, about 400 ng/dl to about 1100 ng/dl, about 500 ng/dl to about 1100 ng/dl, about 600 ng/dl to about 1100 ng/dl, about 700 ng/dl to about 1100 ng/dl, about 800 ng/dl to about 1100 ng/dl, about 300 ng/dl to about 1800 ng/dl, about 300 ng/dl to about 1700 ng/dl, about 300 ng/dl to about 1600 ng/dl, about 300 ng/dl to about 1500 ng/dl, about 300 ng/dl to about 1400 ng/dl, about 300 ng/dl to about 1300 ng/dl, about 300 ng/dl to about 1200 ng/dl, about 300 ng/dl to about 1100 ng/dl, about 300 ng/dl to about 1000 ng/dl, about 300 ng/dl to about 900 ng/dl, about 300 ng/dl to about 800 ng/dl, about 300 ng/dl to about 700 ng/dl, about 300 ng/dl to about 600 ng/dl, about 300 ng/dl to about 500 ng/dl, or about 300 ng/dl to about 400 ng/dl.

In certain embodiments, the blood plasma levels of testosterone are maintained primarily between 400 and 1100 ng/dl, more typically between 400 and 900 ng/dl, during the course of a treatment regimen. In certain embodiments, blood plasma levels at a value between about 400 and about 1000 ng/dl is considered "therapeutically effective," particularly for steady state maintenance of testosterone levels during a treatment regimen.

In an embodiment, a composition encompassed herein, when administered according to the methods and the devices encompassed herein, maintains the plasma level of testosterone at an elevated level starting at about 1 minute after administration and ending at about 1 month after administration. In an embodiment, a composition encompassed herein, when administered according to the methods and the devices encompassed herein, maintains the plasma level of testosterone at an elevated level starting at about 2 minutes after administration, or at about 3 minutes, about 4 minutes, about 5 minutes, about 10 minutes, about 20 minutes, about 30 minutes, about 45 minutes, about 60 minutes, about 2 hours, about 3 hours, about 4 hours, about 5 hours, about 6 hours about 7 hours about 8 hours about 9 hours, about 10 hours, about 11 hours, or about 12 hours after administration, up to about 1 month after administration. In an embodiment, a composition encompassed herein, when administered according to the methods and the devices encompassed herein, maintains the plasma level of testosterone at an elevated level starting at about 1 minute after administration and ending at about 25 days after administration, about 20 days after administration, about 15 days after administration, about 14 days after administration, about 13 days after administration, about 12 days after administration, about 11 days after administration, about 10 days after administration, about 9 days after administration, about 8 days after administration, about 7 days after administration, about 6 days after administration, about 5 days after administration, about 4 days after administration, about 3 days after administration, about 2 days after administration, about 1 day after administration, or about 0.5 days after administration.

C. Peak Plasma Concentration

In another embodiment, a method is provided herein for obtaining a peak plasma levels of testosterone in a mammal in need thereof. In an embodiment, a method is provided herein, using the compositions and devices encompassed herein, to obtain a peak plasma concentration of testosterone, after which the plasma concentration of testosterone decreases to a therapeutically effective level for a period of time. In another embodiment, a method is provided herein, using the compositions and devices encompassed herein, to obtain a peak plasma concentration of testosterone, after which the plasma concentration of testosterone decreases to an elevated level for a period of time.

In some embodiments, a peak level of testosterone is in the range of about 400 ng/dl to 2400 ng/dl, 500 ng/dl to 2400 ng/dl, 600 ng/dl to 2400 ng/dl, 700 ng/dl to 2400 ng/dl, 800 ng/dl to 2400 ng/dl, 900 ng/dl to 2400 ng/dl, 1000 ng/dl to 2400 ng/dl, 1100 ng/dl to 2400 ng/dl, 1200 ng/dl to 2400 ng/dl, 1300 ng/dl to 2400 ng/dl, 1400 ng/dl to 2400 ng/dl, 1500 ng/dl to 2400 ng/dl, 1600 ng/dl to 2400 ng/dl, 1700 ng/dl to 2400 ng/dl, 1800 ng/dl to 2400 ng/dl, 1900 ng/dl to 2400 ng/dl, 2000 ng/dl to 2400 ng/dl, 2100 ng/dl to 2400 ng/dl, 2200 ng/dl to 2400 ng/dl, or about 2300 ng/dl to 2400 ng/dl.

In another embodiment, a method is provided herein, using the compositions and devices encompassed herein, to obtain a peak plasma concentration of testosterone, after which the plasma concentration of testosterone decreases to lower-than-peak level for a period of time, the lower-than-peak level selected from about 300 ng/dl to about 1800 ng/dl, about 400 ng/dl to about 1800 ng/dl, about 500 ng/dl to about 1800 ng/dl, about 600 ng/dl to about 1800 ng/dl, about 700 ng/dl to about 1800 ng/dl, about 800 ng/dl to about 1800 ng/dl, about 900 ng/dl to about 1800 ng/dl, about 1000 ng/dl to about 1800 ng/dl, about 300 ng/dl to about 1100 ng/dl, about 400 ng/dl to about 1100 ng/dl, about 500 ng/dl to about 1100 ng/dl, about 600 ng/dl to about 1100 ng/dl, about 700 ng/dl to about 1100 ng/dl, about 800 ng/dl to about 1100 ng/dl, about 300 ng/dl to about 1800 ng/dl, about 300 ng/dl to about 1700 ng/dl, about 300 ng/dl to about 1600 ng/dl, about 300 ng/dl to about 1500 ng/dl, about 300 ng/dl to about 1400 ng/dl, about 300 ng/dl to about 1300 ng/dl, about 300 ng/dl to about 1200 ng/dl, about 300 ng/dl to about 1100 ng/dl, about 300 ng/dl to about 1000 ng/dl, about 300 ng/dl to about 900 ng/dl, about 300 ng/dl to about 800 ng/dl, about 300 ng/dl to about 700 ng/dl, about 300 ng/dl to about 600 ng/dl, about 300 ng/dl to about 500 ng/dl, or about 300 ng/dl to about 400 ng/dl.

In an embodiment, a method is provided herein, using the compositions and devices encompassed herein, to obtain a peak plasma concentration of testosterone, in which the peak plasma concentration of testosterone is achieved in about 48 hours, about 36 hours, about 24 hours, about 18 hours, about 12 hours, about 11 hours, about 10 hours, about 9 hours, about 8 hours, about 7 hours, about 6 hours, about 5 hours, about 4 hours, about 3 hours about 2 hours, about 1 hours, or about 0.5 hours. In an embodiment, the peak plasma concentration of testosterone is achieved in less than 48 hours, less than 36 hours, less than 24 hours, less than 18 hours, less than 12 hours, less than 11 hours, less than 10 hours, less than 9 hours, less than 8 hours, less than 7 hours, less than 6 hours, less than 5 hours, less than 4 hours, less than 3 hours less than 2 hours, less than 1 hours, or less than 0.5 hours.

D. Maintenance of Effective Levels of Testosterone after Comparative Dose Decreases Below Effective Levels In an embodiment, it was surprisingly found that administration of a testosterone composition as encompassed herein provides a plasma level of testosterone that is maintained at a therapeutically-effective level for a longer period of time than an equivalent dose of testosterone when administered to the same subject via one of a transdermal cream, gel or patch or needle and syringe, intramuscularly, intradermally, or subcutaneously. In an embodiment, at a time post-injection, a testosterone composition as encompassed herein (e.g., preservative-free) maintains a higher plasma concentration of testosterone than would a equivalent testosterone administered to the same subject via one of a transdermal cream, gel or patch or intramuscular injection by needle and syringe over the same time period.

With reference to the figures and in particular FIG. 12, in one embodiment, a method of administering testosterone comprises administering a composition comprising a unit dose of testosterone in a pharmaceutically acceptable carrier subcutaneously to a mammal, wherein after administration the plasma level of testosterone is maintained between about 700 ng/dl and about 1800 ng/dl for a time period, "Z2", wherein the plasma level of testosterone is also maintained between about 300 ng/dl and about 1100 ng/dl for a time period, "Z3", which is the time after the plasma level of an equivalent intramuscularly administered dose drops below the plasma level of the subcutaneously administered dose at the same time point post-administration.

In an embodiment, the plasma level of an equivalent intramuscularly administered dose drops below the plasma level of the subcutaneously administered dose at about 1 day post-administration, at about 2 days post-administration, at about 3 days post-administration, at about 4 days post-administration, at about 5 days post-administration, at about 6 days post-administration, at about 7 days post-administration, at about 8 days post-administration, at about 9 days post-administration, at about 10 days post-administration, at about 11 days post-administration, at about 12 days post-administration, at about 13 days post-administration, or at about 14 days post-administration.

In an embodiment, and with reference to FIG. 12, post administration, the plasma level of testosterone is maintained, for a Z2 time period, at or between a level selected from: about 700 ng/dl and about 1800 ng/dl, about 750 ng/dl and about 1750 ng/dl, about 800 ng/dl and about 1700 ng/dl, about 850 ng/dl and about 1650 ng/dl, about 900 ng/dl and about 1600 ng/dl, about 950 ng/dl and about 1550 ng/dl, about 1000 ng/dl and about 1500 ng/dl, about 1050 ng/dl and about 1450 ng/dl, about 1100 ng/dl and about 1400 ng/dl, about 1150 ng/dl and about 1350 ng/dl, and about 1200 ng/dl and about 1300 ng/dl.

In an embodiment, after administration, the plasma level of testosterone is maintained, for a Z2 time period, at a level selected from the group consisting of about 700 ng/dl, about 750 ng/dl, about 800 ng/dl, about 850 ng/dl, about 900 ng/dl, about 950 ng/dl, about 1000 ng/dl, about 1050 ng/dl, about 1100 ng/dl, about 1150 ng/dl, about 1200 ng/dl, about 1250 ng/dl, about 1300 ng/dl, about 1350 ng/dl, about 1400 ng/dl, about 1450 ng/dl, about 1500 ng/dl, about 1550 ng/dl, about 1600 ng/dl, about 1650 ng/dl, about 1700 mg/ml, about 1750 mg/ml, and about 1800 ng/dl.

In an embodiment, a Z2 time period is at least 1 hour, at least 2 hours, at least 3 hours, at least 4 hours, at least 5 hours, at least 6 hours, at least 12 hours, at least 18 hours, at least 24 hours, at least 36 hours, at least 48 hours, or at least 72 hours.

In an embodiment, the plasma level of testosterone is maintained above the plasma level for testosterone administered via an equivalent intramuscularly administered dose at the same point in time, for a Z3 time period. In another embodiment, the plasma level of testosterone is maintained above therapeutic levels of testosterone for a Z3 time period.

In yet another embodiment, and with reference to FIG. 12, after administration, the plasma level of testosterone is maintained for a Z3 time period after the plasma level of an equivalent intramuscularly administered dose drops below the plasma level of the subcutaneously administered dose at the same time point post-administration, at a value selected from the group consisting of about 300 ng/dl to about 1100 ng/dl, about 350 ng/dl to about 1050 ng/dl, about 400 ng/dl to about 1000 ng/dl, about 450 ng/dl to about 950 ng/dl, about 500 ng/dl to about 900 ng/dl, about 550 ng/dl to about 850 ng/dl, about 600 ng/dl to about 800 ng/dl, about 650 ng/dl to about 750 ng/dl, about 675 ng/dl to about 725 ng/dl and above about 300 ng/dl.

In an embodiment, after administration, the plasma level of testosterone is maintained, for a Z3 time period after the plasma level of an equivalent intramuscularly administered dose drops below the plasma level of the subcutaneously administered dose at the same time point post-administration, at a value selected from the group consisting of about 300 ng/dl, about 350 ng/dl, about 400 ng/dl, about 450 ng/dl, about 500 ng/dl, about 550 ng/dl, about 600 ng/dl, about 650 ng/dl, about 700 ng/dl, about 750 ng/dl, about 800 ng/dl, about 850 ng/dl, about 900 ng/dl, about 950 ng/dl, about 1000 ng/dl, about 1050 ng/dl, and about 1100 ng/dl.

In an embodiment, a Z3 time period is at least 1 hour, at least 2 hours, at least 3 hours, at least 4 hours, at least 5 hours, at least 6 hours, at least 12 hours, at least 18 hours, at least 24 hours, at least 36 hours, at least 48 hours, or at least 72 hours.

E. Maintenance of Effective Levels Over Multiple Treatments

Multiple treatments may include administration of two or more doses of testosterone (e.g., preservative-free) according to a combination of compositions, devices, and methods encompassed herein. In an embodiment, the plasma level of testosterone in the Z3 time period is maintained at therapeutically effective levels (e.g., a steady state at or above 300 ng/dl or at or above about 400 ng/dl or other potential values as described hereinabove). In an embodiment, the plasma level of testosterone in the Z3 time period is maintained at or above a therapeutically effective level while a second dose is administered. In an embodiment, the plasma level of testosterone in the Z3 time period is maintained above a therapeutically effective level until a second dose is administered. In an embodiment, the plasma level of testosterone in the Z3 time period is maintained at an elevated level. In an embodiment, the plasma level of testosterone in the Z3 time period is maintained at a level between 300 ng/dl and 700 ng/dl, between 300 ng/dl and 1100 ng/dl, between 300 ng/dl and 1800 ng/dl, between 700 ng/dl and 1100 ng/dl, between 700 ng/dl and 1800 ng/dl, or between 1100 ng/dl and 1800 ng/dl, and/or above about 300 ng/dl, until a second dose is administered, when after the blood levels of testosterone will likely increase again in accordance with well understood pharmacokinetics.

In an embodiment, administration of a testosterone composition as encompassed herein provides a stimulatory effect immediately after injection, such that the plasma level of testosterone is above a plasma therapeutic level of testosterone for a period of time, but not so high as to be toxic to the subject. In an embodiment, stimulatory levels of plasma testosterone can be detected by measuring the plasma levels of testosterone. In another embodiment, stimulatory levels of testosterone can be detected by measuring a surrogate for plasma testosterone levels, such as, but not limited to, one or more endocrinology profiles of the subject to which the testosterone was administered. In an embodiment, endocrinology markers include, but are not limited to, red blood cell proliferation and/or other markers indicative of hormonal function.

F. Stimulatory Effect

In another embodiment, administration of a testosterone composition as encompassed herein provides a stimulatory effect immediately after injection, such that the plasma level of testosterone is above a plasma therapeutic level of testosterone for a period of time, but not so high as to be toxic to the subject. After the plasma levels of testosterone fall from the stimulatory levels, the plasma levels of testosterone are within the therapeutically effective levels as discussed herein. In an embodiment, administration of a testosterone composition as encompassed herein provides a minimal stimulatory effect immediately after injection, such that the plasma level of testosterone is above a plasma therapeutic level of testosterone for a period of time, but not so high as to be toxic to the subject, after which the plasma levels of testosterone are within the therapeutically effective levels as discussed herein. In an embodiment, administration of a testosterone composition as encompassed herein provides no stimulatory effect immediately after injection, and the plasma level of testosterone is maintained at a therapeutically effective level as discussed herein.

In an embodiment, testosterone administered to a subject in accordance with the methods of the invention provides pharmacokinetics, including systemic bioavailability, that has diminished pharmacokinetics, including systemic bioavailability, of testosterone when the same dose of testosterone is administered to said subject using needle and syringe, intramuscularly or subcutaneously.

EXAMPLES

Example 1: Injection of Viscous Fluid Compositions

A formulation was prepared including arachis oil and 10% benzyl alcohol and an active pharmaceutical ingredient based on testosterone. This formulation had a viscosity of 1000 cps. An MJ-7 needlefree injection device made by Antares Pharma was used to administer 0.5 ml of the formulation. The study used the following device power and needle-free syringe orifice settings to achieve needle-free injection of and arachis oil-10% benzyl alcohol solution.

For achieving intramuscular injections, the injection device was powered with a spring having a spring force of 100 lbs and was equipped with a needle-free syringe having an orifice of 0.36 mm (0.014") diameter.

For achieving subcutaneous injections, the injection device was powered with a spring having a spring force of 85 lbs and was equipped with a needle-free syringe having an orifice of 0.28 mm (0.011") diameter.

Results are as follows:

TABLE 3

Intramuscular injections.

| Intramuscular injections | Complete | | Incomplete, or wet, injections | |
|---|---|---|---|---|
| Needle free | 40 | 83% | 8 | 17% |
| Needle and syringe with IM needle | 47 | 98% | 1 | 2% |

TABLE 4

Subcutaneous injections

| Subcutaneous injections | Complete | | Incomplete, or wet, injections | |
|---|---|---|---|---|
| Needle free | 23 | 48% | 25 | 52% |
| Needle and syringe with SC needle | 22 | 46% | 26 | 54% |

In an embodiment, it will be understood that when mini-needle devices are used instead of needless injection devices, the needle bores would be on the same order as the orifices of the needle-free devices.

Example 2: Comparison of Cavg and Cmax for Various Testosterone Formulations and Methods of Delivery Experimental protocols and references for available data on the Cavg-Cmax can be found in package insert labels of Androgel 1% (NDA No. 021015), Androgel 1.62% (NDA No. 022309), Testim (NDA No. 021454) and Axiron (NDA No. 022504).

TABLE 5

Comparison of Cavg and Cmax calculated for Androgel and Testim at various concentrations.

| | Agel 20.25 | Agel 40.5 | Agel 60.75 | Agel 81 | Testim 50 | Testim 100 |
|---|---|---|---|---|---|---|
| Cav | 386 | 474 | 513 | 432 | 365 | 612 |
| Cmax | 562 | 715 | 839 | 649 | 538 | 897 |
| Cmax/Cav | 1.455959 | 1.508439 | 1.635478 | 1.502315 | 1.473973 | 1.465686 |

TABLE 6

Comparison of Cavg and Cmax calculated for Axiron and testosterone enanthate at various concentrations.

| | AX 60 | AX 90 | AX 120 | TE 100 | TE 200 |
|---|---|---|---|---|---|
| Cav | 506 | 415 | 390 | 1021 | 924 |
| Cmax | 839 | 664 | 658 | 1299 | 1315 |
| Cmax/Cav | 1.658103 | 1.6 | 1.687179 | 1.272282 | 1.42316 |

Example 3: Pharmacokinetic Study of Testosterone by Injection in Castrated Minipigs The objective of this study was to evaluate the pharmacokinetics of testosterone (Antares QS Autoinjector Device with 10 mm injection depth) when administered via injection to castrated minipigs on Days 1 and 15.

The test system included minipigs of the Yucatan strain. Castrated male minipigs were obtained from Sinclair Research Center, Inc., Windham, Me. Minipigs were 15 to 20 weeks old, and the target Weight at the initiation of dosing was 20 to 25 kg. The Yucatan minipig was chosen as the animal model for this study as it is a preferred non-rodent species for preclinical toxicity testing by regulatory agencies. Housing and care was as specified in the USDA Animal Welfare Act (9 CFR, Parts 1, 2, and 3) and as described in the *Guide for the Care and Use of Laboratory Animals* from the National Research Council. The animals were individually housed in swine pens/cages.

The experiment was designed as follows:

| Group No. | No. of male animals | Test material | Dose volume |
|---|---|---|---|
| 1 | 3 | testosterone, 100 mg | 0.5 ml |
| 2 | 3 | testosterone, 200 mg | 0.5 ml |

Test articles used for injection of animals included: test article 1, testosterone enanthate at 100 mg/ml in pre-filled syringes; test article 2, testosterone enanthate at 200 mg/ml in pre-filled syringes; test article 3, testosterone enanthate at 100 mg/ml in vials; and test article 4, testosterone enanthate at 200 mg/ml in vials.

On Day 1, dose material was delivered by a pre-loaded Antares QS Autoinjector Device (see. e.g., application Ser. No. 61/763,395, which is incorporated by reference). On Day 15, dose material was delivered by needle and syringe. Test Articles 1 and 2 were administered to the appropriate animals via injection using a mini-needle auto-injector into the scapular region on Day 1 to Test Site 1. The animal's dorsal surface area was clipped free of hair with a small animal clipper before the first dose and as often as necessary thereafter to allow for clear visualization of the test site. Care was taken during the clipping procedure to avoid abrasion of the skin. The injection site (approximately 2 cm×2 cm) was delineated with an indelible marker and remarked as necessary thereafter. Test Articles 3 and 4 were administered to the appropriate animals via intramuscular injection using a 1 mL syringe with a 27 gauge×1 inch needle into the proximal portion of the hindlimb to an approximate depth of ¾ inch on Day 15 to Test Site 2. The animal's proximal hindlimb was clipped free of hair with a small animal clipper before the first dose and as often as necessary thereafter to allow for clear visualization of the test site. Care was taken during the clipping procedure to avoid abrasion of the skin. The injection site (approximately 2 cm×2 cm) was delineated with an indelible marker and remarked as necessary thereafter. Following all Day 22 study observations and bioanalytical sample collection, the animals (including the alternate male pig) were assigned to the exploratory trial phase of this study. The animal's dorsal surface area was clipped free of hair with a small animal clipper before the first dose and as often as necessary thereafter to allow for clear visualization of the test site. The QS Autoinjector Device was used to deliver a 0.5 mL dose of dye via injection, into naïve scapular area. The naïve proximal portion of the hindlimb was injected with a 0.5 mL dose of dye via intramuscular injection using a 27 gauge×1 inch needle and syringe. The injection sites (approximately 2 cm×2 cm) were delineated with an indelible marker. Following dose administration, the animals (including the alternate animal) were subjected to euthanasia and examination. The first day of dosing was designated as Study Day 1.

An injectable route of exposure was selected because this is the intended route of human exposure. An injection depth of 10 mm was investigated as part of this study. Dose levels of 100 mg and 200 mg were determined to provide comparison of the intramuscular route of administration via autoinjector and needle and syringe, for toxicokinetic purposes. The intramuscular route was selected for further investigation, as this route resulted in less material loss post injection than subcutaneous administration based on macroscopic observations. Doses lower than 100 mg may not have provided necessary circulating concentrations, while doses over 200 mg were not required. Dose levels and weekly dose regimen were based on the following supplied reference document "Daily Testosterone and Gonadotropin Levels Are Similar in Azoospermic and Nonazoospermic Normal Men Administered Weekly Testosterone: Implications for Male contraceptive Development" Journal of Andrology Vol. 22, No. 6 November/December 2001.

The injection sites of each animal were observed on the day of randomization and daily from Days 1 to 22 (at approximately 1 and 4 hours postdose on the days of dosing and once daily on non-dosing days). Particular attention was paid to the injection sites regarding erythema, edema, and any other additional adverse findings.

Blood was collected by venipuncture of the vena cava. Samples were collected according to the following table:

| TK Sample Collection Schedule Group No. Sample Collection Time Points (Time Post Dose) on Days 1 and 15 | | | | | | | | |
|---|---|---|---|---|---|---|---|---|
| 0 hr | 3 hr | 6 hr | 12 hr | 24 hr | 48 hr | 72 hr | 96 hr | 168 hr |
| 1 X | X | X | X | X | X | X | X | X |
| 2 X | X | X | X | X | X | X | X | X |

X = sample to be collected; — = not applicable, (zero hour sample collected before dosing)
Target Volume: 3.0 mL
Anticoagulant: None
Processing: To serum Blood was collected by venipuncture of the vena cava. Samples were collected according to the following table: Samples were allowed to clot at room temperature for at least 30 minutes before centrifugation.

The samples were centrifuged at ambient temperature at 1800×g. The resulting serum was separated into 3 aliquots of approximately 0.5 mL each for analysis. One aliquot was designated for testosterone and DHT analysis, 1 aliquot for analysis of Sex Hormone Binding Globulin (SHBG), and 1 aliquot for determination of total serum albumin. The serum samples were transferred into uniquely labeled polypropylene tubes and stored frozen in a freezer set to maintain −70° C. Samples to be analyzed were shipped overnight on dry ice to the bioanalytical laboratory for analysis.

One set of serum samples was analyzed for concentration of total testosterone using a validated analytical procedure. The samples collected for sex hormone binding globulin (SHBG) and serum albumin will not be analyzed at this time. DHT was not analyzed for this study. Testosterone analysis was performed by LCMS using a method validated under Charles River Study 20027106. Data collection was performed using Analyst from MDS Sciex. Statistical analyses including regression analysis and descriptive statistics including arithmetic means and standard deviations, accuracy and precision were performed using Watson Laboratory Information Management System (LIMS) and Microsoft Excel.

Toxicokinetic parameters were estimated using Watson Laboratory Information Management System (LIMS) and Microsoft Excel. A non-compartmental approach consistent with the subcutaneous and intramuscular route of administration was used for parameter estimation. Individual and mean PK parameters were reported and included Cmax, Tmax, and AUC0-last. When data permitted, the slope of the terminal elimination phase of each concentration versus time curve was determined by log-linear regression, and the following additional parameters were also estimated: AUC0-inf, terminal elimination half-life. All parameters were generated from testosterone (total) concentrations in serum from Days 1 and 15 unless otherwise stated. Parameters were estimated using sampling times relative to the start of each dose administration.

FIGS. 13-19 illustrate, in part, the results of the studies described in Example 3, for various testosterone enanthate concentrations delivered by either auto-injector or traditional needle and syringe methods.

No animals died during the course of the study. There were no test article-related clinical signs during the study. Sporadic occurrences of scabs, reddened areas, or mechanical injury were noted during the study. These were considered background findings associated with the animal rubbing against the cage or areas that were irritated during dosing procedures while the animals were in the sling. One animal was noted as struggling during dosing on Day 15; however, this did not appear to affect dose administration.

A small amount of material injected at each test site leaked from the injection site once the device or needle was removed. The amount of leakage was comparable across the sites and animals. Additionally, redness was noted at the injection site after injection across the test sites. There were no additional dermal changes noted during the study interval.

No test article-related effects on body weight occurred during the study. All animals showed an increase in weight from their starting weight during the study. The results of the trial with the injection of dye in sesame oil resulted in verification of subcutaneous delivery in all animals that received a dose from the QS Autoinjector Device. Conventional administration via needle and syringe administration resulted in intramuscular delivery of the dye, except in 1 animal that had subcutaneous delivery with a dark area in the muscle.

Each and every reference herein is incorporated by reference in its entirety. The entire disclosure of U.S. Pat. Nos. 8,021,335, 7,776,015, and 6,391,003 and PCT application publication WO 2010/108116 are also hereby incorporated herein by reference thereto as if fully set forth herein.

It will be appreciated by those skilled in the art that changes could be made to the exemplary embodiments described above without departing from the broad inventive concept thereof. It is understood, therefore, that this invention is not limited to the exemplary embodiments described, but it is intended to cover modifications within the spirit and scope of the present invention as defined by the claims. For example, specific features of the exemplary embodiments may or may not be part of the claimed invention and features of the disclosed embodiments may be combined.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed:

1. A method of administering testosterone comprising:
    administering a preservative-free composition comprising a unit dose of testosterone or a pharmaceutically acceptable ester or salt thereof in a pharmaceutically acceptable carrier subcutaneously to a mammal,
    wherein after administration, a plasma level of testosterone is maintained between about 200 ng/dl and about 1800 ng/dl for a Z1 time period,
    wherein the Z1 time period is at least 1 day, and
    wherein administering the preservative-free composition consists of an injection via a powered injector comprising a housing, a chamber disposed within the housing and configured to receive the preservative-free composition, and a needle operatively associated with the chamber.

2. The method of claim 1, wherein the plasma level of testosterone is maintained at a value selected from the group consisting of about 300 ng/dl to about 1100 ng/dl, about 350 ng/dl to about 1050 ng/dl, about 400 ng/dl to about 1000 ng/dl, about 450 ng/dl to about 950 ng/dl, about 500 ng/dl to about 900 ng/dl, about 550 ng/dl to about 850 ng/dl, about 600 ng/dl to about 800 ng/dl, about 650 ng/dl to about 750 ng/dl, and about 675 ng/dl to about 725 ng/dl.

3. The method of claim 1, wherein the plasma level of testosterone is maintained at a value selected from the group consisting of about 300 ng/dl, about 350 ng/dl, about 400 ng/dl, about 450 ng/dl, about 500 ng/dl, about 550 ng/dl, about 600 ng/dl, about 650 ng/dl, about 700 ng/dl, about 750 ng/dl, about 800 ng/dl, about 850 ng/dl, about 900 ng/dl, about 950 ng/dl, about 1000 ng/dl, about 1050 ng/dl, and about 1100 ng/dl.

4. The method of claim 1, wherein the plasma level of testosterone is maintained at a value selected from the group consisting of at least about 300 ng/dl, at least about 350 ng/dl, at least about 400 ng/dl, at least about 450 ng/dl, at least about 500 ng/dl, at least about 550 ng/dl, at least about 600 ng/dl, at least about 650 ng/dl, at least about 700 ng/dl, at least about 750 ng/dl, at least about 800 ng/dl, at least about 850 ng/dl, at least about 900 ng/dl, at least about 950 ng/dl, at least about 1000 ng/dl, at least about 1050 ng/dl, and at least about 1100 ng/dl.

5. The method of claim 1, wherein the Z1 time period is at least 6 days.

6. The method of claim 1, wherein the Z1 time period is at least 6.5 days.

7. The method of claim 1, wherein the Z1 time period is at least 7 days.

8. The method of claim 1, wherein the preservative-free composition comprises a liquid composition.

9. The method of claim 1, wherein administering the preservative-free composition consists of administering a single unit dose.

10. A method of administering testosterone comprising:
    administering a preservative-free composition comprising a unit dose of testosterone or pharmaceutically acceptable ester or salt thereof in a pharmaceutically acceptable carrier subcutaneously to a mammal,
    wherein after administration the plasma level of testosterone is maintained at a therapeutically effective level for a Z2 time period,
    wherein the Z2 time period is at least 1 day, and
    wherein administering the preservative-free composition consists of a single injection via a powered injector comprising a housing, a chamber disposed within the housing and configured to receive the preservative-free composition, and a needle operatively associated with the chamber.

11. The method of claim 10, wherein the preservative-free composition comprises a liquid composition.

12. A method of maintaining elevated plasma levels of testosterone in a mammal in need thereof comprising administering a preservative-free composition comprising:
    a unit dose of testosterone or pharmaceutically acceptable ester or salt thereof in a pharmaceutically acceptable carrier subcutaneously to a mammal,
    wherein after administration the plasma level of testosterone is maintained at a therapeutically effective level of up to about 1800 ng/dl for a Z2 time period,
    wherein the Z2 time period is at least 1 day, and
    wherein administering the preservative-free composition consists of a single injection via a powered injector comprising a housing, a chamber disposed within the housing and configured to receive the preservative-free composition, and a needle operatively associated with the chamber.

13. The method of claim 12, wherein the preservative-free composition comprises a liquid composition.

14. A method of administering testosterone comprising administering a preservative-free composition comprising a unit dose of testosterone or pharmaceutically acceptable ester or salt thereof in a pharmaceutically acceptable carrier subcutaneously to a mammal, wherein after administration the plasma level of testosterone is maintained between about 700 ng/dl and about 1800 ng/dl for a Z2 time period, wherein the plasma level of testosterone is also maintained between about 300 ng/dl and about 1100 ng/dl for Z3 time period, after the plasma level of an equivalent intramuscularly administered dose drops below the plasma level of the subcutaneously administered dose at the same time point post-administration, and wherein administering the preservative-free composition consists of an injection via a powered injector comprising a housing, a chamber disposed within the housing and configured to receive the preservative-free composition, and a needle operatively associated with the chamber.

15. The method of claim 14, wherein after administration, the plasma level of testosterone is maintained, for a Z2 time period, at a level selected from the group consisting of about 750 ng/dl and about 1750 ng/dl, about 800 ng/dl and about 1700 ng/dl, about 850 ng/dl and about 1650 ng/dl, about 900 ng/dl and about 1600 ng/dl, about 950 ng/dl and about 1550 ng/dl, about 1000 ng/dl and about 1500 ng/dl, about 1050 ng/dl and about 1450 ng/dl, about 1100 ng/dl and about 1400 ng/dl, about 1150 ng/dl and about 1350 ng/dl, and about 1200 ng/dl and about 1300 ng/dl.

16. The method of claim 14, wherein after administration, the plasma level of testosterone is maintained, for a Z2 time period, at a level selected from the group consisting of about 700 ng/dl, about 750 ng/dl, about 800 ng/dl, about 850 ng/dl, about 900 ng/dl, about 950 ng/dl, about 1000 ng/dl, about 1050 ng/dl, about 1100 ng/dl, about 1150 ng/dl, about 1200 ng/dl, about 1250 ng/dl, about 1300 ng/dl, about 1350 ng/dl, about 1400 ng/dl, about 1450 ng/dl, about 1500 ng/dl, about 1550 ng/dl, about 1600 ng/dl, about 1650 ng/dl, about 1700 mg/ml, about 1750 mg/ml, and about 1800 ng/dl.

17. The method of claim 14, wherein the plasma level of testosterone is maintained for a Z3 time period after the plasma level of an equivalent intramuscularly administered dose drops below the plasma level of the subcutaneously administered dose at the same time point post-administration, at a value selected from the group consisting of about 350 ng/dl to about 1050 ng/dl, about 400 ng/dl to about 1000 ng/dl, about 450 ng/dl to about 950 ng/dl, about 500 ng/dl to about 900 ng/dl, about 550 ng/dl to about 850 ng/dl, about 600 ng/dl to about 800 ng/dl, about 650 ng/dl to about 750 ng/dl, and about 675 ng/dl to about 725 ng/dl.

18. The method of claim 14, wherein the plasma level of testosterone is maintained, for Z3 time period after the plasma level of an equivalent intramuscularly administered dose drops below the plasma level of the subcutaneously administered dose at the same time point post-administration, at a value selected from the group consisting of about 300 ng/dl, about 350 ng/dl, about 400 ng/dl, about 450 ng/dl, about 500 ng/dl, about 550 ng/dl, about 600 ng/dl, about 650 ng/dl, about 700 ng/dl, about 750 ng/dl, about 800 ng/dl, about 850 ng/dl, about 900 ng/dl, about 950 ng/dl, about 1000 ng/dl, about 1050 ng/dl, and about 1100 ng/dl.

* * * * *